US012611406B2

(12) United States Patent
Kessler et al.

(10) Patent No.: US 12,611,406 B2
(45) Date of Patent: Apr. 28, 2026

(54) OXOPIPERAZINE DERIVATIVES FOR THE TREATMENT OF CANCER

(71) Applicant: Inthera Bioscience AG, Zürich (CH)

(72) Inventors: Ulrich Kessler, Zurich (CH); Beatrice Dolores Pilger Kessler, Zurich (CH); Valentino Cattori, Zurich (CH)

(73) Assignee: Inthera Bioscience AG, Zurich (CH)

( * ) Notice: Subject to any disclaimer, the term of this patent is extended or adjusted under 35 U.S.C. 154(b) by 554 days.

(21) Appl. No.: 18/002,169

(22) PCT Filed: Jun. 18, 2021

(86) PCT No.: PCT/EP2021/066611
§ 371 (c)(1),
(2) Date: Dec. 16, 2022

(87) PCT Pub. No.: WO2021/255239
PCT Pub. Date: Dec. 23, 2021

(65) Prior Publication Data

US 2023/0226044 A1 Jul. 20, 2023

Related U.S. Application Data

(60) Provisional application No. 63/041,416, filed on Jun. 19, 2020.

(51) Int. Cl.
*A61K 31/496* (2006.01)
*A61P 35/00* (2006.01)

(52) U.S. Cl.
CPC ........... *A61K 31/496* (2013.01); *A61P 35/00* (2018.01)

(58) Field of Classification Search
CPC ........ A61K 31/496; A61K 45/06; A61P 35/00
See application file for complete search history.

(56) References Cited

U.S. PATENT DOCUMENTS 5,885,995 A 3/1999 Dinsmore
10,710,975 B2 7/2020 Labelle et al.
(Continued)

FOREIGN PATENT DOCUMENTS

CN 101341123 A 1/2009
CN 103732592 A 4/2014
(Continued)

OTHER PUBLICATIONS

Ali, I. et al., "Lysine Acetylation Goes Global: From Epigenetics to Metabolism and Therapeutics," Chem. Rev., 118:1216-1252 (2018).
(Continued)

*Primary Examiner* — San Ming R Hui
(74) *Attorney, Agent, or Firm* — Workman Nydegger

(57) ABSTRACT

The present disclosure provides a method of treating a cancer comprising administering Compound 1:
(Continued)

(Compound 1)

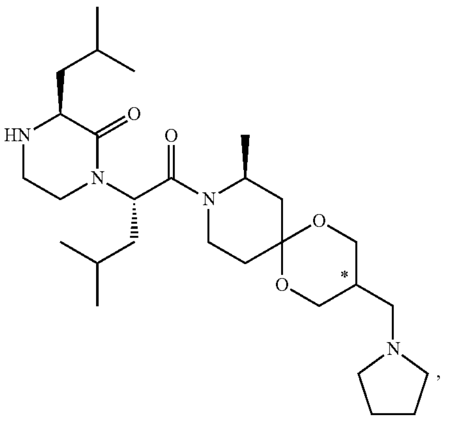

or a pharmaceutically acceptable salt, hydrate, solvate, or stereoisomer thereof, to a subject in need thereof at a dosage disclosed herein.

15 Claims, 18 Drawing Sheets

(56) References Cited

U.S. PATENT DOCUMENTS

| | | | |
|---|---|---|---|
| 11,306,068 | B2 | 4/2022 | Labelle et al. |
| 2020/0308139 | A1 | 10/2020 | Labelle et al. |
| 2022/0213057 | A1 | 7/2022 | Labelle et al. |

FOREIGN PATENT DOCUMENTS

| | | | |
|---|---|---|---|
| WO | WO-03017939 | A2 | 3/2003 |
| WO | WO-03033487 | A1 | 4/2003 |
| WO | WO-2004046111 | A1 | 6/2004 |
| WO | WO-2004066951 | A2 | 8/2004 |
| WO | WO-2007016496 | A2 | 2/2007 |
| WO | WO-2012021144 | A1 | 2/2012 |
| WO | WO-2013110134 | A1 | 8/2013 |
| WO | WO-2013123511 | A1 | 8/2013 |
| WO | WO-2014113794 | A2 | 7/2014 |
| WO | WO-2015160914 | A1 | 10/2015 |
| WO | WO-2015179547 | A2 | 11/2015 |
| WO | WO 2019/118973 | A1 | 6/2019 |
| WO | WO 2021/144302 | A1 | 7/2021 |

OTHER PUBLICATIONS

Attar, N. & Kurdistani, S. K., "Exploitation of EP300 and CREBBP Lysine Acetyltransferases by Cancer," Cold Spring Harb Perspect Med 2017;7:a026534, 15 pages.

[Author Unknown] "Khimicheskiy entsiklopedicheskiy slovar" (Chemical Encyclopedic Dictionary), Moscow: «Sovetskaya Entsiklopediya», 1983, pp. 130-131, and English translation of relevant portion, 7 pages.

Avantaggiati, M. L. et al., "Recruitment of p300/CBP in p53-Dependent Signal Pathways," Cell, 89:1175-1184 (1997).

Bedford, D. C. et al., "Target gene context influences the transcriptional requirement for the KAT3 family of CBP and p300 histone acetyltransferases," Epigenetics, 5(1):9-15 (2010).

Belikov, V.G, "Pharmaceutical Chemistry. Chapter 2.6 Relationship between the chemical structure, properties of substances and their effect on the body", MEDpress-inform (2007); pp. 27-29; 14 pages with English translation.

Benson, D. A. et al., "GenBank," Nucleic Acids Research, 41:(D36-D42) (2013).

Berge et al., "Pharmaceutical salts," Journal of Pharmaceutical Sciences, Jan. 1977, pp. 1-19.

Bernat, A et al., "Interaction between the HPV E7 oncoprotein and the transcriptional coactivator p300," Oncogene, 22:7871-7881 (2003).

Blobel, G. A., "CREB-binding protein and p300: molecular integrators of hematopoietic transcription," Blood, 95(3): 745-755 (2000).

Breen, M. E. & Mapp, A. K., "Modulating the masters: chemical tools to dissect CBP and p300 function," Current Opinion in Chemical Biology, 45:195-203 (2018).

Bundgaard, H. "Chapter 5: Design and Application of Pro-drugs", In A Textbook of Drug Design and Development, edited by Krogsgaard-Larsen and H. Bundgaard, (Jan. 1991), 113-191.

Bundgaard, H. "Means to Enhance Penetration. (1) Prodrugs as a means to improve the delivery of peptide drugs" Advanced Drug Delivery Reviews, 8:1-38 (1992).

Burslem, G. M. et al., "Hypoxia inducible factor (HIF) as a model for studying inhibition of protein-protein interactions," Chem. Sci., 8:4188-4202 (2017).

Cahn, R. S. & Ingold, C., "Spezifikation der molekularen Chiralitat," Angew. Chem., 78(8):413-447 (1966), with English language machine translation.

Cahn, R.S. "An introduction to the sequence rule: a system for the specification of absolute configuration". Journal of Chemical Education (Mar. 1964) 41(3): 116-125.

Cahn, R.S. et al. "Specification of Configuration about Quadricovalent Asymmetric Atoms". J Chem Soc, (1951), 612-622.

Cahn, R.S. et al. "Specification of Molecular Chirality" Agnew Chem Inter Edit, (1966) 5(4): 385-415, with Errata, p. 511.

Cahn, R.S. et al. "The specification of asymmetric configuration in organic chemistry". Experientia, (Mar. 1956) 12: 81-94.

Culig, Z., "Androgen Receptor Coactivators in Regulation of Growth and Differentiation in Prostate Cancer," J. Cell Physiol., 231:270-274 (2016).

Dancy, B. M. & Cole, P. A., "Protein Lysine Acetylation by p300/CBP," Chem. Rev., 115:2419-2452 (2015).

Dang, D. T. et al., "Hypoxia-Inducible Factor-1 Target Genes as Indicators of Tumor Vessel Response to Vascular Endothelial Growth Factor Inhibition," Cancer Res., 68(6):1872-1880 (2008).

Di Martile, M. et al., "The multifaceted role of lysine acetylation in cancer: prognostic biomarker and therapeutic target," Oncotarget, 7(34):55789-55810 (2016).

Dutta, R. et al., "CBP/p300 acetyltransferase activity in hematologic malignancies," Molecular Genetics and Metabolism, 119:37-43 (2016).

Eisenhauer, E. A. et al. (Jan. 2009) "New response evaluation criteria in solid tumors: Revised RECIST guideline (version 1.1)" Eur J Cancer, 45:228-247.

Fera, D. & Marmorstein, R., "Different Regions of the HPV-E7 and Ad-E1A Viral Oncoproteins Bind Competitively but through Distinct Mechanisms to the CH1 Transactivation Domain of p300," Biochemistry, 51:9524-9534 (2012).

Fleisher, D. et al., "Improved oral drug delivery: solubility limitations overcome by the use of prodrugs," Advanced Drug Delivery Reviews, 19:115-130 (1996).

Gao et al., "Expression of p300 and CBP is associated with poor prognosis in small cell lung cancer," Int J Clin Exp Pathol 2014;7(2):760-767.

GenBank Accession No. NP001420, histone acetyltransferase p300 isoform 1 [*Homo sapiens*], Feb. 26, 2019, 13 pages.

George, J. et al., "Comprehensive genomic profiles of small cell lung cancer," Nature 524, 47-53 (2015), and Methods and Extended Data, 14 pages. https://doi.org/10.1038/nature14664.

Goodman, R. H. & Smolik, S., "CBP/p300 in cell growth, transformation, and development," Genes & Development, 14:1553-1577 (2000).

Hottiger, M. O. et al., "Modulation of cytokine-induced HIV gene expression by competitive binding of transcription factors to the coactivator p300," The EMBO Journal, 17(11):3124-3134 (1998).

(56) References Cited

OTHER PUBLICATIONS

Kamei, Y. et al., "A CBP Integrator Complex Mediates Transcriptional Activation and AP-1 Inhibition by Nuclear Receptors," Cell, 85:403-414 (1996).
Kummerer, K. "Pharmaceuticals in the Environment", Annual Review of Environment and Resources, 2010, vol. 35, pp. 57-75, doi: 10.1146/annurev-environ-052809-161223.
Kushal, S. et al., "Protein domain mimetics as in vivo modulators of hypoxia-inducible factor signaling," PNAS, 110(39):15602-15607 (2013).
Lao, B. B. et al., "In vivo modulation of hypoxia-inducible signaling by topographical helix mimetics," PNAS, 111(21):7531-7536 (2014).
Lao, B. B. et al., "Rational Design of Topographical Helix Mimics as Potent Inhibitors of Protein-Protein Interactions," J. Am. Chem. Soc., 136:7877-7888 (2014).
Lee, C.-W. et al., "Functional interplay between p53 and E2F through co-activator p300," Oncogene, 16:2695-2710 (1998).
Leroy, B. et al., "TP53 Mutations in Human Cancer: Database Reassessment and Prospects for the Next Decade," Human Mutation, 35(6):672-688 (2014).
Li, Y. et al. (Mar. 4, 2003) "Selective killing of cancer cells by β-lapachone: Direct checkpoint activation as a strategy against cancer" Proceedings of the National Academy of Sciences, 100(5):2674-2678.
Mashkovsky, M.D., "Medicaments (Doctor's Manual)", 14th Edition, vol. 1., Moscow. (2001), pp. 11; 6 pages.
Massoud, G. N. & Li, W., "HIF-1α pathway: role, regulation and intervention for cancer therapy," Acta Pharm Sin B., 5(5):378-389 (2015).
Nakajima, T. et al., "The Signal-Dependent Coactivator CBP Is a Nuclear Target for pp90RSK," Cell, 86:465-474 (1996).
Nielsen NM et al. "Glycolamide esters as biolabile prodrugs of carboxylic acid agents: synthesis, stability, bioconversion, and physicochemical properties". Journal of Pharmaceutical Sciences, (Apr. 1988) 77(4): 285-298.
Ogiwara, H. et al., "Targeting p300 Addiction in CBP-Deficient Cancers Causes Synthetic Lethality by Apoptotic Cell Death due to Abrogation of MYC Expression," Cancer Discov; 6(4); 430-45 (2015).
Oser, M. G. et al., "Cells Lacking the RB1 Tumor Suppressor Gene Are Hyperdependent on Aurora B Kinase for Survival," Cancer Discov (2019), 9(2): 230-247.
Patel, D. et al., "The E6 protein of human papillomavirus type 16 binds to and inhibits co-activation by CBP and p300," The EMBO Journal, 18(18):5061-5072 (1999).
Pearson, et al., Improved tools for biological sequence comparison, Proc. Natl. Acad. Apr. 1988, vol. 85, No. 8, pp. 2444-2448.
Pokrovsky, V.I., "Small Medical Encyclopedia," Medicine, 1996, V5, pp. 90-96, and English translation of relevant portion, 12 pages.
Robinson, R. P. et al., "Discovery of the Hemifumarate and (α-L-Alanyloxy)methyl Ether as Prodrugs of an Antirheumatic Oxindole: Prodrugs for the Enolic OH Group," J. Med. Chem., 39:10-18 (1996).
Saulnier, M. G. et al., "An Efficient Method for the Synthesis of Guanidino Prodrugs," Bioorganic & Medicinal Chemistry Letters, 4(16):1985-1990 (1994).
Scher, H. I. et al., "Trial Design and Objectives for Castration-Resistant Prostate Cancer: Updated Recommendations From the Prostate Cancer Clinical Trials Working Group 3," Journal of Clinical Oncology, 34(12):1402-1418 (2016).
Sonkin, D. et al., "Are neuroendocrine negative small cell lung cancer and large cell neuroendocrine carcinoma with WT RB1 two faces of the same entity?" Lung Cancer Manag. (2019) 8(2), LMT13, 5 pages.
Tošovská, P. et al., "Oligooxopiperazines as Nonpeptidic α-Helix Mimetics," Organic Letters, 12(7):1588-1591 (2010).
Tornesello, M. L. et al., "Human Oncoviruses and p53 Tumor Suppressor Pathway Deregulation at the Origin of Human Cancers," Cancers, 10, 213 (2018); doi:10.3390/cancers10070213, 14 pages.
Wikenheiser-Brokamp, K. A., "Rb family proteins differentially regulate distinct cell lineages during epithelial development," Development. Sep. 2004;131(17):4299-310. doi: 10.1242/dev.01232. Epub Aug. 4, 2004.
Witzkiewicz, A. K. et al., "The meaning of p16ink4a expression in tumors," Cell Cycle, 10:15, 2497-2503, 2011. doi: 10.4161/cc.10.15.16776.
Wright, P. E. & Dyson, H. J., "Intrinsically disordered proteins in cellular signalling and regulation," Nat Rev Mol Cell Biol., 16(1):18-29 (2015).
Xie, X. et al., "Targeting HPV16 E6-p300 interaction reactivates p53 and inhibits the tumorigenicity of HPV-positive head and neck squamous cell carcinoma," Oncogene, 33(8):1037-1046 (2014).
Yuan, W. L. & Giordano, A., "Acetyltransferase machinery conserved in p300/CBP-family proteins," Oncogene, 21:2253-2260 (2002).

22Rv1 prostate cancer CDX

NCI-H69 small cell lung cancer CDX

SNU-5 gastric cancer CDX

SNU-5 gastric cancer CDX

SNU-16 gastric cancer CDX

NCI-H69 small cell lung cancer CDX

22Rv1 prostate cancer CDX

NCI-H660 prostate cancer CDX

OXOPIPERAZINE DERIVATIVES FOR THE TREATMENT OF CANCER

RELATED APPLICATIONS

This application is a U.S. National Stage Application under 35 U.S.C. § 371 of International Application No. PCT/EP2021/066611, filed Jun. 18, 2021, which claims priority to, and the benefit of, U.S. Provisional Application No. 63/041,416, filed on Jun. 19, 2020, the contents each of which are incorporated herein by reference in their entireties.

BACKGROUND

Despite the ever increasing number of cancer therapies in general, and combination cancer therapies in particular, cancer is still the third most common cause of death worldwide after cardiovascular diseases and infectious/parasitic diseases; in absolute numbers, this corresponds to 7.6 million deaths (ca. 13% of all deaths) in any given year. The World Health Organization (WHO) estimates deaths due to cancer to increase to 13.1 million by 2030, while the American Cancer Society expects over 1,685,210 new cancer cases diagnosed and 595,690 cancer deaths in the U.S. in 2016. A 2012 survey by McMillan Cancer Support in the U.K. has revealed that the median survival time of cancer patients overall has increased from one year to six years since the 1970s. However, for many cancers, median survival has barely improved, remaining less than one year. These statistics illustrate the fact that cancer remains a critical health condition and that there is an urgent need for new anticancer drugs and diagnostic methods to determine the susceptibility of cancers to these drugs.

SUMMARY

In one aspect, the present disclosure provides a method of treating a cancer comprising administering Compound 1:

(Compound 1)

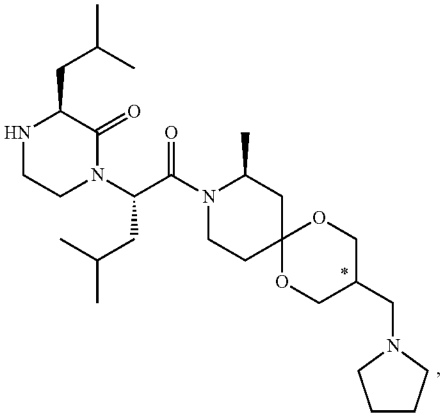

or a pharmaceutically acceptable salt, hydrate, solvate, or stereoisomer thereof, to a subject in need thereof at a dosage disclosed herein.

In one aspect, the present disclosure provides a method of treating a cancer comprising administering Compound 1, to a subject in need thereof at a dosage disclosed herein.

In one aspect, the present disclosure provides a method of treating a cancer comprising administering a composition comprising Compound 1, or a pharmaceutically acceptable salt, hydrate, solvate, or stereoisomer thereof, to a subject in need thereof at a dosage disclosed herein.

In some embodiments of the methods of the disclosure, the subject is a human.

In some embodiments of the methods of the disclosure, the cancer comprises a liquid tumor or a solid tumor.

In some embodiments of the methods of the disclosure, cells of the cancer express p300 and/or CBP.

In some embodiments of the methods of the disclosure, cells of the cancer have lost expression or function of p53, Rb, or a combination thereof.

In some embodiments of the methods of the disclosure, the cancer is Stage II, Stage III, or Stage IV cancer. In some embodiments, the cancer comprises metastatic cancer.

In some embodiments of the methods of the disclosure, the cancer comprises prostate cancer, renal cancer, pancreatic cancer, liver cancer, breast cancer, gastric cancer, colon cancer, cervical cancer, ovarian cancer, head-and-neck cancer, esophageal cancer, hematological cancer, brain cancer, stomach cancer, cancer of the central nervous system, or skin cancer. In some embodiments, the cancer comprises lung cancer (including but not limited to small cell and non-small cell lung cancer), gastric cancer, prostate cancer, breast cancer, hematological cancer, or colon cancer. In some embodiments, the hematological cancer comprises wherein the hematological cancer is acute lymphocytic leukemia (ALL), acute myeloid leukemia (AML), B cell lymphoma (BCL), chronic lymphocytic leukemia (CLL), chronic myeloid leukemia (CML), diffuse large B cell lymphoma (DLBCL), Epstein Barr driven hematological cancer, multiple myeloma (MM), T cell lymphoma (TCL), Hodgkin's lymphoma, or non-Hodgkin's lymphoma.

In some embodiments of the methods of the disclosure, the cancer comprises prostate cancer. In some embodiments, the prostate cancer comprises castrate resistant prostate cancer (CRPC). In some embodiments, the prostate cancer is neuroendocrine prostate cancer (NEPC). In some embodiments, the prostate cancer is resistant to Androgen receptor (AR) pathway inhibitors. In some embodiments, the AR pathway inhibitors comprise abiraterone acetate, enzalutamide, apalutamide, darolutamide, or bicalutamide. In some embodiments, the prostate cancer is androgen driven, AR positive adenocarcinoma.

In some embodiments of the methods of the disclosure, the cancer has relapsed after treatment with a first and/or second line therapy.

In some embodiments of the methods of the disclosure, the cancer has been unresponsive, or only partially responsive, to a first and/or second line therapy.

In some embodiments of the methods of the disclosure, administering the compound slows or stops tumor progression. In some embodiments, slowing or stopping tumor progression comprises inducing senescence of tumor cells. In some embodiments, administering the compound reduces tumor size. In some embodiments, reducing tumor size comprises inducing apoptosis of tumor cells.

In one aspect, the present disclosure provides a composition comprising Compound 1, or a pharmaceutically acceptable salt, hydrate, solvate, or stereoisomer thereof, for use in treating a cancer in a subject in need thereof at a dosage disclosed herein.

In one aspect, the present disclosure provides Compound 1 for use in treating a cancer in a subject in need thereof at a dosage disclosed herein.

In one aspect, the present disclosure provides Compound 1, or a pharmaceutically acceptable salt, hydrate, solvate, or stereoisomer thereof, for use in treating a cancer in a subject in need thereof at a dosage disclosed herein.

In one aspect, described herein is use of a composition (e.g., a composition comprising Compound 1, or a pharmaceutically acceptable salt, hydrate, solvate, or stereoisomer thereof) in the manufacture of a medicament for the treatment of a cancer in a subject in need thereof at a dosage disclosed herein.

In one aspect, described herein is use of Compound 1 or a pharmaceutically acceptable salt, hydrate, solvate, or stereoisomer thereof, in the manufacture of a medicament for the treatment of a cancer in a subject in need thereof at a dosage disclosed herein.

In one aspect, described herein is use of Compound 1 in the manufacture of a medicament for the treatment of a cancer in a subject in need thereof at a dosage disclosed herein.

In one aspect, the present disclosure provides Compound 1':

(Compound 1')

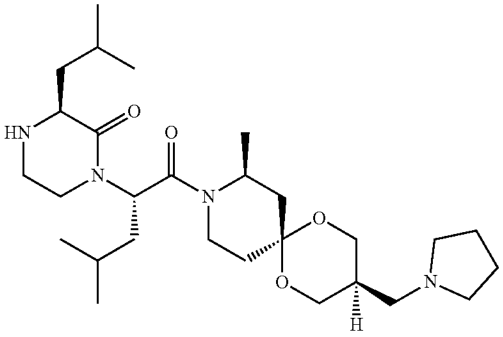

, or a pharmaceutically acceptable salt, hydrate, solvate, or stereoisomer thereof.

In one aspect, the present disclosure provides a method of treating a cancer comprising administering Compound 1':

(Compound 1')

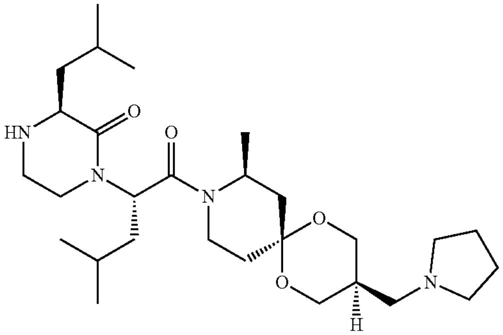

, or a pharmaceutically acceptable salt, hydrate, solvate, or stereoisomer thereof, to a subject in need thereof at a dosage disclosed herein.

In one aspect, the present disclosure provides Compound 1' or a pharmaceutically acceptable salt, hydrate, solvate, or stereoisomer thereof, for use in treating a cancer in a subject in need thereof at a dosage disclosed herein.

In one aspect, described herein is use of a composition (e.g., a composition comprising Compound 1', or a pharmaceutically acceptable salt, hydrate, solvate, or stereoisomer thereof) in the manufacture of a medicament for the treatment of a cancer in a subject in need thereof at a dosage disclosed herein.

In one aspect, described herein is use of Compound 1' or a pharmaceutically acceptable salt, hydrate, solvate, or stereoisomer thereof, in the manufacture of a medicament for the treatment of a cancer in a subject in need thereof at a dosage disclosed herein.

In one aspect, described herein is use of Compound 1' in the manufacture of a medicament for the treatment of a cancer in a subject in need thereof at a dosage disclosed herein.

DETAILED DESCRIPTION

Figure 1:
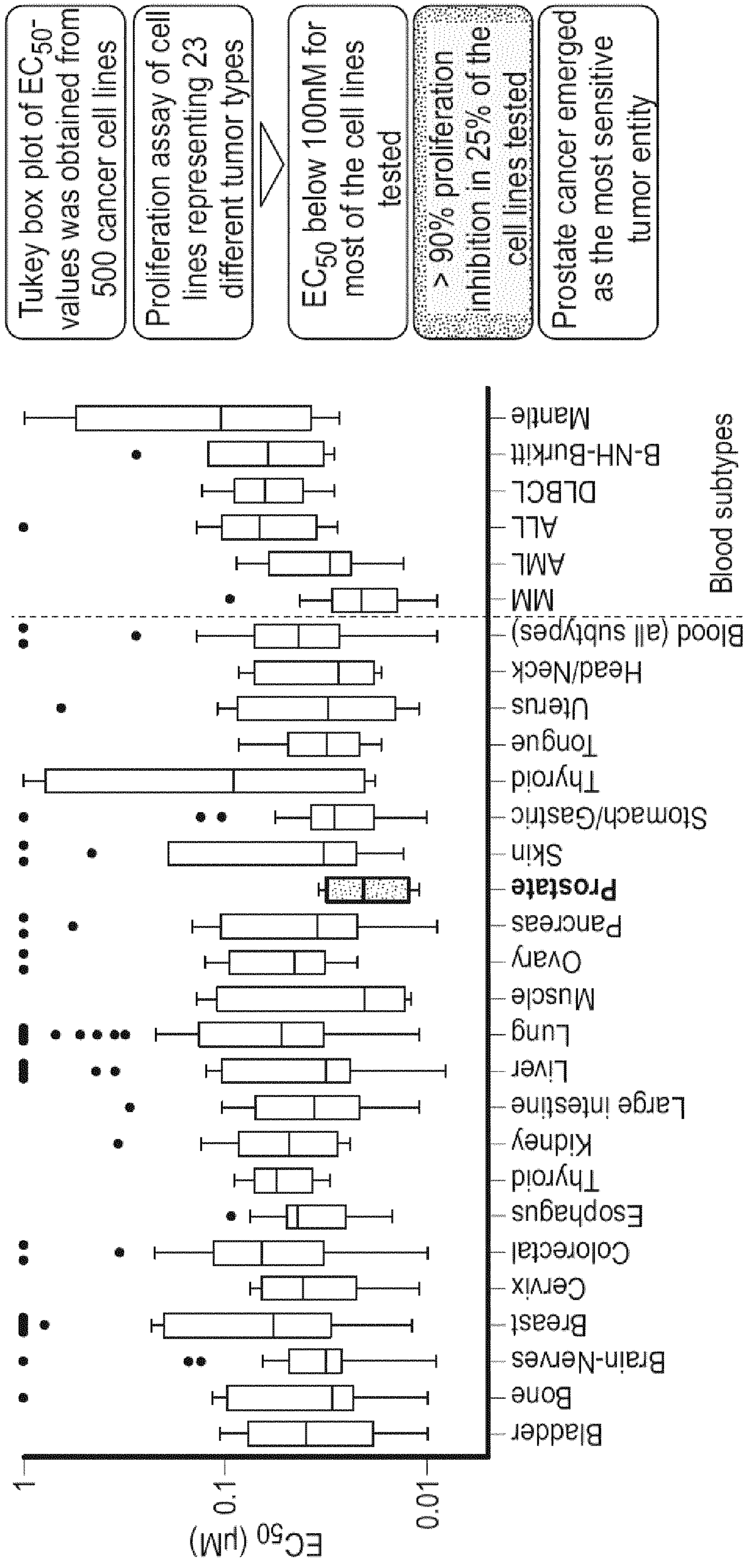
FIG. 1 shows the $EC_{50}$ for antiproliferative assays in several cancer cell lines Proliferation assays were performed in cells after five day treatment with Compound 1.

Dysregulation of the cellular transcription machinery is a fundamental feature of cancer. E1A binding protein (p300) and CREB binding protein (CBP) are two closely related paralog transcriptional co-activators involved in the expression of oncogenic drivers in cancer cells (Attar and Kurdistani, in Cold Spring Harbor Perspectives in Medicine 7:a026534 (2017)), and are thus therapeutic targets for the treatment of cancer.

CBP/p300 interact through their conserved domains with hundreds of proteins. CBP/p300 can act synergistically or antagonistically with other proteins, and modulate downstream biological processes in a highly context-dependent manner to promote either apoptosis or cell proliferation. These domains include the nuclear receptor interaction domain (RID), the cysteine/histidine-rich regions CH1 (TAZ1) and CH3 (TAZ2) domains, the CREB and MYB interaction domain (KIX), Bromodomain, the plant homeodomain (PHD), the histone acetyltransferase and/or lysine acetyltransferase domain (KAT/HAT), the ZZ type zinc finger domain (ZZ), and the interferon response binding domain (IBiD (NCBD)).

The following examples (from Dancy and Cole in Chemical Reviews 115(6):2419 (2015)) demonstrate the context-dependency of gene expression regulation by p300/CBP. For instance, Hottiger and co-workers (in EMBO Journal 17, 3124 (1998)) showed that HIV gene expression could be upregulated by tumor-necrosis factor alpha through binding of the RelA subunit of NFκB to p300/CBP-CH1 but was repressed through interferon-alpha-mediated binding of STAT2 to the same motif p53 binding to p300/CBP/CH3, and consequent induction of p53-dependent genes, results in cell cycle arrest (e.g., as a consequence of genotoxic insults), but apoptosis is induced when overexpressed E2F-1 is bound to p300/CBP/CH3. Cyclic-AMP response is both induced and repressed by p300/CBP via CREB binding to the KIX domain, respectively S6 kinase pp90RSK binding to the CH3 domain.

Modulation of cancer-relevant pathways by p300/CBP include hormone-dependent androgen receptor signaling in prostate cancer; the HIF-1 alpha/VEGF pathway in hypoxia-dependent tumor growth; and the interaction with tumor suppressor p53 and HPV-E6 oncoprotein in HPV-positive carcinomas.

P300 and CBP also play an important role in hematopoiesis and control processes whose disruption can lead to the development of leukemias and lymphomas.

Taken together, these studies highlight how indispensable CBP/p300 is to many cellular signaling pathways, and how p300 and CBP utilize their protein-protein interactions to determine how the cell responds to environmental stimuli. This makes CBP/p300 a target for the development of novel cancer therapies.

The instant disclosure provides that dysfunction of the tumor protein p53 (p53) and/or Retinoblastoma (Rb, also called RB transcriptional corepressor 1, or Rb1) signaling pathway(s) is associated with cancer cell susceptibility to the compounds described herein. Without wishing to be bound by theory, the compound of the present disclosure (e.g., Compound 1) is able to modulate the activity of specific domains, and specific functions of CBP/p300 in a modular fashion. Compound 1 can affect specific domains and activities of CBP/p300 while not affecting, or only minimally affecting, other domains and functions of CBP/p300. As one example, and without wishing to be bound by theory, Compound 1 is able to modulate functions mediated by the N-terminal portion of CBP/p300 (comprising the CH1 domain) without affecting, or only minimally affecting, functions mediated by other domains such as the histone acetyltransferase (HAT) domain. Exemplary functions mediated by the N-terminal portion of CBP/p300 that can be modulated by Compound 1 include, but are not limited to, interaction with DNA damage repair (DDR) proteins such as ATR, NBS1 and PARP1.

p53 and Rb are tumor suppressors that are central to two regulatory pathways critical for the progression of cancer in cells. The p53 pathway plays a role in the regulation cell cycle progression, apoptosis, and genome stability. In the p53 pathway, upstream signals, such as DNA damage or stress, induce P14ARF (encoded by the CDKN2A locus, also called ARF and p14), which increases p53 activity by sequestering the MDM2 proto-oncogene (MDM2), a p53-specific E3 ubiquitin ligase. MDM2, in the absence of these signals, promotes p53 degradation via ubiquitination. p53 can activate DNA repair mechanisms in cells that have sustained DNA damage and arrest the cell cycle at the G1/S phase transition in response to DNA damage.

p53 also plays a role in the initiation of apoptosis. p53 target genes include CDKN1A (also called cyclin dependent kinase inhibitor 1A, or WAF1, or p21), an inhibitor of cyclin dependent kinases (CDKs) that regulates the cell cycle, and BAX (BCL2 associated X, apoptosis regulator), which promotes apoptosis. Thus, loss or dysregulation of p53 signaling allows cancer cells to evade normal cell cycle controls and pro-apoptotic signaling that would halt cancer progression.

In the Rb pathway, elevated expression of P16INK4A (also called P16, and INK4) is a potent mechanism for inhibiting proliferation, and is dominant to a variety of mitogenic and oncogenic signals (Cell Cycle 10:15, 2497-2503; 2011). P16INK4A inhibits CDKs that phosphorylate, and therefore inactivate, Rb1 during the G1 phase of the cell cycle. Rb1 also controls the expression of numerous genes, for example by recruiting transcription factors and chromatin remodeling proteins. Without wishing to be bound by theory, the anti-proliferative effects of the CBP/p300 functional modulator of the instant disclosure (e.g., Compound 1) may be influenced by the function of the p53 and Rb pathways in cancer cells. Without wishing to be bound by theory, treatment of cancer cells with the CBP/p300 modulator described herein can interfere with regulation of CBP/p300 target genes, resulting in cell cycle checkpoint failure at the G1/S phase transition. In some cases, such as in cancer cells with an intact p53 and/or Rb pathway, treatment with CBP/p300 modulators can cause G1 arrest, and cancer cells become senescent, slowing or halting cancer progression. In other cases, such as when the p53 and Rb pathways are not intact, treatment with CBP/p300 modulators can cause catastrophic failure of cell cycle progression during S phase, apoptosis, and cancer regression.

Without wishing to be bound by theory, one mechanism by which the CBP/p300 modulators of the disclosure cause catastrophic failure of cell cycle progression during S phase, cell death (including but not limited to apoptotic cell death), and regression in cancers with defective p53 and Rb pathways is through the interaction between CBP/p300 inhibition and replication stress. p300/CBP is an important component of the DNA replication and DNA damage repair (DDR) complexes, and interacts with several proteins involved in the cellular DDR machinery. The CBP/p300 modulators of the disclosure are able to induce synthetic lethality in the context of p53 and Rb loss. At the replication fork, the N terminal region of p300, which includes the CH1 domain, interacts with DNA damage repair (DDR) proteins such as ATR. This N terminal region also interacts with additional DDR proteins, such as NBS1 and PARP1. This region is targeted by Compound 1. In tumor cells, the combined loss of Rb and p53 function promotes unrestricted proliferation, causes loss of G1/S cell cycle checkpoint controls and high levels of replication stress. Without wishing to be bound by theory, exposure of Rb- and p53-deficient tumor cells to Compound 1 may cause an increase in DNA damage and accumulation of cells in S-phase, and is thought to abrogate further cell cycle checkpoints. It is hypothesized that binding of Compound 1 to the region of p300 including the CH1 target domain interferes with the association of DDR proteins with p300. The S/G2 checkpoint may, potentially, be deregulated through the interference with the p300/ATR interaction by Compound 1.

Cancer cells lacking both Rb and p53 function exhibit compromised G1/S checkpoint control and are particularly vulnerable to replication stress. In the absence of an intact G1/S checkpoint in these cancers, Compound 1 can induce deceleration of S-phase, accumulation of DNA damage and premature entry into mitosis followed by mitotic catastrophe. Loss of Rb and p53 function is thus predictive for an apoptotic response to treatment with the Compound 1.

In vitro testing indicates that Compound 1 can be safely administered in vivo. Compound 1 was tested using in vitro safety pharmacology panels encompassing human enzymes, transporters, kinases, receptors and ion channels thought to be potential contributors to adverse drug reactions. No significant responses were detected to Compound 1.

In vitro testing also supports the use of mouse, Beagle dog, and cynomolgus monkey models to assay dosing and effectiveness of Compound 1. Compound 1 showed similar clearance by hepatocytes in vitro, when assayed using hepatocytes from mouse, dog, and monkey. The metabolic profiles of hepatocytes from mouse, dog, and monkey that were cultured with Compound 1 were assessed. Similarly, the metabolic stability of Compound 1 was assayed in vitro using intestinal microsomes from mouse, rat, dog, monkey, and humans. While Compound 1 had lower stability in intestinal microsomes from monkey compared to human, this result is consistent with the known differences between human and monkey in the activity of intestinal enzymes thought to contribute to the metabolism of Compound 1. All results indicated that mouse, dog and monkey are suitable animal models for evaluating Compound 1.

In some embodiments, the present disclosure provides a method of treating or preventing a cancer, comprising administering to a subject in need thereof Compound 1:

(Compound 1)

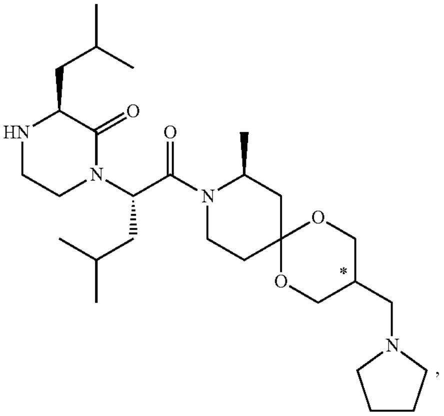

or a pharmaceutically acceptable salt, hydrate, solvate or stereoisomer thereof, at a dosage from about 0.01 mg/kg to about 60 mg/kg.

In some embodiments, Compound 1 is a methanesulfonic acid salt (mesylate).

In some embodiments, Compound 1 is Compound 1':

(Compound 1')

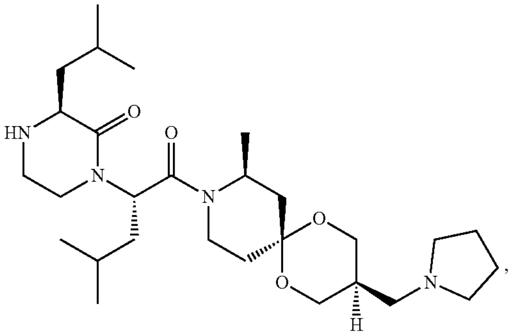

or a pharmaceutically acceptable salt, hydrate, solvate or stereoisomer thereof.

In some embodiments, Compound 1' is a methanesulfonic acid salt (mesylate).

In some embodiments, the present disclosure provides a method of treating a cancer comprising administering to a subject in need thereof Compound 1, or a pharmaceutically acceptable salt, hydrate, solvate or stereoisomer thereof, at a dosage from about 0.01 mg/kg to about 60 mg/kg.

In some embodiments, the present disclosure provides a method of treating or preventing a cancer comprising administering to a subject in need thereof Compound 1 at a dosage from about 0.01 mg/kg to about 60 mg/kg.

In some embodiments, the present disclosure provides a method of treating a cancer comprising administering to a subject in need thereof Compound 1 at a dosage from about 0.01 mg/kg to about 60 mg/kg.

In some embodiments, the present disclosure provides a method of treating or preventing a cancer comprising administering to a subject in need thereof a composition comprising Compound 1, or a pharmaceutically acceptable salt, hydrate, solvate or stereoisomer thereof, at a dosage from about 0.01 mg/kg to about 60 mg/kg.

In some embodiments, the present disclosure provides a method of treating a cancer comprising administering to a subject in need thereof a composition comprising Compound 1, or a pharmaceutically acceptable salt, hydrate, solvate or stereoisomer thereof, at a dosage from about 0.01 mg/kg to about 60 mg/kg.

In some embodiments, the present disclosure provides a composition comprising Compound 1, or a pharmaceutically acceptable salt, hydrate, solvate or stereoisomer thereof, for use in treating or preventing a cancer in a subject in need thereof at a dosage from about 0.01 mg/kg to about 60 mg/kg.

In some embodiments, the present disclosure provides a composition comprising Compound 1, or a pharmaceutically acceptable salt, hydrate, solvate or stereoisomer thereof, for use in treating a cancer in a subject in need thereof at a dosage from about 0.01 mg/kg to about 60 mg/kg.

In some embodiments, the present disclosure provides Compound 1, or a pharmaceutically acceptable salt, hydrate, solvate or stereoisomer thereof, for use in treating or preventing a cancer in a subject in need thereof at a dosage from about 0.01 mg/kg to about 60 mg/kg.

In some embodiments, the present disclosure provides Compound 1, or a pharmaceutically acceptable salt, hydrate, solvate or stereoisomer thereof, for use in treating a cancer in a subject in need thereof at a dosage from about 0.01 mg/kg to about 60 mg/kg.

In some embodiments, the present disclosure provides Compound 1 for use in treating or preventing a cancer in a subject in need thereof at a dosage from about 0.01 mg/kg to about 60 mg/kg.

In some embodiments, the present disclosure provides Compound 1 for use in treating a cancer in a subject in need thereof at a dosage from about 0.01 mg/kg to about 60 mg/kg.

In some embodiments, the present disclosure provides use of a composition comprising Compound 1, or a pharmaceutically acceptable salt, hydrate, solvate or stereoisomer thereof, for the treatment or prevention of a cancer in a subject in need thereof at a dosage from about 0.01 mg/kg to about 60 mg/kg.

In some embodiments, the present disclosure provides use of a composition comprising Compound 1, or a pharmaceutically acceptable salt, hydrate, solvate or stereoisomer thereof, for the treatment of a cancer in a subject in need thereof at a dosage from about 0.01 mg/kg to about 60 mg/kg.

In some embodiments, the present disclosure provides use of Compound 1, or a pharmaceutically acceptable salt, hydrate, solvate or stereoisomer thereof, for the treatment or prevention of a cancer in a subject in need thereof at a dosage from about 0.01 mg/kg to about 60 mg/kg.

In some embodiments, the present disclosure provides use of Compound 1, or a pharmaceutically acceptable salt, hydrate, solvate or stereoisomer thereof, for the treatment of a cancer in a subject in need thereof at a dosage from about 0.01 mg/kg to about 60 mg/kg.

In some embodiments, the present disclosure provides use of Compound 1 for the treatment or prevention of a cancer in a subject in need thereof at a dosage from about 0.01 mg/kg to about 60 mg/kg.

In some embodiments, the present disclosure provides use of Compound 1 for the treatment of a cancer in a subject in need thereof at a dosage from about 0.01 mg/kg to about 60 mg/kg.

In some embodiments, the present disclosure provides use of a composition comprising Compound 1, or a pharmaceutically acceptable salt, hydrate, solvate or stereoisomer thereof, in the manufacture of a medicament for the treatment or prevention of a cancer in a subject in need thereof at a dosage from about 0.01 mg/kg to about 60 mg/kg.

In some embodiments, the present disclosure provides use of a composition comprising Compound 1, or a pharmaceutically acceptable salt, hydrate, solvate or stereoisomer thereof, in the manufacture of a medicament for the treatment of a cancer in a subject in need thereof at a dosage from about 0.01 mg/kg to about 60 mg/kg.

In some embodiments, the present disclosure provides the use of Compound 1, or a pharmaceutically acceptable salt, hydrate, solvate or stereoisomer thereof, in the manufacture of a medicament for the treatment or prevention of a cancer in a subject in need thereof at a dosage from about 0.01 mg/kg to about 60 mg/kg.

In some embodiments, the present disclosure provides the use of Compound 1, or a pharmaceutically acceptable salt, hydrate, solvate or stereoisomer thereof, in the manufacture of a medicament for the treatment of a cancer in a subject in need thereof at a dosage from about 0.01 mg/kg to about 60 mg/kg.

In some embodiments, the present disclosure provides the use of Compound 1 in the manufacture of a medicament for the treatment or prevention of a cancer in a subject in need thereof at a dosage from about 0.01 mg/kg to about 60 mg/kg.

In some embodiments, the present disclosure provides the use of Compound 1 in the manufacture of a medicament for the treatment of a cancer in a subject in need thereof at a dosage from about 0.01 mg/kg to about 60 mg/kg.

In some embodiments, Compound 1 is administered followed by a dosing holiday. In some embodiments, the dosing holiday is followed by resuming administration of Compound 1.

In some embodiments, the dosing holiday is followed by resuming administration of Compound 1 at a different dosing regimen as compared to the administration before the dosing holiday.

In some embodiments, the dosing holiday is followed by resuming administration of Compound 1 at the same dosing regimen as compared to the administration before the dosing holiday.

In some embodiments, the dosing holiday is followed by resuming administration of Compound 1 at a lower dosage as compared to the administration before the dosing holiday.

In some embodiments, the dosing holiday is followed by resuming administration of Compound 1 at a higher dosage as compared to the administration before the dosing holiday.

In some embodiments, the dosing holiday is followed by resuming administration of Compound 1 at about the same dosage as compared to the administration before the dosing holiday.

In some embodiments, the dosing holiday is followed by resuming administration of Compound 1 at the same dosage as compared to the administration before the dosing holiday.

In some embodiments, the dosing holiday is followed by resuming administration of Compound 1 at a lower frequency of administration as compared to the administration before the dosing holiday.

In some embodiments, the dosing holiday is followed by resuming administration of Compound 1 at a higher frequency of administration as compared to the administration before the dosing holiday.

In some embodiments, the dosing holiday is followed by resuming administration of Compound 1 at about the same frequency of administration as compared to the administration before the dosing holiday.

In some embodiments, the dosing holiday is followed by resuming administration of Compound 1 at the same frequency of administration as compared to the administration before the dosing holiday.

In some embodiments, the administration of Compound 1 comprises a dosing holiday.

In some embodiments, the administration of Compound 1 comprises at least one dosing holiday. In some embodiments, the administration of Compound 1 comprises at least two dosing holidays. In some embodiments, the administration of Compound 1 comprises at least three dosing holidays. In some embodiments, the administration of Compound 1 comprises at least four dosing holidays. In some embodiments, the administration of Compound 1 comprises at least five dosing holidays. In some embodiments, the administration of Compound 1 comprises at least six dosing holidays. In some embodiments, the administration of Compound 1 comprises at least seven dosing holidays. In some embodiments, the administration of Compound 1 comprises at least eight dosing holidays. In some embodiments, the administration of Compound 1 comprises at least nine dosing holidays. In some embodiments, the administration of Compound 1 comprises at least ten dosing holidays.

In some embodiments, the administration of Compound 1 comprises one dosing holiday. In some embodiments, the administration of Compound 1 comprises two dosing holidays. In some embodiments, the administration of Compound 1 comprises three dosing holidays. In some embodiments, the administration of Compound 1 comprises four dosing holidays. In some embodiments, the administration of Compound 1 comprises five dosing holidays. In some embodiments, the administration of Compound 1 comprises six dosing holidays. In some embodiments, the administration of Compound 1 comprises seven dosing holidays. In some embodiments, the administration of Compound 1 comprises eight dosing holidays. In some embodiments, the administration of Compound 1 comprises nine dosing holidays. In some embodiments, the administration of Compound 1 comprises ten dosing holidays.

In some embodiments, Compound 1 is administered at a dosage from about 0.01 mg/kg to about 60 mg/kg once every seven days.

In some embodiments, Compound 1 is administered at a dosage from about 0.01 mg/kg to about 60 mg/kg once every seven days for one week.

In some embodiments, Compound 1 is administered at a dosage from about 0.01 mg/kg to about 60 mg/kg once every seven days for two weeks.

In some embodiments, Compound 1 is administered at a dosage from about 0.01 mg/kg to about 60 mg/kg once every seven days for three weeks.

In some embodiments, Compound 1 is administered at a dosage from about 0.01 mg/kg to about 60 mg/kg once every seven days for four weeks.

In some embodiments, Compound 1 is administered at a dosage from about 0.01 mg/kg to about 60 mg/kg once every seven days for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

In some embodiments, Compound 1 is administered at a dosage from about 0.01 mg/kg to about 60 mg/kg once every seven days followed by a dosing holiday.

In some embodiments, Compound 1 is administered at a dosage from about 0.01 mg/kg to about 60 mg/kg once every seven days followed by a one week dosing holiday, a two week dosing holiday, a three week dosing holiday, a four week dosing holiday, a six week dosing holiday, an eight week dosing holiday, a 10 week dosing holiday, a 12 week dosing holiday, a 14 week dosing holiday, a 16 week dosing holiday, an 18 week dosing holiday, a 20 week dosing holiday, a 22 week dosing holiday, a 24 week dosing holiday, a 28 week dosing holiday, a 32 week dosing holiday, a 36 week dosing holiday, a 40 week dosing holiday, a 44 week dosing holiday, a 48 week dosing holiday, or a 52 week dosing holiday.

In some embodiments, Compound 1 is administered at a dosage from about 0.01 mg/kg to about 60 mg/kg once every seven days followed by a dosing holiday, wherein the dosing holiday is followed by resuming administration of Compound 1 at a different dosing regimen as compared to the administration before the dosing holiday.

In some embodiments, Compound 1 is administered at a dosage from about 0.01 mg/kg to about 60 mg/kg once every seven days followed by a dosing holiday, wherein the dosing holiday is followed by resuming administration of Compound 1 at the same dosing regimen as compared to the administration before the dosing holiday.

In some embodiments, Compound 1 is administered at a dosage from about 0.01 mg/kg to about 60 mg/kg once every seven days followed by a dosing holiday, wherein the dosing holiday is followed by resuming administration of Compound 1 at a dosage from about 0.01 mg/kg to about 60 mg/kg once every seven days.

In some embodiments, Compound 1 is administered at a dosage from about 0.1 mg/kg to about 55 mg/kg, about 0.2 mg/kg to about 50 mg/kg, about 0.4 mg/kg to about 45 mg/kg, about 0.6 mg/kg to about 40 mg/kg, about 0.8 mg/kg to about 35 mg/kg, about 1 mg/kg to about 30 mg/kg, about 1.5 mg/kg to about 25 mg/kg, about 2 mg/kg to about 20 mg/kg, about 3 mg/kg to about 18 mg/kg, about 4 mg/kg to about 16 mg/kg, about 5 mg/kg to about 15 mg/kg, about 6 mg/kg to about 14 mg/kg, about 7 mg/kg to about 13 mg/kg, about 8 mg/kg to about 12 mg/kg, about 9 mg/kg to about 11 mg/kg, or about 9 mg/kg to about 10 mg/kg.

In some embodiments, Compound 1 is administered at a dosage from about 0.01 mg/kg to about 60 mg/kg, about 0.01 mg/kg to about 55 mg/kg, about 0.01 mg/kg to about 50 mg/kg, about 0.01 mg/kg to about 45 mg/kg, about 0.01 mg/kg to about 40 mg/kg, about 0.01 mg/kg to about 35 mg/kg, about 0.01 mg/kg to about 30 mg/kg, about 0.01 mg/kg to about 25 mg/kg, about 0.01 mg/kg to about 20 mg/kg, about 0.01 mg/kg to about 15 mg/kg, about 0.01 mg/kg to about 12 mg/kg, about 0.01 mg/kg to about 10 mg/kg, about 0.01 mg/kg to about 8 mg/kg, about 0.01 mg/kg to about 6 mg/kg, about 0.01 mg/kg to about 5 mg/kg, about 0.01 mg/kg to about 4 mg/kg, about 0.01 mg/kg to about 3 mg/kg, about 0.01 mg/kg to about 2 mg/kg, about 0.01 mg/kg to about 1 mg/kg, about 0.01 mg/kg to about 0.5 mg/kg, or about 0.01 mg/kg to about 0.1 mg/kg.

In some embodiments, Compound 1 is administered at a dosage from about 0.01 mg/kg to about 60 mg/kg, about 0.1 mg/kg to about 60 mg/kg, about 0.5 mg/kg to about 60 mg/kg, about 1 mg/kg to about 60 mg/kg, about 2 mg/kg to about 60 mg/kg, about 3 mg/kg to about 60 mg/kg, about 4 mg/kg to about 60 mg/kg, about 5 mg/kg to about 60 mg/kg, about 6 mg/kg to about 60 mg/kg, about 8 mg/kg to about 60 mg/kg, about 10 mg/kg to about 60 mg/kg, about 12 mg/kg to about 60 mg/kg, about 15 mg/kg to about 60 mg/kg, about 20 mg/kg to about 60 mg/kg, about 25 mg/kg to about 60 mg/kg, about 30 mg/kg to about 60 mg/kg, about 35 mg/kg to about 60 mg/kg, about 40 mg/kg to about 60 mg/kg, about 45 mg/kg to about 60 mg/kg, about 50 mg/kg to about 60 mg/kg, or about 55 mg/kg to about 60 mg/kg.

In some embodiments, Compound 1 is administered at a dosage from about 0.4 mg/kg to about 15 mg/kg.

In some embodiments, Compound 1 is administered at a dosage from about 0.4 mg/kg to about 15 mg/kg once every seven days.

In some embodiments, Compound 1 is administered at a dosage from about 0.4 mg/kg to about 15 mg/kg once every seven days for one week.

In some embodiments, Compound 1 is administered at a dosage from about 0.4 mg/kg to about 15 mg/kg once every seven days for two weeks.

In some embodiments, Compound 1 is administered at a dosage from about 0.4 mg/kg to about 15 mg/kg once every seven days for three weeks.

In some embodiments, Compound 1 is administered at a dosage from about 0.4 mg/kg to about 15 mg/kg once every seven days for four weeks.

In some embodiments, Compound 1 is administered at a dosage from about 0.4 mg/kg to about 15 mg/kg once every seven days for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

In some embodiments, Compound 1 is administered at a dosage from about 0.4 mg/kg to about 15 mg/kg once every seven days followed by a dosing holiday.

In some embodiments, Compound 1 is administered at a dosage from about 0.4 mg/kg to about 15 mg/kg once every seven days followed by a one week dosing holiday, a two week dosing holiday, a three week dosing holiday, a four week dosing holiday, a six week dosing holiday, an eight week dosing holiday, a 10 week dosing holiday, a 12 week dosing holiday, a 14 week dosing holiday, a 16 week dosing holiday, an 18 week dosing holiday, a 20 week dosing holiday, a 22 week dosing holiday, a 24 week dosing holiday, a 28 week dosing holiday, a 32 week dosing holiday, a 36 week dosing holiday, a 40 week dosing holiday, a 44 week dosing holiday, a 48 week dosing holiday, or a 52 week dosing holiday.

In some embodiments, Compound 1 is administered at a dosage from about 0.4 mg/kg to about 15 mg/kg once every seven days followed by a dosing holiday, wherein the dosing holiday is followed by resuming administration of Compound 1 at a different dosing regimen as compared to the administration before the dosing holiday.

In some embodiments, Compound 1 is administered at a dosage from about 0.4 mg/kg to about 15 mg/kg once every seven days followed by a dosing holiday, wherein the dosing holiday is followed by resuming administration of Compound 1 at the same dosing regimen as compared to the administration before the dosing holiday.

In some embodiments, Compound 1 is administered at a dosage from about 0.4 mg/kg to about 15 mg/kg once every seven days followed by a dosing holiday, wherein the dosing holiday is followed by resuming administration of Compound 1 at a dosage from about 0.4 mg/kg to about 15 mg/kg once every seven days.

In some embodiments, Compound 1 is administered at a dosage from about 0.8 mg/kg to about 6 mg/kg.

In some embodiments, Compound 1 is administered at a dosage from about 0.8 mg/kg to about 6 mg/kg once every seven days.

In some embodiments, Compound 1 is administered at a dosage from about 0.8 mg/kg to about 6 mg/kg once every seven days for one week.

In some embodiments, Compound 1 is administered at a dosage from about 0.8 mg/kg to about 6 mg/kg once every seven days for two weeks.

In some embodiments, Compound 1 is administered at a dosage from about 0.8 mg/kg to about 6 mg/kg once every seven days for three weeks.

In some embodiments, Compound 1 is administered at a dosage from about 0.8 mg/kg to about 6 mg/kg once every seven days for four weeks.

In some embodiments, Compound 1 is administered at a dosage from about 0.8 mg/kg to about 6 mg/kg once every seven days for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

In some embodiments, Compound 1 is administered at a dosage from about 0.8 mg/kg to about 6 mg/kg once every seven days followed by a dosing holiday.

In some embodiments, Compound 1 is administered at a dosage from about 0.8 mg/kg to about 6 mg/kg once every seven days followed by a one week dosing holiday, a two week dosing holiday, a three week dosing holiday, a four week dosing holiday, a six week dosing holiday, an eight week dosing holiday, a 10 week dosing holiday, a 12 week dosing holiday, a 14 week dosing holiday, a 16 week dosing holiday, an 18 week dosing holiday, a 20 week dosing holiday, a 22 week dosing holiday, a 24 week dosing holiday, a 28 week dosing holiday, a 32 week dosing holiday, a 36 week dosing holiday, a 40 week dosing holiday, a 44 week dosing holiday, a 48 week dosing holiday, or a 52 week dosing holiday.

In some embodiments, Compound 1 is administered at a dosage from about 0.8 mg/kg to about 6 mg/kg once every seven days followed by a dosing holiday, wherein the dosing holiday is followed by resuming administration of Compound 1 at a different dosing regimen as compared to the administration before the dosing holiday.

In some embodiments, Compound 1 is administered at a dosage from about 0.8 mg/kg to about 6 mg/kg once every seven days followed by a dosing holiday, wherein the dosing holiday is followed by resuming administration of Compound 1 at the same dosing regimen as compared to the administration before the dosing holiday.

In some embodiments, Compound 1 is administered at a dosage from about 0.8 mg/kg to about 6 mg/kg once every seven days followed by a dosing holiday, wherein the dosing holiday is followed by resuming administration of Compound 1 at a dosage from about 0.8 mg/kg to about 6 mg/kg once every seven days.

In some embodiments, Compound 1 is administered at a dosage from about 0.8 mg/kg to about 6 mg/kg, about 0.9 mg/kg to about 5.5 mg/kg, about 1 mg/kg to about 5 mg/kg, about 1.2 mg/kg to about 4.5 mg/kg, about 1.5 mg/kg to about 4 mg/kg, about 2 mg/kg to about 3.5 mg/kg, or about 2.5 mg/kg to about 3 mg/kg.

In some embodiments, Compound 1 is administered at a dosage from about 0.8 mg/kg to about 6 mg/kg, about 0.8 mg/kg to about 5.5 mg/kg, about 0.8 mg/kg to about 5 mg/kg, about 0.8 mg/kg to about 4.5 mg/kg, about 0.8 mg/kg to about 4 mg/kg, about 0.8 mg/kg to about 3.5 mg/kg, about 0.8 mg/kg to about 3 mg/kg, about 0.8 mg/kg to about 2.5 mg/kg, about 0.8 mg/kg to about 2 mg/kg, about 0.8 mg/kg to about 1.5 mg/kg, about 0.8 mg/kg to about 1.2 mg/kg, or about 0.8 mg/kg to about 1 mg/kg.

In some embodiments, Compound 1 is administered at a dosage from about 0.8 mg/kg to about 6 mg/kg, about 1 mg/kg to about 6 mg/kg, about 1.2 mg/kg to about 6 mg/kg, about 1.5 mg/kg to about 6 mg/kg, about 2 mg/kg to about 6 mg/kg, about 2.5 mg/kg to about 6 mg/kg, about 3 mg/kg to about 6 mg/kg, about 3.5 mg/kg to about 6 mg/kg, about 4 mg/kg to about 6 mg/kg, about 4.5 mg/kg to about 6 mg/kg, about 5 mg/kg to about 6 mg/kg, or about 5.5 mg/kg to about 6 mg/kg.

In some embodiments, Compound 1 is administered at a dosage of about 1.2 mg/kg.

In some embodiments, Compound 1 is administered at a dosage of about 1.2 mg/kg once every seven days.

In some embodiments, Compound 1 is administered at a dosage of about 1.2 mg/kg once every seven days for one week.

In some embodiments, Compound 1 is administered at a dosage of about 1.2 mg/kg once every seven days for two weeks.

In some embodiments, Compound 1 is administered at a dosage of about 1.2 mg/kg once every seven days for three weeks.

In some embodiments, Compound 1 is administered at a dosage of about 1.2 mg/kg once every seven days for four weeks.

In some embodiments, Compound 1 is administered at a dosage of about 1.2 mg/kg once every seven days for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

In some embodiments, Compound 1 is administered at a dosage of about 1.2 mg/kg once every seven days followed by a dosing holiday.

In some embodiments, Compound 1 is administered at a dosage of about 1.2 mg/kg once every seven days followed by a one week dosing holiday, a two week dosing holiday, a three week dosing holiday, a four week dosing holiday, a six week dosing holiday, an eight week dosing holiday, a 10 week dosing holiday, a 12 week dosing holiday, a 14 week dosing holiday, a 16 week dosing holiday, an 18 week dosing holiday, a 20 week dosing holiday, a 22 week dosing holiday, a 24 week dosing holiday, a 28 week dosing holiday, a 32 week dosing holiday, a 36 week dosing holiday, a 40 week dosing holiday, a 44 week dosing holiday, a 48 week dosing holiday, or a 52 week dosing holiday.

In some embodiments, Compound 1 is administered at a dosage of about 1.2 mg/kg once every seven days followed by a dosing holiday, wherein the dosing holiday is followed by resuming administration of Compound 1 at a different dosing regimen as compared to the administration before the dosing holiday.

In some embodiments, Compound 1 is administered at a dosage of about 1.2 mg/kg once every seven days followed by a dosing holiday, wherein the dosing holiday is followed by resuming administration of Compound 1 at the same dosing regimen as compared to the administration before the dosing holiday.

In some embodiments, Compound 1 is administered at a dosage of about 1.2 mg/kg once every seven days followed by a dosing holiday, wherein the dosing holiday is followed by resuming administration of Compound 1 at a dosage of about 1.2 mg/kg once every seven days.

In some embodiments, Compound 1 is administered at a dosage of about 1.2±0.5 mg/kg, about 1.2±0.4 mg/kg, about 1.2±0.3 mg/kg, about 1.2±0.2 mg/kg, or about 1.2±0.1 mg/kg.

In some embodiments, Compound 1 is administered at a dosage of about 2.4 mg/kg.

In some embodiments, Compound 1 is administered at a dosage of about 2.4 mg/kg once every seven days.

In some embodiments, Compound 1 is administered at a dosage of about 2.4 mg/kg once every seven days for one week.

In some embodiments, Compound 1 is administered at a dosage of about 2.4 mg/kg once every seven days for two weeks.

In some embodiments, Compound 1 is administered at a dosage of about 2.4 mg/kg once every seven days for three weeks.

In some embodiments, Compound 1 is administered at a dosage of about 2.4 mg/kg once every seven days for four weeks.

In some embodiments, Compound 1 is administered at a dosage of about 2.4 mg/kg once every seven days for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

In some embodiments, Compound 1 is administered at a dosage of about 2.4 mg/kg once every seven days followed by a dosing holiday.

In some embodiments, Compound 1 is administered at a dosage of about 2.4 mg/kg once every seven days followed by a one week dosing holiday, a two week dosing holiday, a three week dosing holiday, a four week dosing holiday, a six week dosing holiday, an eight week dosing holiday, a 10 week dosing holiday, a 12 week dosing holiday, a 14 week dosing holiday, a 16 week dosing holiday, an 18 week dosing holiday, a 20 week dosing holiday, a 22 week dosing holiday, a 24 week dosing holiday, a 28 week dosing holiday, a 32 week dosing holiday, a 36 week dosing holiday, a 40 week dosing holiday, a 44 week dosing holiday, a 48 week dosing holiday, or a 52 week dosing holiday.

In some embodiments, Compound 1 is administered at a dosage of about 2.4 mg/kg once every seven days followed by a dosing holiday, wherein the dosing holiday is followed by resuming administration of Compound 1 at a different dosing regimen as compared to the administration before the dosing holiday.

In some embodiments, Compound 1 is administered at a dosage of about 2.4 mg/kg once every seven days followed by a dosing holiday, wherein the dosing holiday is followed by resuming administration of Compound 1 at the same dosing regimen as compared to the administration before the dosing holiday.

In some embodiments, Compound 1 is administered at a dosage of about 2.4 mg/kg once every seven days followed by a dosing holiday, wherein the dosing holiday is followed by resuming administration of Compound 1 at a dosage of about 2.4 mg/kg once every seven days.

In some embodiments, Compound 1 is administered at a dosage of about 2.4±1 mg/kg, about 2.4±0.9 mg/kg, about 2.4±0.8 mg/kg, about 2.4±0.7 mg/kg, about 2.4±0.6 mg/kg, about 2.4±0.5 mg/kg, about 2.4±0.4 mg/kg, about 2.4±0.3 mg/kg, about 2.4±0.2 mg/kg, or about 2.4±0.1 mg/kg.

In some embodiments, Compound 1 is administered at a dosage of about 4.8 mg/kg.

In some embodiments, Compound 1 is administered at a dosage of about 4.8 mg/kg once every seven days.

In some embodiments, Compound 1 is administered at a dosage of about 4.8 mg/kg once every seven days for one week.

In some embodiments, Compound 1 is administered at a dosage of about 4.8 mg/kg once every seven days for two weeks.

In some embodiments, Compound 1 is administered at a dosage of about 4.8 mg/kg once every seven days for three weeks.

In some embodiments, Compound 1 is administered at a dosage of about 4.8 mg/kg once every seven days for four weeks.

In some embodiments, Compound 1 is administered at a dosage of about 4.8 mg/kg once every seven days for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

In some embodiments, Compound 1 is administered at a dosage of about 4.8 mg/kg once every seven days followed by a dosing holiday.

In some embodiments, Compound 1 is administered at a dosage of about 4.8 mg/kg once every seven days followed by a one week dosing holiday, a two week dosing holiday, a three week dosing holiday, a four week dosing holiday, a six week dosing holiday, an eight week dosing holiday, a 10 week dosing holiday, a 12 week dosing holiday, a 14 week dosing holiday, a 16 week dosing holiday, an 18 week dosing holiday, a 20 week dosing holiday, a 22 week dosing holiday, a 24 week dosing holiday, a 28 week dosing holiday, a 32 week dosing holiday, a 36 week dosing holiday, a 40 week dosing holiday, a 44 week dosing holiday, a 48 week dosing holiday, or a 52 week dosing holiday.

In some embodiments, Compound 1 is administered at a dosage of about 4.8 mg/kg once every seven days followed by a dosing holiday, wherein the dosing holiday is followed by resuming administration of Compound 1 at a different dosing regimen as compared to the administration before the dosing holiday.

In some embodiments, Compound 1 is administered at a dosage of about 4.8 mg/kg once every seven days followed by a dosing holiday, wherein the dosing holiday is followed by resuming administration of Compound 1 at the same dosing regimen as compared to the administration before the dosing holiday.

In some embodiments, Compound 1 is administered at a dosage of about 4.8 mg/kg once every seven days followed by a dosing holiday, wherein the dosing holiday is followed by resuming administration of Compound 1 at a dosage of about 4.8 mg/kg once every seven days.

In some embodiments, Compound 1 is administered at a dosage of about 4.8±1 mg/kg, about 4.8±0.9 mg/kg, about 4.8±0.8 mg/kg, about 4.8±0.7 mg/kg, about 4.8±0.6 mg/kg, about 4.8±0.5 mg/kg, about 4.8±0.4 mg/kg, about 4.8±0.3 mg/kg, about 4.8±0.2 mg/kg, or about 4.8±0.1 mg/kg.

In some embodiments, Compound 1 is administered at a dosage of about 1.2 mg/kg, about 2.4 mg/kg, or about 4.8 mg/kg.

In some embodiments, Compound 1 is administered at a dosage of about 1.2 mg/kg, about 2.4 mg/kg, or about 4.8 mg/kg once every seven days.

In some embodiments, Compound 1 is administered at a dosage of about 1.2 mg/kg, about 2.4 mg/kg, or about 4.8 mg/kg once every seven days for one week.

In some embodiments, Compound 1 is administered at a dosage of about 1.2 mg/kg, about 2.4 mg/kg, or about 4.8 mg/kg once every seven days for two weeks.

In some embodiments, Compound 1 is administered at a dosage of about 1.2 mg/kg, about 2.4 mg/kg, or about 4.8 mg/kg once every seven days for three weeks.

In some embodiments, Compound 1 is administered at a dosage of about 1.2 mg/kg, about 2.4 mg/kg, or about 4.8 mg/kg once every seven days for four weeks.

In some embodiments, Compound 1 is administered at a dosage of about 1.2 mg/kg, about 2.4 mg/kg, or about 4.8 mg/kg once every seven days for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

In some embodiments, Compound 1 is administered at a dosage of about 1.2 mg/kg, about 2.4 mg/kg, or about 4.8 mg/kg once every seven days followed by a dosing holiday.

In some embodiments, Compound 1 is administered at a dosage of about 1.2 mg/kg, about 2.4 mg/kg, or about 4.8 mg/kg once every seven days followed by a one week dosing holiday, a two week dosing holiday, a three week dosing holiday, a four week dosing holiday, a six week dosing holiday, an eight week dosing holiday, a 10 week dosing holiday, a 12 week dosing holiday, a 14 week dosing holiday, a 16 week dosing holiday, an 18 week dosing holiday, a 20 week dosing holiday, a 22 week dosing holiday, a 24 week dosing holiday, a 28 week dosing holiday, a 32 week dosing holiday, a 36 week dosing holiday, a 40 week dosing holiday, a 44 week dosing holiday, a 48 week dosing holiday, or a 52 week dosing holiday.

In some embodiments, Compound 1 is administered at a dosage of about 1.2 mg/kg, about 2.4 mg/kg, or about 4.8 mg/kg once every seven days followed by a dosing holiday, wherein the dosing holiday is followed by resuming administration of Compound 1 at a different dosing regimen as compared to the administration before the dosing holiday.

In some embodiments, Compound 1 is administered at a dosage of about 1.2 mg/kg, about 2.4 mg/kg, or about 4.8 mg/kg once every seven days followed by a dosing holiday, wherein the dosing holiday is followed by resuming administration of Compound 1 at the same dosing regimen as compared to the administration before the dosing holiday.

In some embodiments, Compound 1 is administered at a dosage of about 1.2 mg/kg, about 2.4 mg/kg, or about 4.8 mg/kg once every seven days followed by a dosing holiday, wherein the dosing holiday is followed by resuming administration of Compound 1 at a dosage of about 1.2 mg/kg, about 2.4 mg/kg, or about 4.8 mg/kg once every seven days.

In some embodiments, Compound 1 is administered at a dosage from about 0.08 mg/kg to about 1.2 mg/kg.

In some embodiments, Compound 1 is administered at a dosage from about 0.08 mg/kg to about 1.2 mg/kg once daily for seven days.

In some embodiments, Compound 1 is administered at a dosage from about 0.08 mg/kg to about 1.2 mg/kg once daily for two weeks.

In some embodiments, Compound 1 is administered at a dosage from about 0.08 mg/kg to about 1.2 mg/kg once daily for three weeks.

In some embodiments, Compound 1 is administered at a dosage from about 0.08 mg/kg to about 1.2 mg/kg once daily for four weeks.

In some embodiments, Compound 1 is administered at a dosage from about 0.08 mg/kg to about 1.2 mg/kg once daily for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

In some embodiments, Compound 1 is administered at a dosage from about 0.08 mg/kg to about 1.2 mg/kg once daily for seven days followed by a seven day dosing holiday.

In some embodiments, Compound 1 is administered at a dosage from about 0.08 mg/kg to about 1.2 mg/kg once daily for seven days followed by a one week dosing holiday, a two week dosing holiday, a three week dosing holiday, a four week dosing holiday, a six week dosing holiday, an eight week dosing holiday, a 10 week dosing holiday, a 12 week dosing holiday, a 14 week dosing holiday, a 16 week dosing holiday, an 18 week dosing holiday, a 20 week dosing holiday, a 22 week dosing holiday, a 24 week dosing holiday, a 28 week dosing holiday, a 32 week dosing holiday, a 36 week dosing holiday, a 40 week dosing holiday, a 44 week dosing holiday, a 48 week dosing holiday, or a 52 week dosing holiday.

In some embodiments, Compound 1 is administered at a dosage from about 0.08 mg/kg to about 1.2 mg/kg once daily for seven days followed by a dosing holiday, wherein the dosing holiday is followed by resuming administration of Compound 1 at a different dosing regimen as compared to the administration before the dosing holiday.

In some embodiments, Compound 1 is administered at a dosage from about 0.08 mg/kg to about 1.2 mg/kg once daily for seven days followed by a dosing holiday, wherein the dosing holiday is followed by resuming administration of Compound 1 at the same dosing regimen as compared to the administration before the dosing holiday.

In some embodiments, Compound 1 is administered at a dosage from about 0.08 mg/kg to about 1.2 mg/kg once daily for seven days followed by a dosing holiday, wherein the dosing holiday is followed by resuming administration of Compound 1 at a dosage from about 0.08 mg/kg to about 1.2 mg/kg once daily for seven days.

In some embodiments, Compound 1 is administered at a dosage from about 0.08 mg/kg to about 1.2 mg/kg, about 0.1 mg/kg to about 1 mg/kg, about 0.15 mg/kg to about 0.9 mg/kg, about 0.2 mg/kg to about 0.8 mg/kg, about 0.25 mg/kg to about 0.7 mg/kg, about 0.3 mg/kg to about 0.6 mg/kg, or about 0.4 mg/kg to about 0.5 mg/kg.

In some embodiments, Compound 1 is administered at a dosage from about 0.08 mg/kg to about 1.2 mg/kg, about 0.08 mg/kg to about 1.1 mg/kg, about 0.08 mg/kg to about 1 mg/kg, about 0.08 mg/kg to about 0.9 mg/kg, about 0.08 mg/kg to about 0.8 mg/kg, about 0.08 mg/kg to about 0.7 mg/kg, about 0.08 mg/kg to about 0.6 mg/kg, about 0.08 mg/kg to about 0.5 mg/kg, about 0.08 mg/kg to about 0.4 mg/kg, about 0.08 mg/kg to about 0.3 mg/kg, about 0.08 mg/kg to about 0.2 mg/kg, about 0.08 mg/kg to about 0.1 mg/kg, about 0.08 mg/kg to about 0.8 mg/kg, about 0.08 mg/kg to about 0.6 mg/kg, about 0.08 mg/kg to about 0.4 mg/kg, about 0.08 mg/kg to about 0.2 mg/kg, or about 0.08 mg/kg to about 0.1 mg/kg.

In some embodiments, Compound 1 is administered at a dosage from about 0.08 mg/kg to about 1.2 mg/kg, about 0.1 mg/kg to about 1.2 mg/kg, about 0.2 mg/kg to about 1.2 mg/kg, about 0.3 mg/kg to about 1.2 mg/kg, about 0.4 mg/kg to about 1.2 mg/kg, about 0.5 mg/kg to about 1.2 mg/kg, about 0.6 mg/kg to about 1.2 mg/kg, about 0.7 mg/kg to about 1.2 mg/kg, about 0.8 mg/kg to about 1.2 mg/kg, about 0.9 mg/kg to about 1.2 mg/kg, about 1 mg/kg to about 1.2 mg/kg, or about 1.1 mg/kg to about 1.2 mg/kg.

In some embodiments, Compound 1 is administered at a dosage from about 0.1 mg/kg to about 0.3 mg/kg.

In some embodiments, Compound 1 is administered at a dosage from about 0.1 mg/kg to about 0.3 mg/kg once daily for seven days.

In some embodiments, Compound 1 is administered at a dosage from about 0.1 mg/kg to about 0.3 mg/kg once daily for two weeks.

In some embodiments, Compound 1 is administered at a dosage from about 0.1 mg/kg to about 0.3 mg/kg once daily for three weeks.

In some embodiments, Compound 1 is administered at a dosage from about 0.1 mg/kg to about 0.3 mg/kg once daily for four weeks.

In some embodiments, Compound 1 is administered at a dosage from about 0.1 mg/kg to about 0.3 mg/kg once daily for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

In some embodiments, Compound 1 is administered at a dosage from 0.1 mg/kg to about 0.3 mg/kg once daily for seven days followed by a seven day dosing holiday.

In some embodiments, Compound 1 is administered at a dosage from about 0.1 mg/kg to about 0.3 mg/kg once daily for seven days followed by a one week dosing holiday, a two week dosing holiday, a three week dosing holiday, a four week dosing holiday, a six week dosing holiday, an eight week dosing holiday, a 10 week dosing holiday, a 12 week dosing holiday, a 14 week dosing holiday, a 16 week dosing holiday, an 18 week dosing holiday, a 20 week dosing holiday, a 22 week dosing holiday, a 24 week dosing holiday, a 28 week dosing holiday, a 32 week dosing holiday, a 36 week dosing holiday, a 40 week dosing holiday, a 44 week dosing holiday, a 48 week dosing holiday, or a 52 week dosing holiday.

In some embodiments, Compound 1 is administered at a dosage from about 0.1 mg/kg to about 0.3 mg/kg once daily for seven days followed by a dosing holiday, wherein the dosing holiday is followed by resuming administration of Compound 1 at a different dosing regimen as compared to the administration before the dosing holiday.

In some embodiments, Compound 1 is administered at a dosage from about 0.1 mg/kg to about 0.3 mg/kg once daily for seven days followed by a dosing holiday, wherein the dosing holiday is followed by resuming administration of Compound 1 at the same dosing regimen as compared to the administration before the dosing holiday.

In some embodiments, Compound 1 is administered at a dosage from about 0.1 mg/kg to about 0.3 mg/kg once daily for seven days followed by a dosing holiday, wherein the dosing holiday is followed by resuming administration of Compound 1 at a dosage from about 0.1 mg/kg to about 0.3 mg/kg once daily for seven days.

In some embodiments, Compound 1 is administered at a dosage from about 0.1 mg/kg to about 0.3 mg/kg, about 0.12 mg/kg to about 0.28 mg/kg, about 0.14 mg/kg to about 0.26 mg/kg, about 0.16 mg/kg to about 0.24 mg/kg, about 0.18 mg/kg to about 0.22 mg/kg, about 0.18 mg/kg to about 0.20 mg/kg.

In some embodiments, Compound 1 is administered at a dosage from about 0.1 mg/kg to about 0.3 mg/kg, about 0.1 mg/kg to about 0.28 mg/kg, about 0.1 mg/kg to about 0.26 mg/kg, about 0.1 mg/kg to about 0.24 mg/kg, about 0.1 mg/kg to about 0.22 mg/kg, about 0.1 mg/kg to about 0.2 mg/kg, about 0.1 mg/kg to about 0.18 mg/kg, about 0.1 mg/kg to about 0.16 mg/kg, about 0.1 mg/kg to about 0.14 mg/kg, or about 0.1 mg/kg to about 0.12 mg/kg.

In some embodiments, Compound 1 is administered at a dosage from about 0.1 mg/kg to about 0.3 mg/kg, about 0.12 mg/kg to about 0.3 mg/kg, about 0.14 mg/kg to about 0.3 mg/kg, about 0.16 mg/kg to about 0.3 mg/kg, about 0.18 mg/kg to about 0.3 mg/kg, about 0.2 mg/kg to about 0.3 mg/kg, about 0.22 mg/kg to about 0.3 mg/kg, about 0.24 mg/kg to about 0.3 mg/kg, about 0.26 mg/kg to about 0.3 mg/kg, or about 0.28 mg/kg to about 0.3 mg/kg.

In some embodiments, Compound 1 is administered at a dosage of about 0.12 mg/kg.

In some embodiments, Compound 1 is administered at a dosage of about 0.12 mg/kg once daily for seven days.

In some embodiments, Compound 1 is administered at a dosage of about 0.12 mg/kg once daily for two weeks.

In some embodiments, Compound 1 is administered at a dosage of about 0.12 mg/kg once daily for three weeks.

In some embodiments, Compound 1 is administered at a dosage of about 0.12 mg/kg once daily for four weeks.

In some embodiments, Compound 1 is administered at a dosage of about 0.12 mg/kg once daily for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

In some embodiments, Compound 1 is administered at a dosage of 0.12 mg/kg once daily for seven days followed by a seven day dosing holiday.

In some embodiments, Compound 1 is administered at a dosage of about 0.12 mg/kg once daily for seven days followed by a one week dosing holiday, a two week dosing holiday, a three week dosing holiday, a four week dosing holiday, a six week dosing holiday, an eight week dosing holiday, a 10 week dosing holiday, a 12 week dosing holiday, a 14 week dosing holiday, a 16 week dosing holiday, an 18 week dosing holiday, a 20 week dosing holiday, a 22 week dosing holiday, a 24 week dosing holiday, a 28 week dosing holiday, a 32 week dosing holiday, a 36 week dosing holiday, a 40 week dosing holiday, a 44 week dosing holiday, a 48 week dosing holiday, or a 52 week dosing holiday.

In some embodiments, Compound 1 is administered at a dosage of about 0.12 mg/kg once daily for seven days followed by a dosing holiday, wherein the dosing holiday is followed by resuming administration of Compound 1 at a different dosing regimen as compared to the administration before the dosing holiday.

In some embodiments, Compound 1 is administered at a dosage of about 0.12 mg/kg once daily for seven days followed by a dosing holiday, wherein the dosing holiday is followed by resuming administration of Compound 1 at the same dosing regimen as compared to the administration before the dosing holiday.

In some embodiments, Compound 1 is administered at a dosage of about 0.12 mg/kg once daily for seven days followed by a dosing holiday, wherein the dosing holiday is followed by resuming administration of Compound 1 at a dosage of about 0.12 mg/kg once daily for seven days.

In some embodiments, Compound 1 is administered at a dosage of about 0.12 mg/kg once daily for seven days followed by a seven day dosing holiday for one month, two months, three months, four months, five months, six months, seven months, eight months, nine months, ten months, eleven months, or twelve months.

In some embodiments, Compound 1 is administered at a dosage of about 0.12±0.05 mg/kg, about 0.12±0.04 mg/kg, about 0.12±0.03 mg/kg, about 0.12±0.02 mg/kg, or about 0.12±0.01 mg/kg.

In some embodiments, Compound 1 is administered at a dosage of about 0.24 mg/kg.

In some embodiments, Compound 1 is administered at a dosage of about 0.24 mg/kg once daily for seven days.

In some embodiments, Compound 1 is administered at a dosage of about 0.24 mg/kg once daily for two weeks.

In some embodiments, Compound 1 is administered at a dosage of about 0.24 mg/kg once daily for three weeks.

In some embodiments, Compound 1 is administered at a dosage of about 0.24 mg/kg once daily for four weeks.

In some embodiments, Compound 1 is administered at a dosage of about 0.24 mg/kg once daily for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

In some embodiments, Compound 1 is administered at a dosage of 0.24 mg/kg once daily for seven days followed by a seven day dosing holiday.

In some embodiments, Compound 1 is administered at a dosage of about 0.24 mg/kg once daily for seven days followed by a one week dosing holiday, a two week dosing holiday, a three week dosing holiday, a four week dosing holiday, a six week dosing holiday, an eight week dosing holiday, a 10 week dosing holiday, a 12 week dosing holiday, a 14 week dosing holiday, a 16 week dosing holiday, an 18 week dosing holiday, a 20 week dosing holiday, a 22 week dosing holiday, a 24 week dosing holiday, a 28 week dosing holiday, a 32 week dosing holiday, a 36 week dosing holiday, a 40 week dosing holiday, a 44 week dosing holiday, a 48 week dosing holiday, or a 52 week dosing holiday.

In some embodiments, Compound 1 is administered at a dosage of about 0.24 mg/kg once daily for seven days followed by a dosing holiday, wherein the dosing holiday is followed by resuming administration of Compound 1 at a different dosing regimen as compared to the administration before the dosing holiday.

In some embodiments, Compound 1 is administered at a dosage of about 0.24 mg/kg once daily for seven days followed by a dosing holiday, wherein the dosing holiday is followed by resuming administration of Compound 1 at the same dosing regimen as compared to the administration before the dosing holiday.

In some embodiments, Compound 1 is administered at a dosage of about 0.24 mg/kg once daily for seven days followed by a dosing holiday, wherein the dosing holiday is followed by resuming administration of Compound 1 at a dosage of about 0.12 mg/kg once daily for seven days.

In some embodiments, Compound 1 is administered at a dosage of about 0.24 mg/kg once daily for seven days followed by a seven day dosing holiday for one month, two months, three months, four months, five months, six months, seven months, eight months, nine months, ten months, eleven months, or twelve months.

In some embodiments, Compound 1 is administered at a dosage of about 0.24±0.1 mg, about 0.24±0.09 mg, about 0.24±0.08 mg, about 0.24±0.07 mg, about 0.24±0.06 mg, about 0.24±0.05 mg, about 0.24±0.04 mg, about 0.24±0.03 mg, about 0.24±0.02 mg, or about 0.24±0.01 mg.

In some embodiments, Compound 1 is administered at a dosage of about 0.12 mg/kg or about 0.24 mg/kg.

In some embodiments, Compound 1 is administered at a dosage of about 0.12 mg/kg or about 0.24 mg/kg once daily for seven days.

In some embodiments, Compound 1 is administered at a dosage of about 0.12 mg/kg or about 0.24 mg/kg once daily for seven days followed by a seven day dosing holiday.

In some embodiments, Compound 1 is administered at a dosage of about 0.12 mg/kg or about 0.24 mg/kg once daily for seven days followed by a seven day dosing holiday for one month, two months, three months, four months, five months, six months, seven months, eight months, nine months, ten months, eleven months, or twelve months.

In some embodiments, Compound 1 is administered at a dosage from about 0.01 mg/kg to about 0.8 mg/kg.

In some embodiments, Compound 1 is administered at a dosage from about 0.01 mg/kg to about 0.8 mg/kg once daily.

In some embodiments, Compound 1 is administered at a dosage from about 0.01 mg/kg to about 0.8 mg/kg once daily for seven days.

In some embodiments, Compound 1 is administered at a dosage from about 0.01 mg/kg to about 0.8 mg/kg once daily for two weeks.

In some embodiments, Compound 1 is administered at a dosage from about 0.01 mg/kg to about 0.8 mg/kg once daily for three weeks.

In some embodiments, Compound 1 is administered at a dosage from about 0.01 mg/kg to about 0.8 mg/kg once daily for four weeks.

In some embodiments, Compound 1 is administered at a dosage from about 0.01 mg/kg to about 0.8 mg/kg once daily for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

In some embodiments, Compound 1 is administered at a dosage from about 0.01 mg/kg to about 0.8 mg/kg followed by a dosing holiday.

In some embodiments, Compound 1 is administered at a dosage from about 0.01 mg/kg to about 0.8 mg/kg followed by a one week dosing holiday, a two week dosing holiday, a three week dosing holiday, a four week dosing holiday, a six week dosing holiday, an eight week dosing holiday, a 10 week dosing holiday, a 12 week dosing holiday, a 14 week dosing holiday, a 16 week dosing holiday, an 18 week dosing holiday, a 20 week dosing holiday, a 22 week dosing holiday, a 24 week dosing holiday, a 28 week dosing holiday, a 32 week dosing holiday, a 36 week dosing holiday, a 40 week dosing holiday, a 44 week dosing holiday, a 48 week dosing holiday, or a 52 week dosing holiday.

In some embodiments, Compound 1 is administered at a dosage from about 0.01 mg/kg to about 0.8 mg/kg followed by a dosing holiday, wherein the dosing holiday is followed by resuming administration of Compound 1 at a different dosing regimen as compared to the administration before the dosing holiday.

In some embodiments, Compound 1 is administered at a dosage from about 0.01 mg/kg to about 0.8 mg/kg followed by a dosing holiday, wherein the dosing holiday is followed by resuming administration of Compound 1 at the same dosing regimen as compared to the administration before the dosing holiday.

In some embodiments, Compound 1 is administered at a dosage from about 0.01 mg/kg to about 0.8 mg/kg followed by a dosing holiday, wherein the dosing holiday is followed by resuming administration of Compound 1 at a dosage from about 0.01 mg/kg to about 0.8 mg/kg.

In some embodiments, Compound 1 is administered at a dosage from about 0.01 mg/kg to about 0.8 mg/kg, about 0.05 mg/kg to about 0.75 mg/kg, 0.1 mg/kg to about 0.7 mg/kg, 0.2 mg/kg to about 0.6 mg/kg, 0.3 mg/kg to about 0.5 mg/kg, or 0.3 mg/kg to about 0.4 mg/kg.

In some embodiments, Compound 1 is administered at a dosage from about 0.01 mg/kg to about 0.8 mg/kg, about 0.01 mg/kg to about 0.7 mg/kg, about 0.01 mg/kg to about 0.6 mg/kg, about 0.01 mg/kg to about 0.5 mg/kg, about 0.01 mg/kg to about 0.4 mg/kg, about 0.01 mg/kg to about 0.3 mg/kg, about 0.01 mg/kg to about 0.2 mg/kg, about 0.01 mg/kg to about 0.1 mg/kg, about 0.01 mg/kg to about 0.08 mg/kg, about 0.01 mg/kg to about 0.06 mg/kg, about 0.01 mg/kg to about 0.05 mg/kg, about 0.01 mg/kg to about 0.04 mg/kg, about 0.01 mg/kg to about 0.03 mg/kg, or about 0.01 mg/kg to about 0.02 mg/kg.

In some embodiments, Compound 1 is administered at a dosage from about 0.01 mg/kg to about 0.8 mg/kg, about 0.02 mg/kg to about 0.8 mg/kg, about 0.03 mg/kg to about 0.8 mg/kg, about 0.04 mg/kg to about 0.8 mg/kg, about 0.05 mg/kg to about 0.8 mg/kg, about 0.06 mg/kg to about 0.8 mg/kg, about 0.08 mg/kg to about 0.8 mg/kg, about 0.1 mg/kg to about 0.8 mg/kg, about 0.2 mg/kg to about 0.8 mg/kg, about 0.3 mg/kg to about 0.8 mg/kg, about 0.4 mg/kg to about 0.8 mg/kg, about 0.5 mg/kg to about 0.8 mg/kg, about 0.6 mg/kg to about 0.8 mg/kg, or about 0.7 mg/kg to about 0.8 mg/kg.

In some embodiments, Compound 1 is administered at a dosage from about 0.03 mg/kg to about 0.55 mg/kg.

In some embodiments, Compound 1 is administered at a dosage from about 0.03 mg/kg to about 0.55 mg/kg once daily.

In some embodiments, Compound 1 is administered at a dosage from about 0.03 mg/kg to about 0.55 mg/kg once daily for seven days.

In some embodiments, Compound 1 is administered at a dosage from about 0.03 mg/kg to about 0.55 mg/kg once daily for two weeks.

In some embodiments, Compound 1 is administered at a dosage from about 0.03 mg/kg to about 0.55 mg/kg once daily for three weeks.

In some embodiments, Compound 1 is administered at a dosage from about 0.03 mg/kg to about 0.55 mg/kg once daily for four weeks.

In some embodiments, Compound 1 is administered at a dosage from about 0.03 mg/kg to about 0.55 mg/kg once daily for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

In some embodiments, Compound 1 is administered at a dosage from about 0.03 mg/kg to about 0.55 mg/kg followed by a dosing holiday.

In some embodiments, Compound 1 is administered at a dosage from about 0.03 mg/kg to about 0.55 mg/kg followed by a one week dosing holiday, a two week dosing holiday, a three week dosing holiday, a four week dosing holiday, a six week dosing holiday, an eight week dosing holiday, a 10 week dosing holiday, a 12 week dosing holiday, a 14 week dosing holiday, a 16 week dosing holiday, an 18 week dosing holiday, a 20 week dosing holiday, a 22 week dosing holiday, a 24 week dosing holiday, a 28 week dosing holiday, a 32 week dosing holiday, a 36 week dosing holiday, a 40 week dosing holiday, a 44 week dosing holiday, a 48 week dosing holiday, or a 52 week dosing holiday.

In some embodiments, Compound 1 is administered at a dosage from about 0.03 mg/kg to about 0.55 mg/kg followed by a dosing holiday, wherein the dosing holiday is followed by resuming administration of Compound 1 at a different dosing regimen as compared to the administration before the dosing holiday.

In some embodiments, Compound 1 is administered at a dosage from about 0.03 mg/kg to about 0.55 mg/kg followed by a dosing holiday, wherein the dosing holiday is followed by resuming administration of Compound 1 at the same dosing regimen as compared to the administration before the dosing holiday.

In some embodiments, Compound 1 is administered at a dosage from about 0.03 mg/kg to about 0.55 mg/kg followed by a dosing holiday, wherein the dosing holiday is followed by resuming administration of Compound 1 at a dosage from about 0.03 mg/kg to about 0.55 mg/kg.

In some embodiments, Compound 1 is administered at a dosage from about 0.03 mg/kg to about 0.55 mg/kg, about 0.05 mg/kg to about 0.5 mg/kg, about 0.1 mg/kg to about 0.45 mg/kg, about 0.15 mg/kg to about 0.4 mg/kg, about 0.2 mg/kg to about 0.35 mg/kg, or about 0.25 mg/kg to about 0.3 mg/kg.

In some embodiments, Compound 1 is administered at a dosage from about 0.03 mg/kg to about 0.55 mg/kg, about 0.03 mg/kg to about 0.5 mg/kg, about 0.03 mg/kg to about 0.45 mg/kg, about 0.03 mg/kg to about 0.4 mg/kg, about 0.03 mg/kg to about 0.35 mg/kg, about 0.03 mg/kg to about 0.3 mg/kg, about 0.03 mg/kg to about 0.25 mg/kg, about 0.03 mg/kg to about 0.2 mg/kg, about 0.03 mg/kg to about 0.15 mg/kg, about 0.03 mg/kg to about 0.1 mg/kg, about 0.03 mg/kg to about 0.09 mg/kg, about 0.03 mg/kg to about 0.08 mg/kg, about 0.03 mg/kg to about 0.07 mg/kg, about 0.03 mg/kg to about 0.06 mg/kg, about 0.03 mg/kg to about 0.05 mg/kg, or about 0.03 mg/kg to about 0.04 mg/kg.

In some embodiments, Compound 1 is administered at a dosage from about 0.03 mg/kg to about 0.55 mg/kg, 0.04 mg/kg to about 0.55 mg/kg, about 0.05 mg/kg to about 0.55 mg/kg, about 0.06 mg/kg to about 0.55 mg/kg, about 0.07 mg/kg to about 0.55 mg/kg, about 0.08 mg/kg to about 0.55 mg/kg, about 0.09 mg/kg to about 0.55 mg/kg, about 0.1 mg/kg to about 0.55 mg/kg, about 0.15 mg/kg to about 0.55 mg/kg, about 0.2 mg/kg to about 0.55 mg/kg, about 0.25 mg/kg to about 0.55 mg/kg, about 0.3 mg/kg to about 0.55 mg/kg, about 0.35 mg/kg to about 0.55 mg/kg, about 0.4 mg/kg to about 0.55 mg/kg, about 0.45 mg/kg to about 0.55 mg/kg, or about 0.5 mg/kg to about 0.55 mg/kg.

In some embodiments, Compound 1 is administered at a dosage of about 0.08 mg/kg.

In some embodiments, Compound 1 is administered at a dosage of about 0.08 mg/kg once daily.

In some embodiments, Compound 1 is administered at a dosage of about 0.08 mg/kg once daily for seven days.

In some embodiments, Compound 1 is administered at a dosage of about 0.08 mg/kg once daily for two weeks.

In some embodiments, Compound 1 is administered at a dosage of about 0.08 mg/kg once daily for three weeks.

In some embodiments, Compound 1 is administered at a dosage of about 0.08 mg/kg once daily for four weeks.

In some embodiments, Compound 1 is administered at a dosage of about 0.08 mg/kg once daily for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

In some embodiments, Compound 1 is administered at a dosage of about 0.08 mg/kg followed by a dosing holiday.

In some embodiments, Compound 1 is administered at a dosage of about 0.08 mg/kg followed by a one week dosing holiday, a two week dosing holiday, a three week dosing holiday, a four week dosing holiday, a six week dosing holiday, an eight week dosing holiday, a 10 week dosing holiday, a 12 week dosing holiday, a 14 week dosing holiday, a 16 week dosing holiday, an 18 week dosing holiday, a 20 week dosing holiday, a 22 week dosing holiday, a 24 week dosing holiday, a 28 week dosing holiday, a 32 week dosing holiday, a 36 week dosing holiday, a 40 week dosing holiday, a 44 week dosing holiday, a 48 week dosing holiday, or a 52 week dosing holiday.

In some embodiments, Compound 1 is administered at a dosage of about 0.08 mg/kg followed by a dosing holiday, wherein the dosing holiday is followed by resuming administration of Compound 1 at a different dosing regimen as compared to the administration before the dosing holiday.

In some embodiments, Compound 1 is administered at a dosage of about 0.08 mg/kg followed by a dosing holiday, wherein the dosing holiday is followed by resuming administration of Compound 1 at the same dosing regimen as compared to the administration before the dosing holiday.

In some embodiments, Compound 1 is administered at a dosage of about 0.08 mg/kg followed by a dosing holiday, wherein the dosing holiday is followed by resuming administration of Compound 1 at a dosage of about 0.08 mg/kg.

In some embodiments, Compound 1 is administered at a dosage of about 0.8±0.05 mg/kg, about 0.8±0.04 mg/kg, about 0.8±0.03 mg/kg, about 0.8±0.02 mg/kg, or about 0.8±0.01 mg/kg.

In some embodiments, Compound 1 is administered at a dosage of about 0.24 mg/kg.

In some embodiments, Compound 1 is administered at a dosage of about 0.24 mg/kg once daily.

In some embodiments, Compound 1 is administered at a dosage of about 0.24 mg/kg once daily for seven days.

In some embodiments, Compound 1 is administered at a dosage of about 0.24 mg/kg once daily for two weeks.

In some embodiments, Compound 1 is administered at a dosage of about 0.24 mg/kg once daily for three weeks.

In some embodiments, Compound 1 is administered at a dosage of about 0.24 mg/kg once daily for four weeks.

In some embodiments, Compound 1 is administered at a dosage of about 0.24 mg/kg once daily for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

In some embodiments, Compound 1 is administered at a dosage of about 0.24 mg/kg followed by a dosing holiday.

In some embodiments, Compound 1 is administered at a dosage of about 0.24 mg/kg followed by a one week dosing holiday, a two week dosing holiday, a three week dosing holiday, a four week dosing holiday, a six week dosing holiday, an eight week dosing holiday, a 10 week dosing holiday, a 12 week dosing holiday, a 14 week dosing holiday, a 16 week dosing holiday, an 18 week dosing holiday, a 20 week dosing holiday, a 22 week dosing holiday, a 24 week dosing holiday, a 28 week dosing holiday, a 32 week dosing holiday, a 36 week dosing holiday, a 40 week dosing holiday, a 44 week dosing holiday, a 48 week dosing holiday, or a 52 week dosing holiday.

In some embodiments, Compound 1 is administered at a dosage of about 0.24 mg/kg followed by a dosing holiday, wherein the dosing holiday is followed by resuming administration of Compound 1 at a different dosing regimen as compared to the administration before the dosing holiday.

In some embodiments, Compound 1 is administered at a dosage of about 0.24 mg/kg followed by a dosing holiday, wherein the dosing holiday is followed by resuming administration of Compound 1 at the same dosing regimen as compared to the administration before the dosing holiday.

In some embodiments, Compound 1 is administered at a dosage of about 0.24 mg/kg followed by a dosing holiday, wherein the dosing holiday is followed by resuming administration of Compound 1 at a dosage of about 0.24 mg/kg.

Compound 1 is administered at a dosage of about 0.24±0.2 mg/kg, about 0.24±0.18 mg/kg, about 0.24±0.16 mg/kg, about 0.24±0.15 mg/kg, about 0.24±0.14 mg/kg, about 0.24±0.13 mg/kg, about 0.24±0.12 mg/kg, about 0.24±0.11 mg/kg, about 0.24±0.1 mg/kg, about 0.24±0.09 mg/kg, about 0.24±0.08 mg/kg, about 0.24±0.07 mg/kg, about 0.24±0.06 mg/kg, about 0.24±0.05 mg/kg, about 0.24±0.04 mg/kg, about 0.24±0.03 mg/kg, about 0.24±0.02 mg/kg, or about 0.24±0.01 mg/kg.

In some embodiments, Compound 1 is administered at a dosage of about 0.48 mg/kg.

In some embodiments, Compound 1 is administered at a dosage of about 0.48 mg/kg once daily.

In some embodiments, Compound 1 is administered at a dosage of about 0.48 mg/kg once daily for seven days.

In some embodiments, Compound 1 is administered at a dosage of about 0.48 mg/kg once daily for two weeks.

In some embodiments, Compound 1 is administered at a dosage of about 0.48 mg/kg once daily for three weeks.

In some embodiments, Compound 1 is administered at a dosage of about 0.48 mg/kg once daily for four weeks.

In some embodiments, Compound 1 is administered at a dosage of about 0.48 mg/kg once daily for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

In some embodiments, Compound 1 is administered at a dosage of about 0.48 mg/kg followed by a dosing holiday.

In some embodiments, Compound 1 is administered at a dosage of about 0.48 mg/kg followed by a one week dosing holiday, a two week dosing holiday, a three week dosing holiday, a four week dosing holiday, a six week dosing holiday, an eight week dosing holiday, a 10 week dosing holiday, a 12 week dosing holiday, a 14 week dosing holiday, a 16 week dosing holiday, an 18 week dosing holiday, a 20 week dosing holiday, a 22 week dosing holiday, a 24 week dosing holiday, a 28 week dosing holiday, a 32 week dosing holiday, a 36 week dosing holiday, a 40 week dosing holiday, a 44 week dosing holiday, a 48 week dosing holiday, or a 52 week dosing holiday.

In some embodiments, Compound 1 is administered at a dosage of about 0.48 mg/kg followed by a dosing holiday, wherein the dosing holiday is followed by resuming administration of Compound 1 at a different dosing regimen as compared to the administration before the dosing holiday.

In some embodiments, Compound 1 is administered at a dosage of about 0.48 mg/kg followed by a dosing holiday, wherein the dosing holiday is followed by resuming administration of Compound 1 at the same dosing regimen as compared to the administration before the dosing holiday.

In some embodiments, Compound 1 is administered at a dosage of about 0.48 mg/kg followed by a dosing holiday, wherein the dosing holiday is followed by resuming administration of Compound 1 at a dosage of about 0.48 mg/kg.

In some embodiments, Compound 1 is administered at a dosage of about 0.48±0.12 mg/kg, about 0.48±0.11 mg/kg, about 0.48±0.1 mg/kg, about 0.48±0.09 mg/kg, about 0.48±0.08 mg/kg, about 0.48±0.07 mg/kg, about 0.48±0.06 mg/kg, about 0.48±0.05 mg/kg, about 0.48±0.04 mg/kg, about 0.48±0.03 mg/kg, about 0.48±0.02 mg/kg, or about 0.48±0.01 mg/kg.

In some embodiments, Compound 1 is administered at a dosage of about 0.08 mg/kg, about 0.24 mg/kg, or about 0.48 mg/kg.

In some embodiments, Compound 1 is administered at a dosage about 0.08 mg/kg, about 0.24 mg/kg, or about 0.48 mg/kg once daily.

In some embodiments, Compound 1 is administered at a dosage of about 0.08 mg/kg, about 0.24 mg/kg, or about 0.48 mg/kg once daily for seven days.

In some embodiments, Compound 1 is administered at a dosage of about 0.08 mg/kg, about 0.24 mg/kg, or about 0.48 mg/kg once daily for two weeks.

In some embodiments, Compound 1 is administered at a dosage of about 0.08 mg/kg, about 0.24 mg/kg, or about 0.48 mg/kg once daily for three weeks.

In some embodiments, Compound 1 is administered at a dosage of about 0.08 mg/kg, about 0.24 mg/kg, or about 0.48 mg/kg once daily for four weeks.

In some embodiments, Compound 1 is administered at a dosage of about 0.08 mg/kg, about 0.24 mg/kg, or about 0.48 mg/kg once daily for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

In some embodiments, Compound 1 is administered at a dosage of about 0.08 mg/kg, about 0.24 mg/kg, or about 0.48 mg/kg followed by a dosing holiday.

In some embodiments, Compound 1 is administered at a dosage of about 0.08 mg/kg, about 0.24 mg/kg, or about 0.48 mg/kg once daily followed by a one week dosing holiday, a two week dosing holiday, a three week dosing holiday, a four week dosing holiday, a six week dosing holiday, an eight week dosing holiday, a 10 week dosing holiday, a 12 week dosing holiday, a 14 week dosing holiday, a 16 week dosing holiday, an 18 week dosing holiday, a 20 week dosing holiday, a 22 week dosing holiday, a 24 week dosing holiday, a 28 week dosing holiday, a 32 week dosing holiday, a 36 week dosing holiday, a 40 week dosing holiday, a 44 week dosing holiday, a 48 week dosing holiday, or a 52 week dosing holiday.

In some embodiments, Compound 1 is administered at a dosage of about 0.08 mg/kg, about 0.24 mg/kg, or about 0.48 mg/kg once daily followed by a dosing holiday, wherein the dosing holiday is followed by resuming administration of Compound 1 at a different dosing regimen as compared to the administration before the dosing holiday.

In some embodiments, Compound 1 is administered at a dosage of about 0.08 mg/kg, about 0.24 mg/kg, or about 0.48 mg/kg once daily followed by a dosing holiday, wherein the dosing holiday is followed by resuming administration of Compound 1 at the same dosing regimen as compared to the administration before the dosing holiday.

In some embodiments, Compound 1 is administered at a dosage of about 0.08 mg/kg, about 0.24 mg/kg, or about 0.48 mg/kg once daily followed by a dosing holiday, wherein the dosing holiday is followed by resuming administration of Compound 1 at a dosage of about 0.08 mg/kg, about 0.24 mg/kg, or about 0.48 mg/kg once daily.

In some embodiments, Compound 1 is administered once every seven days at a dosage of about 1.2 mg/kg.

In some embodiments, Compound 1 is administered once every seven days at a dosage of about 1.2±1.1 mg/kg, about 1.2±1 mg/kg, about 1.2±0.9 mg/kg, about 1.2±0.8 mg/kg, about 1.2±0.7 mg/kg, about 1.2±0.6 mg/kg, about 1.2±0.5 mg/kg, about 1.2±0.4 mg/kg, about 1.2±0.3 mg/kg, about 1.2±0.2 mg/kg, or about 1.2±0.1 mg/kg.

In some embodiments, Compound 1 is administered once every seven days at a dosage of about 2.4 mg/kg.

In some embodiments, Compound 1 is administered once every seven days at a dosage of about 2.4±2 mg/kg, about 2.4±1.8 mg/kg, about 2.4±1.6 mg/kg, about 2.4±1.5 mg/kg, about 2.4±1.4 mg/kg, about 2.4±1.3 mg/kg, about 2.4±1.2 mg/kg, about 2.4±1.1 mg/kg, about 2.4±1 mg/kg, about 2.4±0.9 mg/kg, about 2.4±0.8 mg/kg, about 2.4±0.7 mg/kg, about 2.4±0.6 mg/kg, about 2.4±0.5 mg/kg, about 2.4±0.4 mg/kg, about 2.4±0.3 mg/kg, about 2.4±0.2 mg/kg, or about 2.4±0.1 mg/kg.

In some embodiments, Compound 1 is administered once every seven days at a dosage of about 4.8 mg/kg.

In some embodiments, Compound 1 is administered once every seven days at a dosage of about 4.8±4.2 mg/kg, about 4.8±3.6 mg/kg, about 4.8±3.2 mg/kg, about 4.8±2.8 mg/kg, about 4.8±2.4 mg/kg, about 4.8±2 mg/kg, about 4.8±1.8 mg/kg, about 4.8±1.6 mg/kg, about 4.8±1.5 mg/kg, about 4.8±1.4 mg/kg, about 4.8±1.3 mg/kg, about 4.8±1.2 mg/kg, about 4.8±1.1 mg/kg, about 4.8±1 mg/kg, about 4.8±0.9 mg/kg, about 4.8±0.8 mg/kg, about 4.8±0.7 mg/kg, about 4.8±0.6 mg/kg, about 4.8±0.5 mg/kg, about 4.8±0.4 mg/kg, about 4.8±0.3 mg/kg, about 4.8±0.2 mg/kg, or about 4.8±0.1 mg/kg.

In some embodiments, Compound 1 is administered once every seven days at a dosage of about 1.2 mg/kg, about 2.4 mg/kg, or about 4.8 mg/kg.

In some embodiments, Compound 1 is administered at a dosage of about 0.12 mg/kg for seven consecutive days followed by a seven day dosing holiday.

In some embodiments, Compound 1 is administered at a dosage of about at a dosage of about 0.12 mg/kg for seven consecutive days followed by a dosing holiday, wherein the dosing holiday is followed by resuming administration of Compound 1 at a different dosing regimen as compared to the administration before the dosing holiday.

In some embodiments, Compound 1 is administered at a dosage of about at a dosage of about 0.12 mg/kg for seven consecutive days followed by a dosing holiday, wherein the dosing holiday is followed by resuming administration of Compound 1 at the same dosing regimen as compared to the administration before the dosing holiday.

In some embodiments, Compound 1 is administered at a dosage of about at a dosage of about 0.12 mg/kg for seven consecutive days followed by a dosing holiday, wherein the dosing holiday is followed by resuming administration of Compound 1 at a dosage of about 0.12 mg/kg for seven consecutive days.

In some embodiments, Compound 1 is administered for seven consecutive days followed by a seven day dosing holiday at a dosage of about 0.12±0.1 mg/kg, about 0.12±0.09 mg/kg, about 0.12±0.08 mg/kg, about 0.12±0.07 mg/kg, about 0.12±0.06 mg/kg, about 0.12±0.05 mg/kg, about 0.12±0.04 mg/kg, about 0.12±0.03 mg/kg, about 0.12±0.02 mg/kg, or about 0.12±0.01 mg/kg.

In some embodiments, Compound 1 is administered at a dosage of about 0.24 mg/kg for seven consecutive days followed by a dosing holiday, wherein the dosing holiday is followed by resuming administration of Compound 1 at a different dosing regimen as compared to the administration before the dosing holiday.

In some embodiments, Compound 1 is administered at a dosage of about 0.24 mg/kg for seven consecutive days followed by a dosing holiday, wherein the dosing holiday is followed by resuming administration of Compound 1 at the same dosing regimen as compared to the administration before the dosing holiday.

In some embodiments, Compound 1 is administered at a dosage of about 0.24 mg/kg for seven consecutive days followed by a seven day dosing holiday.

In some embodiments, Compound 1 is administered at a dosage of about 0.24 mg/kg for seven consecutive days followed by a dosing holiday, wherein the dosing holiday is followed by resuming administration of Compound 1 at a dosage of about 0.24 mg/kg for seven consecutive days.

In some embodiments, Compound 1 is administered for seven consecutive days followed by a seven day dosing holiday at a dosage of about 0.24±0.2 mg/kg, about 0.24±0.18 mg/kg, about 0.24±0.16 mg/kg, about 0.24±0.15 mg/kg, about 0.24±0.14 mg/kg, about 0.24±0.13 mg/kg, about 0.24±0.12 mg/kg, about 0.24±0.11 mg/kg, about 0.24±0.1 mg/kg, about 0.24±0.09 mg/kg, about 0.24±0.08 mg/kg, about 0.24±0.07 mg/kg, about 0.24±0.06 mg/kg, about 0.24±0.05 mg/kg, about 0.24±0.04 mg/kg, about 0.24±0.03 mg/kg, about 0.24±0.02 mg/kg, or about 0.24±0.01 mg/kg.

In some embodiments, Compound 1 is administered at a dosage of about 0.12 mg/kg or about 0.24 mg/kg for seven consecutive days followed by a dosing holiday, wherein the dosing holiday is followed by resuming administration of Compound 1 at a different dosing regimen as compared to the administration before the dosing holiday.

In some embodiments, Compound 1 is administered at a dosage of about 0.12 mg/kg or about 0.24 mg/kg for seven consecutive days followed by a dosing holiday, wherein the dosing holiday is followed by resuming administration of Compound 1 at the same dosing regimen as compared to the administration before the dosing holiday.

In some embodiments, Compound 1 is administered at a dosage of about 0.12 mg/kg or about 0.24 mg/kg for seven consecutive days followed by a seven day dosing holiday.

In some embodiments, Compound 1 is administered at a dosage of about 0.12 mg/kg or about 0.24 mg/kg for seven consecutive days followed by a dosing holiday, wherein the dosing holiday is followed by resuming administration of Compound 1 at a dosage of about 0.12 mg/kg or about 0.24 mg/kg for seven consecutive days.

In some embodiments, Compound 1 is administered once daily at a dosage of about 0.08 mg/kg.

In some embodiments, Compound 1 is administered once daily at a dosage of about 0.08±0.07 mg/kg, about 0.8±0.06 mg/kg, about 0.8±0.05 mg/kg, about 0.8±0.04 mg/kg, about 0.8±0.03 mg/kg, about 0.8±0.02 mg/kg, or about 0.8±0.01 mg/kg.

In some embodiments, Compound 1 is administered once daily at a dosage of about 0.24 mg/kg.

In some embodiments, Compound 1 is administered once daily at a dosage of about 0.24±0.2 mg/kg, about 0.24±0.18 mg/kg, about 0.24±0.16 mg/kg, about 0.24±0.15 mg/kg, about 0.24±0.14 mg/kg, about 0.24±0.13 mg/kg, about 0.24±0.12 mg/kg, about 0.24±0.11 mg/kg, about 0.24±0.1 mg/kg, about 0.24±0.09 mg/kg, about 0.24±0.08 mg/kg, about 0.24±0.07 mg/kg, about 0.24±0.06 mg/kg, about 0.24±0.05 mg/kg, about 0.24±0.04 mg/kg, about 0.24±0.03 mg/kg, about 0.24±0.02 mg/kg, or about 0.24±0.01 mg/kg.

In some embodiments, Compound 1 is administered once daily at a dosage of about 0.48 mg/kg.

In some embodiments, Compound 1 is administered once daily at a dosage of about 0.48±0.12 mg/kg, about 0.48±0.11 mg/kg, about 0.48±0.1 mg/kg, about 0.48±0.09 mg/kg, about 0.48±0.08 mg/kg, about 0.48±0.07 mg/kg, about 0.48±0.06 mg/kg, about 0.48±0.05 mg/kg, about 0.48±0.04 mg/kg, about 0.48±0.03 mg/kg, about 0.48±0.02 mg/kg, or about 0.48±0.01 mg/kg.

In some embodiments, Compound 1 is administered once daily at a dosage of about 0.12 mg/kg, about 0.24 mg/kg, or 0.48 mg/kg.

In some embodiments, Compound 1 is administered at a dosage of about 0.01 mg/kg. In some embodiments, Compound 1 is administered at a dosage of about 0.02 mg/kg. In some embodiments, Compound 1 is administered at a dosage of about 0.03 mg/kg. In some embodiments, Compound 1 is administered at a dosage of about 0.04 mg/kg. In some embodiments, Compound 1 is administered at a dosage of about 0.05 mg/kg. In some embodiments, Compound 1 is administered at a dosage of about 0.06 mg/kg. In some embodiments, Compound 1 is administered at a dosage of about 0.07 mg/kg. In some embodiments, Compound 1 is administered at a dosage of about 0.08 mg/kg. In some embodiments, Compound 1 is administered at a dosage of about 0.09 mg/kg.

In some embodiments, Compound 1 is administered at a dosage of about 0.1 mg/kg. In some embodiments, Compound 1 is administered at a dosage of about 0.12 mg/kg. In some embodiments, Compound 1 is administered at a dosage of about 0.14 mg/kg. In some embodiments, Compound 1 is administered at a dosage of about 0.16 mg/kg. In some embodiments, Compound 1 is administered at a dosage of about 0.18 mg/kg.

In some embodiments, Compound 1 is administered at a dosage of about 0.2 mg/kg. In some embodiments, Compound 1 is administered at a dosage of about 0.22 mg/kg. In some embodiments, Compound 1 is administered at a dosage of about 0.24 mg/kg. In some embodiments, Compound 1 is administered at a dosage of about 0.26 mg/kg. In some embodiments, Compound 1 is administered at a dosage of about 0.28 mg/kg.

In some embodiments, Compound 1 is administered at a dosage of about 0.3 mg/kg. In some embodiments, Compound 1 is administered at a dosage of about 0.32 mg/kg. In some embodiments, Compound 1 is administered at a dosage of about 0.34 mg/kg. In some embodiments, Compound 1 is administered at a dosage of about 0.36 mg/kg. In some embodiments, Compound 1 is administered at a dosage of about 0.38 mg/kg.

In some embodiments, Compound 1 is administered at a dosage of about 0.4 mg/kg. In some embodiments, Compound 1 is administered at a dosage of about 0.42 mg/kg. In some embodiments, Compound 1 is administered at a dosage of about 0.44 mg/kg. In some embodiments, Compound 1 is administered at a dosage of about 0.46 mg/kg. In some embodiments, Compound 1 is administered at a dosage of about 0.48 mg/kg.

In some embodiments, Compound 1 is administered at a dosage of about 0.5 mg/kg. In some embodiments, Compound 1 is administered at a dosage of about 0.55 mg/kg.

In some embodiments, Compound 1 is administered at a dosage of about 0.6 mg/kg. In some embodiments, Compound 1 is administered at a dosage of about 0.65 mg/kg.

In some embodiments, Compound 1 is administered at a dosage of about 0.7 mg/kg. In some embodiments, Compound 1 is administered at a dosage of about 0.75 mg/kg.

In some embodiments, Compound 1 is administered at a dosage of about 0.8 mg/kg. In some embodiments, Compound 1 is administered at a dosage of about 0.85 mg/kg.

In some embodiments, Compound 1 is administered at a dosage of about 0.9 mg/kg. In some embodiments, Compound 1 is administered at a dosage of about 0.95 mg/kg.

In some embodiments, Compound 1 is administered at a dosage of about 1 mg/kg. In some embodiments, Compound 1 is administered at a dosage of about 1.1 mg/kg. In some embodiments, Compound 1 is administered at a dosage of about 1.2 mg/kg. In some embodiments, Compound 1 is administered at a dosage of about 1.3 mg/kg. In some embodiments, Compound 1 is administered at a dosage of about 1.4 mg/kg. In some embodiments, Compound 1 is administered at a dosage of about 1.5 mg/kg. In some embodiments, Compound 1 is administered at a dosage of about 1.6 mg/kg. In some embodiments, Compound 1 is administered at a dosage of about 1.7 mg/kg. In some embodiments, Compound 1 is administered at a dosage of about 1.8 mg/kg. In some embodiments, Compound 1 is administered at a dosage of about 1.9 mg/kg.

In some embodiments, Compound 1 is administered at a dosage of about 2 mg/kg. In some embodiments, Compound 1 is administered at a dosage of about 2.1 mg/kg. In some embodiments, Compound 1 is administered at a dosage of about 2.2 mg/kg. In some embodiments, Compound 1 is administered at a dosage of about 2.3 mg/kg. In some embodiments, Compound 1 is administered at a dosage of about 2.4 mg/kg. In some embodiments, Compound 1 is administered at a dosage of about 2.5 mg/kg. In some embodiments, Compound 1 is administered at a dosage of about 2.6 mg/kg. In some embodiments, Compound 1 is administered at a dosage of about 2.7 mg/kg. In some embodiments, Compound 1 is administered at a dosage of about 2.8 mg/kg. In some embodiments, Compound 1 is administered at a dosage of about 2.9 mg/kg.

In some embodiments, Compound 1 is administered at a dosage of about 3 mg/kg. In some embodiments, Compound 1 is administered at a dosage of about 3.1 mg/kg. In some embodiments, Compound 1 is administered at a dosage of about 3.2 mg/kg. In some embodiments, Compound 1 is administered at a dosage of about 3.3 mg/kg. In some embodiments, Compound 1 is administered at a dosage of about 3.4 mg/kg. In some embodiments, Compound 1 is administered at a dosage of about 3.5 mg/kg. In some embodiments, Compound 1 is administered at a dosage of about 3.6 mg/kg. In some embodiments, Compound 1 is administered at a dosage of about 3.7 mg/kg. In some embodiments, Compound 1 is administered at a dosage of about 3.8 mg/kg. In some embodiments, Compound 1 is administered at a dosage of about 3.9 mg/kg.

In some embodiments, Compound 1 is administered at a dosage of about 4 mg/kg. In some embodiments, Compound 1 is administered at a dosage of about 4.1 mg/kg. In some embodiments, Compound 1 is administered at a dosage of about 4.2 mg/kg. In some embodiments, Compound 1 is administered at a dosage of about 4.3 mg/kg. In some embodiments, Compound 1 is administered at a dosage of about 4.4 mg/kg. In some embodiments, Compound 1 is administered at a dosage of about 4.5 mg/kg. In some embodiments, Compound 1 is administered at a dosage of about 4.6 mg/kg. In some embodiments, Compound 1 is administered at a dosage of about 4.7 mg/kg. In some embodiments, Compound 1 is administered at a dosage of about 4.8 mg/kg. In some embodiments, Compound 1 is administered at a dosage of about 4.9 mg/kg.

In some embodiments, Compound 1 is administered at a dosage of about 5 mg/kg. In some embodiments, Compound 1 is administered at a dosage of about 5.2 mg/kg. In some embodiments, Compound 1 is administered at a dosage of about 5.4 mg/kg. In some embodiments, Compound 1 is administered at a dosage of about 5.6 mg/kg. In some embodiments, Compound 1 is administered at a dosage of about 5.8 mg/kg.

In some embodiments, Compound 1 is administered at a dosage of about 6 mg/kg. In some embodiments, Compound 1 is administered at a dosage of about 6.2 mg/kg. In some embodiments, Compound 1 is administered at a dosage of about 6.4 mg/kg. In some embodiments, Compound 1 is administered at a dosage of about 6.6 mg/kg. In some embodiments, Compound 1 is administered at a dosage of about 6.8 mg/kg.

In some embodiments, Compound 1 is administered at a dosage of about 7.2 mg/kg. In some embodiments, Compound 1 is administered at a dosage of about 7.4 mg/kg. In some embodiments, Compound 1 is administered at a dosage of about 7.6 mg/kg. In some embodiments, Compound 1 is administered at a dosage of about 7.8 mg/kg.

In some embodiments, Compound 1 is administered at a dosage of about 8 mg/kg. In some embodiments, Compound 1 is administered at a dosage of about 8.2 mg/kg. In some embodiments, Compound 1 is administered at a dosage of about 8.4 mg/kg. In some embodiments, Compound 1 is administered at a dosage of about 8.6 mg/kg. In some embodiments, Compound 1 is administered at a dosage of about 8.8 mg/kg.

In some embodiments, Compound 1 is administered at a dosage of about 9 mg/kg. In some embodiments, Compound 1 is administered at a dosage of about 9.2 mg/kg. In some embodiments, Compound 1 is administered at a dosage of about 9.4 mg/kg. In some embodiments, Compound 1 is administered at a dosage of about 9.6 mg/kg. In some embodiments, Compound 1 is administered at a dosage of about 9.8 mg/kg.

In some embodiments, Compound 1 is administered at a dosage of about 10 mg/kg. In some embodiments, Compound 1 is administered at a dosage of about 10.2 mg/kg. In some embodiments, Compound 1 is administered at a dosage of about 10.4 mg/kg. In some embodiments, Compound 1 is administered at a dosage of about 10.6 mg/kg. In some embodiments, Compound 1 is administered at a dosage of about 10.8 mg/kg.

In some embodiments, Compound 1 is administered at a dosage of about 11 mg/kg. In some embodiments, Compound 1 is administered at a dosage of about 11.2 mg/kg. In some embodiments, Compound 1 is administered at a dosage of about 11.4 mg/kg. In some embodiments, Compound 1 is administered at a dosage of about 11.6 mg/kg. In some embodiments, Compound 1 is administered at a dosage of about 11.8 mg/kg.

In some embodiments, Compound 1 is administered at a dosage of about 12 mg/kg. In some embodiments, Compound 1 is administered at a dosage of about 12.2 mg/kg. In some embodiments, Compound 1 is administered at a dosage of about 12.4 mg/kg. In some embodiments, Compound 1 is administered at a dosage of about 12.6 mg/kg. In some embodiments, Compound 1 is administered at a dosage of about 12.8 mg/kg.

In some embodiments, Compound 1 is administered at a dosage of about 13 mg/kg. In some embodiments, Compound 1 is administered at a dosage of about 13.2 mg/kg. In some embodiments, Compound 1 is administered at a dosage of about 13.4 mg/kg. In some embodiments, Compound 1 is administered at a dosage of about 13.6 mg/kg. In some embodiments, Compound 1 is administered at a dosage of about 13.8 mg/kg.

In some embodiments, Compound 1 is administered at a dosage of about 14 mg/kg. In some embodiments, Compound 1 is administered at a dosage of about 14.2 mg/kg. In some embodiments, Compound 1 is administered at a dosage of about 14.4 mg/kg. In some embodiments, Compound 1 is administered at a dosage of about 14.6 mg/kg. In some embodiments, Compound 1 is administered at a dosage of about 14.8 mg/kg.

In some embodiments, Compound 1 is administered at a dosage of about 15 mg/kg. In some embodiments, Compound 1 is administered at a dosage of about 15.2 mg/kg. In some embodiments, Compound 1 is administered at a dosage of about 15.4 mg/kg. In some embodiments, Compound 1 is administered at a dosage of about 15.6 mg/kg. In some embodiments, Compound 1 is administered at a dosage of about 15.8 mg/kg.

In some embodiments, Compound 1 is administered at a dosage of about 16 mg/kg. In some embodiments, Compound 1 is administered at a dosage of about 16.2 mg/kg. In some embodiments, Compound 1 is administered at a dosage of about 16.4 mg/kg. In some embodiments, Compound 1 is administered at a dosage of about 16.6 mg/kg. In some embodiments, Compound 1 is administered at a dosage of about 16.8 mg/kg.

In some embodiments, Compound 1 is administered at a dosage of about 17 mg/kg. In some embodiments, Compound 1 is administered at a dosage of about 17.2 mg/kg. In some embodiments, Compound 1 is administered at a dosage of about 17.4 mg/kg. In some embodiments, Compound 1 is administered at a dosage of about 17.6 mg/kg. In some embodiments, Compound 1 is administered at a dosage of about 17.8 mg/kg.

In some embodiments, Compound 1 is administered at a dosage of about 18 mg/kg. In some embodiments, Compound 1 is administered at a dosage of about 18.2 mg/kg. In some embodiments, Compound 1 is administered at a dosage of about 18.4 mg/kg. In some embodiments, Compound 1 is administered at a dosage of about 18.6 mg/kg. In some embodiments, Compound 1 is administered at a dosage of about 18.8 mg/kg.

In some embodiments, Compound 1 is administered at a dosage of about 19 mg/kg. In some embodiments, Compound 1 is administered at a dosage of about 19.2 mg/kg. In some embodiments, Compound 1 is administered at a dosage of about 19.4 mg/kg. In some embodiments, Compound 1 is administered at a dosage of about 19.6 mg/kg. In some embodiments, Compound 1 is administered at a dosage of about 19.8 mg/kg.

In some embodiments, Compound 1 is administered at a dosage of about 20 mg/kg. In some embodiments, Compound 1 is administered at a dosage of about 20.2 mg/kg. In some embodiments, Compound 1 is administered at a dosage of about 20.4 mg/kg. In some embodiments, Compound 1 is administered at a dosage of about 20.6 mg/kg. In some embodiments, Compound 1 is administered at a dosage of about 20.8 mg/kg.

In some embodiments, Compound 1 is administered at a dosage of about 21 mg/kg. In some embodiments, Compound 1 is administered at a dosage of about 21.2 mg/kg. In some embodiments, Compound 1 is administered at a dosage of about 21.4 mg/kg. In some embodiments, Compound 1 is administered at a dosage of about 21.6 mg/kg. In some embodiments, Compound 1 is administered at a dosage of about 21.8 mg/kg.

In some embodiments, Compound 1 is administered at a dosage of about 22 mg/kg. In some embodiments, Compound 1 is administered at a dosage of about 22.2 mg/kg. In some embodiments, Compound 1 is administered at a dosage of about 22.4 mg/kg. In some embodiments, Compound 1 is administered at a dosage of about 22.6 mg/kg. In some embodiments, Compound 1 is administered at a dosage of about 22.8 mg/kg.

In some embodiments, Compound 1 is administered at a dosage of about 23 mg/kg. In some embodiments, Compound 1 is administered at a dosage of about 23.2 mg/kg. In some embodiments, Compound 1 is administered at a dosage of about 23.4 mg/kg. In some embodiments, Compound 1 is administered at a dosage of about 23.6 mg/kg. In some embodiments, Compound 1 is administered at a dosage of about 23.8 mg/kg.

In some embodiments, Compound 1 is administered at a dosage of about 24 mg/kg. In some embodiments, Compound 1 is administered at a dosage of about 24.2 mg/kg. In some embodiments, Compound 1 is administered at a dosage of about 24.4 mg/kg. In some embodiments, Compound 1 is administered at a dosage of about 24.6 mg/kg. In some embodiments, Compound 1 is administered at a dosage of about 24.8 mg/kg.

In some embodiments, Compound 1 is administered at a dosage of about 25 mg/kg. In some embodiments, Compound 1 is administered at a dosage of about 25.2 mg/kg. In some embodiments, Compound 1 is administered at a dosage of about 25.4 mg/kg. In some embodiments, Compound 1 is administered at a dosage of about 25.6 mg/kg. In some embodiments, Compound 1 is administered at a dosage of about 25.8 mg/kg.

In some embodiments, Compound 1 is administered at a dosage of about 26 mg/kg. In some embodiments, Compound 1 is administered at a dosage of about 26.2 mg/kg. In some embodiments, Compound 1 is administered at a dosage of about 26.4 mg/kg. In some embodiments, Compound 1 is administered at a dosage of about 26.6 mg/kg. In some embodiments, Compound 1 is administered at a dosage of about 26.8 mg/kg.

In some embodiments, Compound 1 is administered at a dosage of about 27 mg/kg. In some embodiments, Compound 1 is administered at a dosage of about 27.2 mg/kg. In some embodiments, Compound 1 is administered at a dosage of about 27.4 mg/kg. In some embodiments, Compound 1 is administered at a dosage of about 27.6 mg/kg. In some embodiments, Compound 1 is administered at a dosage of about 27.8 mg/kg.

In some embodiments, Compound 1 is administered at a dosage of about 28 mg/kg. In some embodiments, Compound 1 is administered at a dosage of about 28.2 mg/kg. In some embodiments, Compound 1 is administered at a dosage of about 28.4 mg/kg. In some embodiments, Compound 1 is administered at a dosage of about 28.6 mg/kg. In some embodiments, Compound 1 is administered at a dosage of about 28.8 mg/kg.

In some embodiments, Compound 1 is administered at a dosage of about 29 mg/kg. In some embodiments, Compound 1 is administered at a dosage of about 29.2 mg/kg. In some embodiments, Compound 1 is administered at a dosage of about 29.4 mg/kg. In some embodiments, Compound 1 is administered at a dosage of about 29.6 mg/kg. In some embodiments, Compound 1 is administered at a dosage of about 29.8 mg/kg.

In some embodiments, Compound 1 is administered at a dosage of about 30 mg/kg. In some embodiments, Compound 1 is administered at a dosage of about 30.2 mg/kg. In some embodiments, Compound 1 is administered at a dosage of about 30.4 mg/kg. In some embodiments, Compound 1 is administered at a dosage of about 30.6 mg/kg. In some embodiments, Compound 1 is administered at a dosage of about 30.8 mg/kg.

In some embodiments, Compound 1 is administered at a dosage of about 31 mg/kg. In some embodiments, Compound 1 is administered at a dosage of about 31.2 mg/kg. In some embodiments, Compound 1 is administered at a dosage of about 31.4 mg/kg. In some embodiments, Compound 1 is administered at a dosage of about 31.6 mg/kg. In some embodiments, Compound 1 is administered at a dosage of about 31.8 mg/kg.

In some embodiments, Compound 1 is administered at a dosage of about 32 mg/kg. In some embodiments, Compound 1 is administered at a dosage of about 32.2 mg/kg. In some embodiments, Compound 1 is administered at a dosage of about 32.4 mg/kg. In some embodiments, Compound 1 is administered at a dosage of about 32.6 mg/kg. In some embodiments, Compound 1 is administered at a dosage of about 32.8 mg/kg.

In some embodiments, Compound 1 is administered at a dosage of about 33 mg/kg. In some embodiments, Compound 1 is administered at a dosage of about 33.2 mg/kg. In some embodiments, Compound 1 is administered at a dosage of about 33.4 mg/kg. In some embodiments, Compound 1 is administered at a dosage of about 33.6 mg/kg. In some embodiments, Compound 1 is administered at a dosage of about 33.8 mg/kg.

In some embodiments, Compound 1 is administered at a dosage of about 34 mg/kg. In some embodiments, Compound 1 is administered at a dosage of about 34.2 mg/kg. In some embodiments, Compound 1 is administered at a dosage of about 34.4 mg/kg. In some embodiments, Compound 1 is administered at a dosage of about 34.6 mg/kg. In some embodiments, Compound 1 is administered at a dosage of about 34.8 mg/kg.

In some embodiments, Compound 1 is administered at a dosage of about 35 mg/kg. In some embodiments, Compound 1 is administered at a dosage of about 35.2 mg/kg. In some embodiments, Compound 1 is administered at a dosage of about 35.4 mg/kg. In some embodiments, Compound 1 is administered at a dosage of about 35.6 mg/kg. In some embodiments, Compound 1 is administered at a dosage of about 35.8 mg/kg.

In some embodiments, Compound 1 is administered at a dosage of about 36 mg/kg. In some embodiments, Compound 1 is administered at a dosage of about 36.2 mg/kg. In some embodiments, Compound 1 is administered at a dosage of about 36.4 mg/kg. In some embodiments, Compound 1 is administered at a dosage of about 36.6 mg/kg. In some embodiments, Compound 1 is administered at a dosage of about 36.8 mg/kg.

In some embodiments, Compound 1 is administered at a dosage of about 37 mg/kg. In some embodiments, Compound 1 is administered at a dosage of about 37.2 mg/kg. In some embodiments, Compound 1 is administered at a dosage of about 37.4 mg/kg. In some embodiments, Compound 1 is administered at a dosage of about 37.6 mg/kg. In some embodiments, Compound 1 is administered at a dosage of about 37.8 mg/kg.

In some embodiments, Compound 1 is administered at a dosage of about 38 mg/kg. In some embodiments, Compound 1 is administered at a dosage of about 38.2 mg/kg. In some embodiments, Compound 1 is administered at a dosage of about 38.4 mg/kg. In some embodiments, Compound 1 is administered at a dosage of about 38.6 mg/kg. In some embodiments, Compound 1 is administered at a dosage of about 38.8 mg/kg.

In some embodiments, Compound 1 is administered at a dosage of about 39 mg/kg. In some embodiments, Compound 1 is administered at a dosage of about 39.2 mg/kg. In some embodiments, Compound 1 is administered at a dosage of about 39.4 mg/kg. In some embodiments, Compound 1 is administered at a dosage of about 39.6 mg/kg. In some embodiments, Compound 1 is administered at a dosage of about 39.8 mg/kg.

In some embodiments, Compound 1 is administered at a dosage of about 40 mg/kg. In some embodiments, Compound 1 is administered at a dosage of about 40.2 mg/kg. In some embodiments, Compound 1 is administered at a dosage of about 40.4 mg/kg. In some embodiments, Compound 1 is administered at a dosage of about 40.6 mg/kg. In some embodiments, Compound 1 is administered at a dosage of about 40.8 mg/kg.

In some embodiments, Compound 1 is administered at a dosage of about 41 mg/kg. In some embodiments, Compound 1 is administered at a dosage of about 41.2 mg/kg. In some embodiments, Compound 1 is administered at a dosage of about 41.4 mg/kg. In some embodiments, Compound 1 is administered at a dosage of about 41.6 mg/kg. In some embodiments, Compound 1 is administered at a dosage of about 41.8 mg/kg.

In some embodiments, Compound 1 is administered at a dosage of about 42 mg/kg. In some embodiments, Compound 1 is administered at a dosage of about 42.2 mg/kg. In some embodiments, Compound 1 is administered at a dosage of about 42.4 mg/kg. In some embodiments, Compound 1 is administered at a dosage of about 42.6 mg/kg. In some embodiments, Compound 1 is administered at a dosage of about 42.8 mg/kg.

In some embodiments, Compound 1 is administered at a dosage of about 43 mg/kg. In some embodiments, Compound 1 is administered at a dosage of about 43.2 mg/kg. In some embodiments, Compound 1 is administered at a dosage of about 43.4 mg/kg. In some embodiments, Compound 1 is administered at a dosage of about 43.6 mg/kg. In some embodiments, Compound 1 is administered at a dosage of about 43.8 mg/kg.

In some embodiments, Compound 1 is administered at a dosage of about 44 mg/kg. In some embodiments, Compound 1 is administered at a dosage of about 44.2 mg/kg. In some embodiments, Compound 1 is administered at a dosage of about 44.4 mg/kg. In some embodiments, Compound 1 is administered at a dosage of about 44.6 mg/kg. In some embodiments, Compound 1 is administered at a dosage of about 44.8 mg/kg.

In some embodiments, Compound 1 is administered at a dosage of about 45 mg/kg. In some embodiments, Compound 1 is administered at a dosage of about 45.2 mg/kg. In some embodiments, Compound 1 is administered at a dosage of about 45.4 mg/kg. In some embodiments, Compound 1 is administered at a dosage of about 45.6 mg/kg. In some embodiments, Compound 1 is administered at a dosage of about 45.8 mg/kg.

In some embodiments, Compound 1 is administered at a dosage of about 46 mg/kg. In some embodiments, Compound 1 is administered at a dosage of about 46.2 mg/kg. In some embodiments, Compound 1 is administered at a dosage of about 46.4 mg/kg. In some embodiments, Compound 1 is administered at a dosage of about 46.6 mg/kg. In some embodiments, Compound 1 is administered at a dosage of about 46.8 mg/kg.

In some embodiments, Compound 1 is administered at a dosage of about 47 mg/kg. In some embodiments, Compound 1 is administered at a dosage of about 47.2 mg/kg. In some embodiments, Compound 1 is administered at a dosage of about 47.4 mg/kg. In some embodiments, Compound 1 is administered at a dosage of about 47.6 mg/kg. In some embodiments, Compound 1 is administered at a dosage of about 47.8 mg/kg.

In some embodiments, Compound 1 is administered at a dosage of about 48 mg/kg. In some embodiments, Compound 1 is administered at a dosage of about 48.2 mg/kg. In some embodiments, Compound 1 is administered at a dosage of about 48.4 mg/kg. In some embodiments, Compound 1 is administered at a dosage of about 48.6 mg/kg. In some embodiments, Compound 1 is administered at a dosage of about 48.8 mg/kg.

In some embodiments, Compound 1 is administered at a dosage of about 49 mg/kg. In some embodiments, Compound 1 is administered at a dosage of about 49.2 mg/kg. In some embodiments, Compound 1 is administered at a dosage of about 49.4 mg/kg. In some embodiments, Compound 1 is administered at a dosage of about 49.6 mg/kg. In some embodiments, Compound 1 is administered at a dosage of about 49.8 mg/kg.

In some embodiments, Compound 1 is administered at a dosage of about 50 mg/kg. In some embodiments, Compound 1 is administered at a dosage of about 50.2 mg/kg. In some embodiments, Compound 1 is administered at a dosage of about 50.4 mg/kg. In some embodiments, Compound 1 is administered at a dosage of about 50.6 mg/kg. In some embodiments, Compound 1 is administered at a dosage of about 50.8 mg/kg.

In some embodiments, Compound 1 is administered at a dosage of about 51 mg/kg. In some embodiments, Compound 1 is administered at a dosage of about 51.2 mg/kg. In some embodiments, Compound 1 is administered at a dosage of about 51.4 mg/kg. In some embodiments, Compound 1 is administered at a dosage of about 51.6 mg/kg. In some embodiments, Compound 1 is administered at a dosage of about 51.8 mg/kg.

In some embodiments, Compound 1 is administered at a dosage of about 52 mg/kg. In some embodiments, Compound 1 is administered at a dosage of about 52.2 mg/kg. In some embodiments, Compound 1 is administered at a dosage of about 52.4 mg/kg. In some embodiments, Compound 1 is administered at a dosage of about 52.6 mg/kg. In some embodiments, Compound 1 is administered at a dosage of about 52.8 mg/kg.

In some embodiments, Compound 1 is administered at a dosage of about 53 mg/kg. In some embodiments, Compound 1 is administered at a dosage of about 53.2 mg/kg. In some embodiments, Compound 1 is administered at a dosage of about 53.4 mg/kg. In some embodiments, Compound 1 is administered at a dosage of about 53.6 mg/kg. In some embodiments, Compound 1 is administered at a dosage of about 53.8 mg/kg.

In some embodiments, Compound 1 is administered at a dosage of about 54 mg/kg. In some embodiments, Compound 1 is administered at a dosage of about 54.2 mg/kg. In some embodiments, Compound 1 is administered at a dosage of about 54.4 mg/kg. In some embodiments, Compound 1 is administered at a dosage of about 54.6 mg/kg. In some embodiments, Compound 1 is administered at a dosage of about 54.8 mg/kg.

In some embodiments, Compound 1 is administered at a dosage of about 55 mg/kg. In some embodiments, Compound 1 is administered at a dosage of about 55.2 mg/kg. In some embodiments, Compound 1 is administered at a dosage of about 55.4 mg/kg. In some embodiments, Compound 1 is administered at a dosage of about 55.6 mg/kg. In some embodiments, Compound 1 is administered at a dosage of about 55.8 mg/kg.

In some embodiments, Compound 1 is administered at a dosage of about 56 mg/kg. In some embodiments, Compound 1 is administered at a dosage of about 56.2 mg/kg. In some embodiments, Compound 1 is administered at a dosage of about 56.4 mg/kg. In some embodiments, Compound 1 is administered at a dosage of about 56.6 mg/kg. In some embodiments, Compound 1 is administered at a dosage of about 56.8 mg/kg.

In some embodiments, Compound 1 is administered at a dosage of about 57 mg/kg. In some embodiments, Compound 1 is administered at a dosage of about 57.2 mg/kg. In some embodiments, Compound 1 is administered at a dosage of about 57.4 mg/kg. In some embodiments, Compound 1 is administered at a dosage of about 57.6 mg/kg. In some embodiments, Compound 1 is administered at a dosage of about 57.8 mg/kg.

In some embodiments, Compound 1 is administered at a dosage of about 58 mg/kg. In some embodiments, Compound 1 is administered at a dosage of about 58.2 mg/kg. In some embodiments, Compound 1 is administered at a dosage of about 58.4 mg/kg. In some embodiments, Compound 1 is administered at a dosage of about 58.6 mg/kg. In some embodiments, Compound 1 is administered at a dosage of about 58.8 mg/kg.

In some embodiments, Compound 1 is administered at a dosage of about 59 mg/kg. In some embodiments, Compound 1 is administered at a dosage of about 59.2 mg/kg. In some embodiments, Compound 1 is administered at a dosage of about 59.4 mg/kg. In some embodiments, Compound 1 is administered at a dosage of about 59.6 mg/kg. In some embodiments, Compound 1 is administered at a dosage of about 59.8 mg/kg.

In some embodiments, Compound 1 is administered at a dosage of about 60 mg/kg.

In some embodiments, Compound 1 is administered once every seven days.

In some embodiments, Compound 1 is administered once every seven days for one week.

In some embodiments, Compound 1 is administered once every seven days for two weeks.

In some embodiments, Compound 1 is administered once every seven days for three weeks.

In some embodiments, Compound 1 is administered once every seven days for four weeks.

In some embodiments, Compound 1 is administered once every seven days for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

In some embodiments, Compound 1 is administered once every seven days followed by a dosing holiday.

In some embodiments, Compound 1 is administered twice every seven days.

In some embodiments, Compound 1 is administered twice every seven days for one week.

In some embodiments, Compound 1 is administered twice every seven days for two weeks.

In some embodiments, Compound 1 is administered twice every seven days for three weeks.

In some embodiments, Compound 1 is administered twice every seven days for four weeks.

In some embodiments, Compound 1 is administered twice every seven days for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

In some embodiments, Compound 1 is administered twice every seven days followed by a dosing holiday.

In some embodiments, Compound 1 is administered three times every seven days.

In some embodiments, Compound 1 is administered three times every seven days for one week.

In some embodiments, Compound 1 is administered three times every seven days for two weeks.

In some embodiments, Compound 1 is administered three times every seven days for three weeks.

In some embodiments, Compound 1 is administered three times every seven days for four weeks.

In some embodiments, Compound 1 is administered three times every seven days for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

In some embodiments, Compound 1 is administered three times every seven days followed by a dosing holiday.

In some embodiments, Compound 1 is administered once daily for two consecutive days followed by a five day dosing holiday.

In some embodiments, Compound 1 is administered once daily for two consecutive days followed by a five day dosing holiday for one week.

In some embodiments, Compound 1 is administered once daily for two consecutive days followed by a five day dosing holiday for two weeks.

In some embodiments, Compound 1 is administered once daily for two consecutive days followed by a five day dosing holiday for three weeks.

In some embodiments, Compound 1 is administered once daily for two consecutive days followed by a five day dosing holiday for four weeks.

In some embodiments, Compound 1 is administered once daily for two consecutive days followed by a five day dosing holiday for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

In some embodiments, Compound 1 is administered once daily for three consecutive days followed by a four day dosing holiday.

In some embodiments, Compound 1 is administered once daily for three consecutive days followed by a four day dosing holiday for one week.

In some embodiments, Compound 1 is administered once daily for three consecutive days followed by a four day dosing holiday for two weeks.

In some embodiments, Compound 1 is administered once daily for three consecutive days followed by a four day dosing holiday for three weeks.

In some embodiments, Compound 1 is administered once daily for three consecutive days followed by a four day dosing holiday for four weeks.

In some embodiments, Compound 1 is administered once daily for three consecutive days followed by a four day dosing holiday for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

In some embodiments, Compound 1 is administered once daily.

In some embodiments, Compound 1 is administered once daily for seven days.

In some embodiments, Compound 1 is administered once daily for two weeks.

In some embodiments, Compound 1 is administered once daily for three weeks.

In some embodiments, Compound 1 is administered once daily for four weeks.

In some embodiments, Compound 1 is administered once daily for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

In some embodiments, Compound 1 is administered once daily for seven days followed by a seven day dosing holiday.

In some embodiments, Compound 1 is administered once daily for seven days followed by a seven day dosing holiday for one month, two months, three months, four months, five months, six months, seven months, eight months, nine months, ten months, eleven months, or twelve months.

In some embodiments, Compound 1 is administered followed by a dosing holiday.

Use of Compound 1, or a pharmaceutically acceptable salt thereof, for the treatment of cancer in a subject in need thereof at a dosage of about 1.2 mg/kg once every seven days.

Use of Compound 1, or a pharmaceutically acceptable salt thereof, for the treatment of cancer in a subject in need thereof at a dosage of about 1.2 mg/kg once every seven days for one week.

Use of Compound 1, or a pharmaceutically acceptable salt thereof, for the treatment of cancer in a subject in need thereof at a dosage of about 1.2 mg/kg once every seven days for two weeks.

Use of Compound 1, or a pharmaceutically acceptable salt thereof, for the treatment of cancer in a subject in need thereof at a dosage of about 1.2 mg/kg once every seven days for three weeks.

Use of Compound 1, or a pharmaceutically acceptable salt thereof, for the treatment of cancer in a subject in need thereof at a dosage of about 1.2 mg/kg administered once every seven days for four weeks.

Use of Compound 1, or a pharmaceutically acceptable salt thereof, for the treatment of cancer in a subject in need thereof at a dosage of about 1.2 mg/kg once every seven days for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

Use of Compound 1, or a pharmaceutically acceptable salt thereof, for the treatment of cancer in a subject in need thereof at a dosage of about 1.2 mg/kg every seven days followed by a dosing holiday.

Use of Compound 1, or a pharmaceutically acceptable salt thereof, for the treatment of cancer in a subject in need thereof at a dosage of about 2.4 mg/kg once every seven days.

Use of Compound 1, or a pharmaceutically acceptable salt thereof, for the treatment of cancer in a subject in need thereof at a dosage of about 2.4 mg/kg once every seven days for one week.

Use of Compound 1, or a pharmaceutically acceptable salt thereof, for the treatment of cancer in a subject in need thereof at a dosage of about 2.4 mg/kg once every seven days for two weeks.

Use of Compound 1, or a pharmaceutically acceptable salt thereof, for the treatment of cancer in a subject in need thereof at a dosage of about 2.4 mg/kg once every seven days for three weeks.

Use of Compound 1, or a pharmaceutically acceptable salt thereof, for the treatment of cancer in a subject in need thereof at a dosage of about 2.4 mg/kg administered once every seven days for four weeks.

Use of Compound 1, or a pharmaceutically acceptable salt thereof, for the treatment of cancer in a subject in need thereof at a dosage of about 2.4 mg/kg once every seven days for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

Use of Compound 1, or a pharmaceutically acceptable salt thereof, for the treatment of cancer in a subject in need thereof at a dosage of about 2.4 mg/kg every seven days followed by a dosing holiday.

Use of Compound 1, or a pharmaceutically acceptable salt thereof, for the treatment of cancer in a subject in need thereof at a dosage of about 4.8 mg/kg once every seven days.

Use of Compound 1, or a pharmaceutically acceptable salt thereof, for the treatment of cancer in a subject in need thereof at a dosage of about 4.8 mg/kg once every seven days for one week.

Use of Compound 1, or a pharmaceutically acceptable salt thereof, for the treatment of cancer in a subject in need thereof at a dosage of about 4.8 mg/kg once every seven days for two weeks.

Use of Compound 1, or a pharmaceutically acceptable salt thereof, for the treatment of cancer in a subject in need thereof at a dosage of about 4.8 mg/kg once every seven days for three weeks.

Use of Compound 1, or a pharmaceutically acceptable salt thereof, for the treatment of cancer in a subject in need thereof at a dosage of about 4.8 mg/kg administered once every seven days for four weeks.

Use of Compound 1, or a pharmaceutically acceptable salt thereof, for the treatment of cancer in a subject in need thereof at a dosage of about 4.8 mg/kg once every seven days for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

Use of Compound 1, or a pharmaceutically acceptable salt thereof, for the treatment of cancer in a subject in need thereof at a dosage of about 4.8 mg/kg every seven days followed by a dosing holiday.

Use of Compound 1, or a pharmaceutically acceptable salt thereof, for the treatment of cancer in a subject in need thereof at a dosage of about 0.12 mg/kg once daily for seven days.

Use of Compound 1, or a pharmaceutically acceptable salt thereof, for the treatment of cancer in a subject in need thereof at a dosage of about 0.12 mg/kg once daily for seven days followed by a seven day dosing holiday.

Use of Compound 1, or a pharmaceutically acceptable salt thereof, for the treatment of cancer in a subject in need thereof at a dosage of about 0.24 mg/kg once daily for seven days.

Use of Compound 1, or a pharmaceutically acceptable salt thereof, for the treatment of cancer in a subject in need thereof at a dosage of about 0.24 mg/kg once daily for seven days followed by a seven day dosing holiday.

Use of Compound 1, or a pharmaceutically acceptable salt thereof, for the treatment of cancer in a subject in need thereof at a dosage of about 0.08 mg/kg once daily.

Use of Compound 1, or a pharmaceutically acceptable salt thereof, for the treatment of cancer in a subject in need thereof at a dosage of about 0.08 mg/kg once daily for seven days.

Use of Compound 1, or a pharmaceutically acceptable salt thereof, for the treatment of cancer in a subject in need thereof at a dosage of about 0.08 mg/kg once daily for two weeks.

Use of Compound 1, or a pharmaceutically acceptable salt thereof, for the treatment of cancer in a subject in need thereof at a dosage of about 0.08 mg/kg once daily for three weeks.

Use of Compound 1, or a pharmaceutically acceptable salt thereof, for the treatment of cancer in a subject in need thereof at a dosage of about 0.08 mg/kg once daily for four weeks.

Use of Compound 1, or a pharmaceutically acceptable salt thereof, for the treatment of cancer in a subject in need thereof at a dosage of about 0.08 mg/kg once daily for six weeks, eight weeks, 10 weeks, 12 weeks, 14 weeks, 16 weeks, 18 weeks, 20 weeks, 22 weeks, or 24 weeks.

Use of Compound 1, or a pharmaceutically acceptable salt thereof, for the treatment of cancer in a subject in need thereof at a dosage of about 0.08 mg/kg followed by a dosing holiday.

Use of Compound 1, or a pharmaceutically acceptable salt thereof, for the treatment of cancer in a subject in need thereof at a dosage of about 0.24 mg/kg once daily.

Use of Compound 1, or a pharmaceutically acceptable salt thereof, for the treatment of cancer in a subject in need thereof at a dosage of about 0.24 mg/kg once daily for seven days.

Use of Compound 1, or a pharmaceutically acceptable salt thereof, for the treatment of cancer in a subject in need thereof at a dosage of about 0.24 mg/kg once daily for two weeks.

Use of Compound 1, or a pharmaceutically acceptable salt thereof, for the treatment of cancer in a subject in need thereof at a dosage of about 0.24 mg/kg once daily for three weeks.

Use of Compound 1, or a pharmaceutically acceptable salt thereof, for the treatment of cancer in a subject in need thereof at a dosage of about 0.24 mg/kg once daily for four weeks.

Use of Compound 1, or a pharmaceutically acceptable salt thereof, for the treatment of cancer in a subject in need thereof at a dosage of about 0.24 mg/kg once daily for six weeks, eight weeks, 10 weeks, 12 weeks, 14 weeks, 16 weeks, 18 weeks, 20 weeks, 22 weeks, or 24 weeks.

Use of Compound 1, or a pharmaceutically acceptable salt thereof, for the treatment of cancer in a subject in need thereof at a dosage of about 0.24 mg/kg followed by a dosing holiday.

Use of Compound 1, or a pharmaceutically acceptable salt thereof, for the treatment of cancer in a subject in need thereof at a dosage of about 0.48 mg/kg once daily.

Use of Compound 1, or a pharmaceutically acceptable salt thereof, for the treatment of cancer in a subject in need thereof at a dosage of about 0.48 mg/kg once daily for seven days.

Use of Compound 1, or a pharmaceutically acceptable salt thereof, for the treatment of cancer in a subject in need thereof at a dosage of about 0.48 mg/kg once daily for two weeks.

Use of Compound 1, or a pharmaceutically acceptable salt thereof, for the treatment of cancer in a subject in need thereof at a dosage of about 0.48 mg/kg once daily for three weeks.

Use of Compound 1, or a pharmaceutically acceptable salt thereof, for the treatment of cancer in a subject in need thereof at a dosage of about 0.48 mg/kg once daily for four weeks.

Use of Compound 1, or a pharmaceutically acceptable salt thereof, for the treatment of cancer in a subject in need thereof at a dosage of about 0.48 mg/kg once daily for six weeks, eight weeks, 10 weeks, 12 weeks, 14 weeks, 16 weeks, 18 weeks, 20 weeks, 22 weeks, or 24 weeks.

Use of Compound 1, or a pharmaceutically acceptable salt thereof, for the treatment of cancer in a subject in need thereof at a dosage of about 0.48 mg/kg followed by a dosing holiday.

Use of Compound 1, or a pharmaceutically acceptable salt thereof, for the treatment of cancer in a subject in need thereof for seven consecutive days followed by a seven day dosing holiday at a dosage of about 0.12 mg/kg.

Use of Compound 1, or a pharmaceutically acceptable salt thereof, for the treatment of cancer in a subject in need thereof for seven consecutive days followed by a seven day dosing holiday at a dosage of about 0.24 mg/kg.

Use of Compound 1, or a pharmaceutically acceptable salt thereof, for the treatment of cancer in a subject in need thereof once daily at a dosage of about 0.08 mg/kg.

Use of Compound 1, or a pharmaceutically acceptable salt thereof, for the treatment of cancer in a subject in need thereof once daily at a dosage of about 0.24 mg/kg.

Use of Compound 1, or a pharmaceutically acceptable salt thereof, for the treatment of cancer in a subject in need thereof once daily at a dosage of about 0.48 mg/kg.

Use of a composition comprising Compound 1, or a pharmaceutically acceptable salt thereof, for the manufacture of a medicament for the treatment of cancer in a subject in need thereof at a dosage of about 1.2 mg/kg once every seven days.

Use of a composition comprising Compound 1, or a pharmaceutically acceptable salt thereof, for the manufacture of a medicament for the treatment of cancer in a subject in need thereof at a dosage of about 1.2 mg/kg once every seven days for one week.

Use of a composition comprising Compound 1, or a pharmaceutically acceptable salt thereof, for the manufacture of a medicament for the treatment of cancer in a subject in need thereof at a dosage of about 1.2 mg/kg once every seven days for two weeks.

Use of a composition comprising Compound 1, or a pharmaceutically acceptable salt thereof, for the manufacture of a medicament for the treatment of cancer in a subject in need thereof at a dosage of about 1.2 mg/kg once every seven days for three weeks.

Use of a composition comprising Compound 1, or a pharmaceutically acceptable salt thereof, for the manufacture of a medicament for the treatment of cancer in a subject in need thereof at a dosage of about 1.2 mg/kg administered once every seven days for four weeks.

Use of a composition comprising Compound 1, or a pharmaceutically acceptable salt thereof, for the manufacture of a medicament for the treatment of cancer in a subject in need thereof at a dosage of about 1.2 mg/kg once every seven days for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

Use of a composition comprising Compound 1, or a pharmaceutically acceptable salt thereof, for the manufacture of a medicament for the treatment of cancer in a subject in need thereof at a dosage of about 1.2 mg/kg every seven days followed by a dosing holiday.

Use of a composition comprising Compound 1, or a pharmaceutically acceptable salt thereof, for the manufacture of a medicament for the treatment of cancer in a subject in need thereof at a dosage of about 2.4 mg/kg once every seven days.

Use of a composition comprising Compound 1, or a pharmaceutically acceptable salt thereof, for the manufacture of a medicament for the treatment of cancer in a subject in need thereof at a dosage of about 2.4 mg/kg once every seven days for one week.

Use of a composition comprising Compound 1, or a pharmaceutically acceptable salt thereof, for the manufacture of a medicament for the treatment of cancer in a subject in need thereof at a dosage of about 2.4 mg/kg once every seven days for two weeks.

Use of a composition comprising Compound 1, or a pharmaceutically acceptable salt thereof, for the manufacture of a medicament for the treatment of cancer in a subject in need thereof at a dosage of about 2.4 mg/kg once every seven days for three weeks.

Use of a composition comprising Compound 1, or a pharmaceutically acceptable salt thereof, for the manufacture of a medicament for the treatment of cancer in a subject in need thereof at a dosage of about 2.4 mg/kg administered once every seven days for four weeks.

Use of a composition comprising Compound 1, or a pharmaceutically acceptable salt thereof, for the manufacture of a medicament for the treatment of cancer in a subject in need thereof at a dosage of about 2.4 mg/kg once every seven days for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

Use of a composition comprising Compound 1, or a pharmaceutically acceptable salt thereof, for the manufacture of a medicament for the treatment of cancer in a subject in need thereof at a dosage of about 2.4 mg/kg every seven days followed by a dosing holiday.

Use of a composition comprising Compound 1, or a pharmaceutically acceptable salt thereof, for the manufacture of a medicament for the treatment of cancer in a subject in need thereof at a dosage of about 4.8 mg/kg once every seven days.

Use of a composition comprising Compound 1, or a pharmaceutically acceptable salt thereof, for the manufacture of a medicament for the treatment of cancer in a subject in need thereof at a dosage of about 4.8 mg/kg once every seven days for one week.

Use of a composition comprising Compound 1, or a pharmaceutically acceptable salt thereof, for the manufacture of a medicament for the treatment of cancer in a subject in need thereof at a dosage of about 4.8 mg/kg once every seven days for two weeks.

Use of a composition comprising Compound 1, or a pharmaceutically acceptable salt thereof, for the manufacture of a medicament for the treatment of cancer in a subject in need thereof at a dosage of about 4.8 mg/kg once every seven days for three weeks.

Use of a composition comprising Compound 1, or a pharmaceutically acceptable salt thereof, for the manufacture of a medicament for the treatment of cancer in a subject in need thereof at a dosage of about 4.8 mg/kg administered once every seven days for four weeks.

Use of a composition comprising Compound 1, or a pharmaceutically acceptable salt thereof, for the manufacture of a medicament for the treatment of cancer in a subject in need thereof at a dosage of about 4.8 mg/kg once every seven days for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

Use of a composition comprising Compound 1, or a pharmaceutically acceptable salt thereof, for the manufacture of a medicament for the treatment of cancer in a subject in need thereof at a dosage of about 4.8 mg/kg every seven days followed by a dosing holiday.

Use of a composition comprising Compound 1, or a pharmaceutically acceptable salt thereof, for the manufacture of a medicament for the treatment of cancer in a subject in need thereof at a dosage of about 0.12 mg/kg once daily for seven days.

Use of a composition comprising Compound 1, or a pharmaceutically acceptable salt thereof, for the manufacture of a medicament for the treatment of cancer in a subject in need thereof at a dosage of about 0.12 mg/kg once daily for seven days followed by a seven day dosing holiday.

Use of a composition comprising Compound 1, or a pharmaceutically acceptable salt thereof, for the manufacture of a medicament for the treatment of cancer in a subject in need thereof at a dosage of about 0.24 mg/kg once daily for seven days.

Use of a composition comprising Compound 1, or a pharmaceutically acceptable salt thereof, for the manufacture of a medicament for the treatment of cancer in a subject in need thereof at a dosage of about 0.24 mg/kg once daily for seven days followed by a seven day dosing holiday.

Use of a composition comprising Compound 1, or a pharmaceutically acceptable salt thereof, for the manufacture of a medicament for the treatment of cancer in a subject in need thereof at a dosage of about 0.08 mg/kg once daily.

Use of a composition comprising Compound 1, or a pharmaceutically acceptable salt thereof, for the manufacture of a medicament for the treatment of cancer in a subject in need thereof at a dosage of about 0.08 mg/kg once daily for seven days.

Use of a composition comprising Compound 1, or a pharmaceutically acceptable salt thereof, for the manufacture of a medicament for the treatment of cancer in a subject in need thereof at a dosage of about 0.08 mg/kg once daily for two weeks.

Use of a composition comprising Compound 1, or a pharmaceutically acceptable salt thereof, for the manufacture of a medicament for the treatment of cancer in a subject in need thereof at a dosage of about 0.08 mg/kg once daily for three weeks.

Use of a composition comprising Compound 1, or a pharmaceutically acceptable salt thereof, for the manufacture of a medicament for the treatment of cancer in a subject in need thereof at a dosage of about 0.08 mg/kg once daily for four weeks.

Use of a composition comprising Compound 1, or a pharmaceutically acceptable salt thereof, for the manufacture of a medicament for the treatment of cancer in a subject in need thereof at a dosage of about 0.08 mg/kg once daily for six weeks, eight weeks, 10 weeks, 12 weeks, 14 weeks, 16 weeks, 18 weeks, 20 weeks, 22 weeks, or 24 weeks.

Use of a composition comprising Compound 1, or a pharmaceutically acceptable salt thereof, for the manufacture of a medicament for the treatment of cancer in a subject in need thereof at a dosage of about 0.08 mg/kg followed by a dosing holiday.

Use of a composition comprising Compound 1, or a pharmaceutically acceptable salt thereof, for the manufacture of a medicament for the treatment of cancer in a subject in need thereof at a dosage of about 0.24 mg/kg once daily.

Use of a composition comprising Compound 1, or a pharmaceutically acceptable salt thereof, for the manufacture of a medicament for the treatment of cancer in a subject in need thereof at a dosage of about 0.24 mg/kg once daily for seven days.

Use of a composition comprising Compound 1, or a pharmaceutically acceptable salt thereof, for the manufacture of a medicament for the treatment of cancer in a subject in need thereof at a dosage of about 0.24 mg/kg once daily for two weeks.

Use of a composition comprising Compound 1, or a pharmaceutically acceptable salt thereof, for the manufacture of a medicament for the treatment of cancer in a subject in need thereof at a dosage of about 0.24 mg/kg once daily for three weeks.

Use of a composition comprising Compound 1, or a pharmaceutically acceptable salt thereof, for the manufacture of a medicament for the treatment of cancer in a subject in need thereof at a dosage of about 0.24 mg/kg once daily for four weeks.

Use of a composition comprising Compound 1, or a pharmaceutically acceptable salt thereof, for the manufacture of a medicament for the treatment of cancer in a subject in need thereof at a dosage of about 0.24 mg/kg once daily for six weeks, eight weeks, 10 weeks, 12 weeks, 14 weeks, 16 weeks, 18 weeks, 20 weeks, 22 weeks, or 24 weeks.

Use of a composition comprising Compound 1, or a pharmaceutically acceptable salt thereof, for the manufacture of a medicament for the treatment of cancer in a subject in need thereof at a dosage of about 0.24 mg/kg followed by a dosing holiday.

Use of a composition comprising Compound 1, or a pharmaceutically acceptable salt thereof, for the manufacture of a medicament for the treatment of cancer in a subject in need thereof at a dosage of about 0.48 mg/kg once daily.

Use of a composition comprising Compound 1, or a pharmaceutically acceptable salt thereof, for the manufacture of a medicament for the treatment of cancer in a subject in need thereof at a dosage of about 0.48 mg/kg once daily for seven days.

Use of a composition comprising Compound 1, or a pharmaceutically acceptable salt thereof, for the manufacture of a medicament for the treatment of cancer in a subject in need thereof at a dosage of about 0.48 mg/kg once daily for two weeks.

Use of a composition comprising Compound 1, or a pharmaceutically acceptable salt thereof, for the manufacture of a medicament for the treatment of cancer in a subject in need thereof at a dosage of about 0.48 mg/kg once daily for three weeks.

Use of a composition comprising Compound 1, or a pharmaceutically acceptable salt thereof, for the manufacture of a medicament for the treatment of cancer in a subject in need thereof at a dosage of about 0.48 mg/kg once daily for four weeks.

Use of a composition comprising Compound 1, or a pharmaceutically acceptable salt thereof, for the manufacture of a medicament for the treatment of cancer in a subject in need thereof at a dosage of about 0.48 mg/kg once daily for six weeks, eight weeks, 10 weeks, 12 weeks, 14 weeks, 16 weeks, 18 weeks, 20 weeks, 22 weeks, or 24 weeks.

Use of a composition comprising Compound 1, or a pharmaceutically acceptable salt thereof, for the manufacture of a medicament for the treatment of cancer in a subject in need thereof at a dosage of about 0.48 mg/kg followed by a dosing holiday.

Use of a composition comprising Compound 1, or a pharmaceutically acceptable salt thereof, for the manufacture of a medicament for the treatment of cancer in a subject in need thereof for seven consecutive days followed by a seven day dosing holiday at a dosage of about 0.12 mg/kg.

Use of a composition comprising Compound 1, or a pharmaceutically acceptable salt thereof, for the manufacture of a medicament for the treatment of cancer in a subject in need thereof for seven consecutive days followed by a seven day dosing holiday at a dosage of about 0.24 mg/kg.

Use of a composition comprising Compound 1, or a pharmaceutically acceptable salt thereof, for the manufacture of a medicament for the treatment of cancer in a subject in need thereof once daily at a dosage of about 0.08 mg/kg.

Use of a composition comprising Compound 1, or a pharmaceutically acceptable salt thereof, for the manufacture of a medicament for the treatment of cancer in a subject in need thereof once daily at a dosage of about 0.24 mg/kg.

Use of a composition comprising Compound 1, or a pharmaceutically acceptable salt thereof, for the manufacture of a medicament for the treatment of cancer in a subject in need thereof once daily at a dosage of about 0.48 mg/kg.

In some embodiments, the subject is a mammal.

In some embodiments, the mammal is a human.

In some embodiments, the mammal is a rat. In some embodiments, the mammal is a mouse. In some embodiments, the mammal is a dog. In some embodiments, the mammal is a monkey.

Definitions

It is understood that Compound 1 may be identified with the IUPAC name of (S)-3-isobutyl-1-((S)-4-methyl-1-((S)-8-methyl-3-(pyrrolidin-1-ylmethyl)-1,5-dioxa-9-azaspiro[5.5]undecan-9-yl)-1-oxopentan-2-yl)piperazin-2-one and/or the following chemical structure:

(Compound 1)

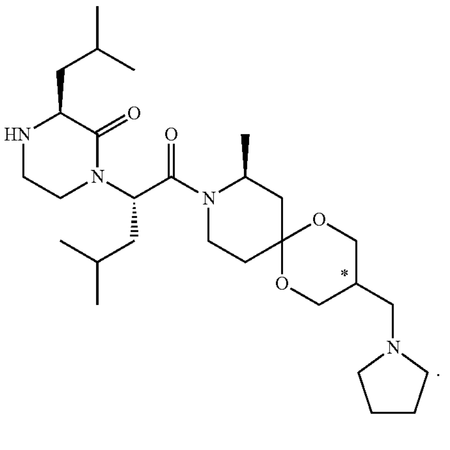

In some embodiments, Compound 1 is a methanesulfonic acid salt (mesylate).

It is understood that Compound 1' may be identified with the name (S)-3-isobutyl-1-((S)-4-methyl-1-((3R,6s,8S)-8-methyl-3-(pyrrolidin-1-ylmethyl)-1,5-dioxa-9-azaspiro[5.5]undecan-9-yl)-1-oxopentan-2-yl)piperazin-2-one, (S)-1-[(S)-1-({(S)-8-Methyl-3-[(1-pyrrolidinyl)methyl]-1,5-dioxa-9-aza-9-spiro[5.5]undecyl}carbonyl)-3-methylbutyl]-3-isobutyl-2-piperazinone, (3S)-1-[(2S)-4-methyl-1-oxo-1-[(3s,6s,8S)-8-methyl-3-(pyrrolidin-1-ylmethyl)-1,5-dioxa-9-azaspiro[5.5]undecan-9-yl]pentan-2-yl]-3-(2-methylpropyl)piperazin-2-one, and/or the following chemical structure:

(Compound 1')

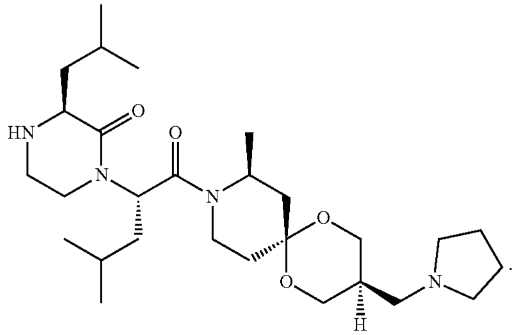

In some embodiments, Compound 1' is a methanesulfonic acid salt (mesylate).

In some embodiments, Compound 1 is Compound 1'.

In some embodiments, Compound 1, as disclosed in any one of Examples 1-7, is Compound 1'.

The dosages provided in the animal studies presented herein (e.g., Examples 2, 4-5, and 7) may be scaled to human adults or to children of various ages using known equivalents, for example, as shown below in Table A or B (reproduced from "Guidance for Industry Estimating the Maximum Safe Starting Dose in Initial Clinical Trials for Therapeutics in Adult Healthy Volunteers", U.S. Department of Health and Human Services, Food and Drug Administration, Center for Drug Evaluation and Research (CDER), July 2005, Pharmacology and Toxicology, the contents of which are incorporated by reference herein in their entirety).

TABLE A

Conversion of Animal Doses to Human Equivalent Doses Based on Body Surface Area

| Species | To Convert Animal Dose in mg/kg to Dose in mg/m$^2$, Multiply by $k_m$ | To Convert Animal Dose in mg/kg to HED[a] in mg/kg, Either: Divide Animal Dose By | Multiply Animal Dose By |
|---|---|---|---|
| Human | 37 | — | — |
| Child (20 kg)[b] | 25 | — | — |
| Mouse | 3 | 12.3 | 0.08 |
| Hamster | 5 | 7.4 | 0.13 |
| Rat | 6 | 6.2 | 0.16 |
| Ferret | 7 | 5.3 | 0.19 |
| Guinea pig | 8 | 4.6 | 0.22 |
| Rabbit | 12 | 3.1 | 0.32 |
| Dog | 20 | 1.8 | 0.54 |
| Primates: | | | |
| Monkeys[c] | 12 | 3.1 | 0.32 |
| Marmoset | 6 | 6.2 | 0.16 |
| Squirrel monkey | 7 | 5.3 | 0.19 |
| Baboon | 20 | 1.8 | 0.54 |
| Micro-pig | 27 | 1.4 | 0.73 |
| Mini-pig | 35 | 1.1 | 0.95 |

[a]Assumes 60 kg human. For species not listed or for weights outside the standard ranges, HED can be calculated from the following formula: HED = animal dose in mg/kg × (animal weight in kg/human weight in kg)$^{0.33}$.

[b]This $k_m$ value is provided for reference only since healthy children will rarely be volunteers for phase 1 trials.

[c]For example, cynomolgus, rhesus, and stumptail.

TABLE B

Effect of Allometric Exponent on Conversion Factor[a]

| Species | Weight Range[b] (kg) | Conversion Factors[c] Standard | b = 0.67 | b = 0.75 | Ratio of 0.75 to 0.67 |
|---|---|---|---|---|---|
| Mouse | 0.018-0.033 | 0.081 | 0.075 | 0.141 | 1.88 |
| Rat | 0.09-0.40 | 0.162 | 0.156 | 0.245 | 1.57 |
| Rabbit | 1.5-3 | 0.324 | 0.33 | 0.43 | 1.30 |
| Monkey | 1.5-4 | 0.324 | 0.37 | 0.47 | 1.27 |
| Dog | 6.5-13.0 | 0.541 | 0.53 | 0.62 | 1.17 |

[a]conversion factor = $(W_{animal}/W_{human})^{(1-b)}$

[b]human weight range used was 50-80 kg (110-176 lb)

[c]mean conversion factor calculated across entire animal weight range and human weight range As disclosed herein, the dosage unit "mg/kg" refers to mass of the therapeutic agent (e.g., Compound 1 or Compound 1', expressed in mg) administered to the subject per unit mass of the subject (e.g., the body weight of the subject, expressed in kg).

Compounds having one or more chiral centers can exist in various stereoisomeric forms. Stereoisomers are compounds that differ only in their spatial arrangement. Stereoisomers include all diastereomeric, enantiomeric, and epimeric forms as well as racemates and mixtures thereof.

The term "geometric isomer" refers to cyclic compounds having at least two substituents, wherein the two substituents are both on the same side of the ring (cis) or wherein the substituents are each on opposite sides of the ring (trans). When a disclosed compound is named or depicted by structure without indicating stereochemistry, it is understood that the name or the structure encompasses one or more of the possible stereoisomers, or geometric isomers, or a mixture of the encompassed stereoisomers or geometric isomers.

When a geometric isomer is depicted by name or structure, it is to be understood that the named or depicted isomer exists to a greater degree than another isomer, that is that the geometric isomeric purity of the named or depicted geometric isomer is greater than 50%, such as at least 60%, 70%, 80%, 90%, 99%, or 99.9% pure by weight. Geometric isomeric purity is determined by dividing the weight of the named or depicted geometric isomer in the mixture by the total weight of all of the geometric isomers in the mixture.

Racemic mixture means 50% of one enantiomer and 50% of is corresponding enantiomer. When a compound with one chiral center is named or depicted without indicating the stereochemistry of the chiral center, it is understood that the name or structure encompasses both possible enantiomeric forms (e.g., both enantiomerically-pure, enantiomerically-enriched or racemic) of the compound. When a compound with two or more chiral centers is named or depicted without indicating the stereochemistry of the chiral centers, it is understood that the name or structure encompasses all possible diastereomeric forms (e.g., diastereomerically pure, diastereomerically enriched and equimolar mixtures of one or more diastereomers (e.g., racemic mixtures) of the compound.

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers also can be obtained from diastereomerically- or enantiomerically-pure intermediates, reagents, and catalysts by well-known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers is included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

As used herein, the term "subject" refers to an organism, for example, a mammal (e.g., a human, a non-human mammal, a non-human primate, a primate, a laboratory animal, a mouse, a rat, a hamster, a gerbil, a cat, a dog). In some embodiments a human subject is an adult, adolescent, or pediatric subject (a child). In some embodiments, a subject is suffering from a disease, disorder or condition, e.g., a disease, disorder or condition that can be treated as provided herein, e.g., a cancer or a tumor listed herein. In some embodiments, a subject displays one or more symptoms of a disease, disorder or condition. In some embodiments, a subject does not display a particular symptom (e.g., clinical manifestation of disease) or characteristic of a disease, disorder, or condition. In some embodiments, a subject does not display any symptom or characteristic of a disease, disorder, or condition. In some embodiments, a subject is a patient. In some embodiments, a subject is an individual to whom diagnosis and/or therapy is and/or has been administered.

As used herein, a "first line therapy" refers to the first treatment given for a cancer. It is often part of a standard set of treatments, such as surgery followed by chemotherapy and radiation. When used by itself, first-line therapy is usually the one accepted as the best treatment. A "second line therapy" refers to the second treatment given for the disease. First and second line therapies will depend upon the particular cancer, and will be known to persons of ordinary skill in the art.

As used herein, a "relapsed" cancer refers to a cancer has recurred (come back), usually after a period of time during which the cancer could not be detected. The cancer may come back to the same place as the original (primary) tumor or to another place in the body. For example, a cancer may not be detectable for a period of time after administration of a first or second line therapy to a subject, but then relapse.

As used herein, the term "gene" has its meaning as understood in the art. However, it will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules such as long non-coding RNAs (lncRNAs). For clarity, the term gene generally refers to a portion of a nucleic acid that encodes a protein; the term may optionally encompass regulatory sequences. This definition is not intended to exclude application of the term "gene" to non-protein coding expression units but rather to clarify that, in most cases, the term as used in this document refers to a protein coding nucleic acid. In some cases, the gene includes regulatory sequences involved in transcription, or message production or composition. In other embodiments, the gene comprises transcribed sequences that encode for a protein, polypeptide or peptide. In particular embodiments, the transcribed nucleotide sequence comprises at least one functional protein, polypeptide and/or peptide encoding unit. As will be understood by those in the art, this functional term "gene" includes both genomic sequences, RNA or cDNA sequences, or smaller engineered nucleic acid segments, including nucleic acid segments of a non-transcribed part of a gene, including but not limited to the non-transcribed promoter or enhancer regions of a gene. The sequences which are located 5' of the coding region and which are present on the mRNA are referred to as 5' untranslated sequences ("5'UTR"). The sequences which are located 3' or downstream of the coding region and which are present on the mRNA are referred to as 3' untranslated sequences, or ("3'UTR").

As used herein, the term "pathway" is intended to mean a set of system components involved in two or more sequential molecular interactions that result in the production of a product or activity. A pathway can produce a variety of products or activities that can include, for example, intermolecular interactions, changes in expression of a nucleic acid or polypeptide, the formation or dissociation of a complex between two or more molecules, accumulation or destruction of a metabolic product, activation or deactivation of an enzyme or binding activity. Thus, the term "pathway" includes a variety of pathway types, such as, for example, a biochemical pathway, a gene expression pathway, and a regulatory pathway. Similarly, a pathway can include a combination of these exemplary pathway types.

As used herein the term "modulation" includes the inhibition of one or more functions of CBP/p300, the increase in one or more functions of CBP/p300, or a qualitative change in one or more functions of CBP/p300.

The term "pharmaceutically acceptable salt" refers to a pharmaceutical salt that is, within the scope of sound medical judgment, suitable for use in contact with the tissues of humans and lower animals without undue toxicity, irritation, and allergic response, and is commensurate with a reasonable benefit/risk ratio. Pharmaceutically acceptable salts are well known in the art. For example, S. M. Berge et al. describes pharmacologically acceptable salts in *J. Pharm. Sci.,* 1977, 66, 1-19.

Included in the present teachings are pharmaceutically acceptable salts of Compound 1. Compounds having basic groups can form pharmaceutically acceptable salts with pharmaceutically acceptable acid(s). Suitable pharmaceutically acceptable acid addition salts of the compounds described herein include salts of inorganic acids (such as hydrochloric acid, hydrobromic acid, phosphoric acid, metaphosphoric acid, nitric acid, and sulfuric acid) and of organic acids (such as acetic acid, benzenesulfonic acid, benzoic acid, citric acid, ethanesulfonic acid, methanesulfonic acid (mesylate), succinic acid, and trifluoroacetic acid). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts). In some embodiments, Compound 1 is a citric acid salt. In some embodiments, Compound 1 is a methanesulfonic acid salt (mesylate).

Unless explicitly indicated otherwise, the terms "approximately" and "about" are synonymous. In one embodiment, "approximately" and "about" refer to the recited amount, value, or duration ±5%, ±4.5%, ±4%, ±3.5%, ±3%, ±2.5%, ±2%, ±1.75%, 1.5%, 1.25%, ±1%, ±0.9%, ±0.8%, ±0.7%, ±0.6%, ±0.5% ±0.4%, ±0.3%, ±0.2%, ±0.1%, ±0.09%, ±0.08%, ±0.07%, 0.06%, ±0.05%, 0.04%, 0.03%, 0.02%, or ±0.01%. In another embodiment, "approximately" and "about" refer to the listed amount, value, or duration ±2.5%, ±2%, 1.75%, 1.5%, 1.25%, ±1%, ±0.9%, ±0.8%, ±0.7%, ±0.6%, ±0.5%. In yet another embodiment, "approximately" and "about" refer to the listed amount, value, or duration ±1%. In yet another embodiment, "approximately" and "about" refer to the listed amount, value, or duration ±0.5%. In yet another embodiment, "approximately" and "about" refer to the listed amount, value, or duration A0.1.

Pharmaceutical Compositions

The pharmaceutical composition of the present disclosure comprises Compound 1, or a pharmaceutically acceptable salt, hydrate, solvate or stereoisomer thereof, and a pharmaceutically acceptable carrier or diluent.

"Pharmaceutically acceptable carrier" and "pharmaceutically acceptable diluent" refer to a substance that aids the formulation and/or administration of an active agent to and/or absorption by a subject and can be included in the compositions of the present disclosure without causing a significant adverse toxicological effect on the subject. Non-limiting examples of pharmaceutically acceptable carriers and/or diluents include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds.

The pharmaceutical compositions of the present teachings optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients ($5^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

The term "dosage holiday", also referred to as "drug holiday" or "dosing holiday," refers to a period of time wherein the subject is not administered or administered at a lower dosage the therapeutic. The timing of a dosage holiday depends on the timing of the regular dosing regimen and the purpose for taking the dosage holiday (e.g., to regain drug sensitivity and/or to reduce unwanted side effects of continuous, long-term administration). In some embodiments, the dosage holiday may be a reduction in the dosage of the drug (e.g., to below the therapeutically effective amount for a certain interval of time). In other embodiments, administration of the dosage is stopped for a certain interval of time before resuming administration of the same or different dosing regimen (e.g., at a lower or higher dose and/or frequency of administration). A dosage holiday of the disclosure may thus be selected from a wide range of time-periods and dosage regimens.

In some embodiments, the pharmaceutical composition is formulated for oral administration.

In some embodiments, the pharmaceutical composition is formulated for intravenous administration.

Methods of Administration and Dosage Forms

The precise amount of compound administered to provide an "effective amount" to the subject will depend on the mode of administration, the type, and severity of the disease, and on the characteristics of the subject, such as general health, age, sex, body weight, and tolerance to drugs. The skilled artisan will be able to determine appropriate dosages depending on these and other factors. When administered in combination with other therapeutic agents, e.g., when administered in combination with an anti-cancer agent, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound of the disclosure being used by following, for example, dosages reported in the literature and recommended in the *Physician's Desk Reference* (57th ed., 2003).

The term "effective amount" means an amount when administered to the subject which results in beneficial or desired results, including clinical results, e.g., inhibits, suppresses or reduces the symptoms of the condition being treated in the subject as compared to a control. For example, a therapeutically effective amount can be given in unit dosage form (e.g., 0.1 mg to about 50 g per day, alternatively from 1 mg to about 5 grams per day).

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa.

In addition, the disclosed compound can be co-administered with other therapeutic agents. As used herein, the terms "co-administration", "administered in combination with", and their grammatical equivalents, are meant to encompass administration of two or more therapeutic agents to a single subject, and are intended to include treatment regimens in which the agents are administered by the same or different route of administration or at the same or different times. In some embodiments the one or more compounds described herein will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, the compounds described herein and the other agent(s) are admixed in the composition.

The particular mode of administration and the dosage regimen will be selected by the attending clinician, taking into account the particulars of the case (e.g., the subject, the disease, the disease state involved, the particular treatment). Treatment can involve daily or multi-daily or less than daily (such as weekly or monthly etc.) doses over a period of a few days to months, or even years. However, a person of ordinary skill in the art would immediately recognize appropriate and/or equivalent doses looking at dosages of approved compositions for treating cancer using the disclosed compound for guidance.

The compounds or the corresponding pharmaceutical compositions taught herein can be administered to a patient in a variety of forms depending on the selected route of administration, as will be understood by those skilled in the art. The compounds of the present teachings may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

In some embodiments, Compound 1 or a pharmaceutical composition comprising Compound 1 is administered orally. In some embodiments, Compound 1 or a pharmaceutical composition comprising Compound 1 is administered intravenously. In some embodiments, Compound 1 or a pharmaceutical composition comprising Compound 1 is administered via injection or infusion.

The pharmaceutical composition of the disclosure is formulated to be compatible with its intended route of administration. In an embodiment, the composition is formulated in accordance with routine procedures as a pharmaceutical composition adapted for intravenous, subcutaneous, intramuscular, oral, intranasal, or topical administration to human beings. In preferred embodiments, the pharmaceutical composition is formulated for intravenous administration.

Typically, for oral therapeutic administration, a compound of the present teachings may be incorporated with excipient and used in the form of ingestible tablets, buccal tablets, troches, capsules, elixirs, suspensions, syrups, wafers, and the like.

Typically for parenteral administration, solutions of a compound of the present teachings can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound described herein for the extemporaneous preparation of sterile injectable solutions or dispersions are appropriate.

In some embodiments, Compound 1 or a pharmaceutical composition comprising Compound 1 for use in accordance with the present disclosure is formulated, dosed, and/or administered in a therapeutically effective amount using pharmaceutical compositions and dosing regimens that are consistent with good medical practice and appropriate for the relevant agent(s) and subject(s).

Factors to be considered when optimizing routes and/or dosing schedule for a given therapeutic regimen may include, for example, the particular indication being treated, the clinical condition of a subject (e.g., age, overall health, prior therapy received and/or response thereto) the site of delivery of the agent, the nature of the agent (e.g. an antibody or other polypeptide-based compound), the mode and/or route of administration of the agent, the presence or absence of combination therapy, and other factors known to medical practitioners. For example, in the treatment of cancer, relevant features of the indication being treated may include, for example, one or more of cancer type, stage, location.

In some embodiments, one or more features of a particular pharmaceutical composition and/or of a utilized dosing regimen may be modified over time (e.g., increasing or decreasing the amount of active agent in any individual dose, increasing or decreasing time intervals between doses), for example in order to optimize a desired therapeutic effect or response (e.g., inhibition or modulation of a p300 gene or gene product).

In general, type, amount, and frequency of dosing of Compound 1 or a pharmaceutical composition comprising Compound 1 are governed by safety and efficacy requirements that apply when one or more relevant agent(s) is/are administered to a mammal (e.g., a human).

One of skill in the art can select from a variety of administration regimens and will understand that an effective amount of a particular a compound or pharmaceutical composition of the disclosure may be dependent on the subject being treated, on the subject's weight, the severity of the affliction, the manner of administration and/or the judgment of the prescribing physician.

Cancers

Cancer is a disease caused by the uncontrolled division of cells in the body. Abnormally dividing cancer cells can form a primary tumor, which can then invade nearby tissues, and spread throughout the body through the blood and lymphatic systems (metastatic cancers). Cancer can arise from many organs and cell types in the body, including but not limited to, cells of the lymphatic system, bone marrow, blood, brain and nervous system tissue, breast, cervix, ovary, colorectal cells, stomach and gastric cells, head and neck, kidney, liver, lung, oesophagus, pancreas, prostate and skin.

As used herein, the term "tumor" refers to an abnormal growth of cells or tissue. In some embodiments, a tumor may comprise cells that are precancerous (e.g., benign), malignant, pre-metastatic, metastatic, and/or non-metastatic. In some embodiments, a tumor is associated with, or is a manifestation of, a cancer.

In some embodiments, a tumor may be a disperse tumor or a liquid tumor. Liquid tumors can affect bone marrow, blood cells and the lymphatic system. Exemplary liquid tumors include leukemias and lymphomas. Types of lymphomas include, but are not limited to, Hodgkin lymphomas, non-Hodgkin lymphomas, B cell lymphomas, T-cell lymphomas, Burkitt's lymphomas, mantle cell lymphomas, small lymphocytic lymphomas, histiocytic lymphomas and primary mediastinal B cell lymphomas. Types of leukemias include, but are not limited to, acute myeloid leukemia, T cell leukemias, acute lymphoblastic leukemias and chronic myelogenous leukemias.

In some embodiments, a tumor may be a solid tumor. Exemplary solid tumors include, but are not limited to Carcinomas, Sarcomas, Myelomas, germ cell tumors, carcinoid tumors, neuroendocrine tumors and tumors of mixed type (a tumor which comprises multiple types of cancer cells). Carcinomas arise from epithelial tissues, either internal or external, such as cells of the gastrointestinal tract. Exemplary carcinomas include adenocarcinoma, which develops in an organ or gland, and squamous cell carcinoma, which originates in the squamous epithelium. Sarcomas are cancers that originate in supportive or connective tissues such as bones, tendons, cartilage, muscle and fat. Exemplary sarcomas include osteosarcoma, chondrosarcoma, leiomyosarcoma, rhabdomyosarcoma, mesothelial sarcoma, fibrosarcoma, angiosarcoma, liposarcoma, glioma or astrocytoma, myxosarcoma and mesenchymous or mixed mesodermal tumors.

Tumors can arise from most organs and tissue in the body, including, but not limited to, brain and nervous tissue, breast, cervix, ovary, uterus, colorectal, stomach and gastric tissue, kidney, liver, lung oesophagus, pancreas, prostate, skin, bone, head and neck, and lung. Exemplary brain and nervous system cancers include neurogliomas and glioblastomas. Exemplary breast cancers include human breast carcinomas, breast adenocarcinomas and invasive ductal carcinomas. Exemplary cervical cancers include epidermoid carcinomas, cervical carcinomas and HPV positive cervical cancers. Exemplary ovarian cancers include ovarian carcinomas. Exemplary colorectal cancers include colorectal carcinomas and colon colorectal adenocarcinomas. Exemplary stomach and gastric cancers include gastric adenocarcinomas, stomach adenocarcinomas and gastric carcinomas. Exemplary kidney cancers include renal cell adenocarcinomas and kidney clear cell carcinomas. Exemplary liver cancers include hepatocellular carcinomas and hepatomas. Exemplary lung cancers include small cell lung cancers, non-small cell lung cancers, lung carcinomas, lung adenocarcinomas, squamous cell carcinomas and large cell carcinomas. Exemplary esophageal cancers include esophageal squamous cell carcinoma. Exemplary pancreatic cancers include pancreatic carcinoma and pancreatic ductal adenocarcinoma. Exemplary prostate cancers include prostate carcinomas, prostate adenocarcinomas and castrate resistant prostate cancers. Exemplary skin cancers include melanomas, squamous cell carcinomas and basal cell carcinomas. Exemplary head and neck cancers include squamous cell carcinomas.

Cancers that can be treated by Compound 1 of the disclosure include cancers that are deficient in DNA repair.

Cancers that can be treated by Compound 1 of the disclosure include cancers where cells of the cancer express CBP, p300, or a combination thereof.

Cancers that can be treated by Compound 1 of the disclosure include cancers where cells of the have lost expression or function of p53, Rb or a combination thereof Exemplary cancers that undergo frequent loss of p53 and/or Rb pathway expression or function include, but are not limited to, prostate cancer and small cell lung cancer.

Cancers that can be treated by Compound 1 of the disclosure include cancers that have relapsed after treatment with a first and/or second line therapy for the cancer, or which were unresponsive or only partially responsive to a first and/or second line therapy for the cancer. For example, subjects with prostate cancer who were previously treated with anti-androgen therapy such as enzalutamide, abiraterone, daralutamide, apalutamide, and taxane, are envisaged as within the scope of the instant disclosure. As a further example, subjects with prostate or small cell lung cancer (SCLC) who have been treated with a prior chemotherapy are also envisaged as within the scope of the instant disclosure.

Cancers that can be treated by Compound 1 of the disclosure include advanced stage cancers. In some embodiments, the cancer is a Stage II cancer. In some embodiments, the cancer is a Stage III cancer. In some embodiments, the cancer is a Stage IV cancer. In some embodiments, the cancer is metastatic cancer.

In some embodiments, the cancer is associated with lineage plasticity. As used herein, "lineage plasticity" refers to a process by which differentiated cells can display plasticity by changing their identity, either by dedifferentiation to a progenitor-like state or by transdifferentiation to an alternative differentiated cell type. Exemplary cancers that exhibit lineage plasticity include castrate resistant prostate cancer (CRPC), in which CRPC tumors with neuroendocrine features evolve from CRPC tumors with adenocarcinoma-like features. Lineage plasticity of CRPC tumors is associated with the development of resistance to androgen receptor based cancer therapies. Additional cancers thought to exhibit lineage plasticity include, but are not limited to breast cancer, small cell lung cancer and melanoma. Lineage plasticity may also be associated with Rb dysfunction in cancer cells. In one model of the evolution of CRPC, loss of Rb1, even late in cancer progression, lead to both an increase in androgen receptor (AR) levels, which was mediated by E2F1, and an increase in AR target gene expression.

In some embodiments, the cancer is pancreatic cancer, osteosarcoma, gastric cancer, prostate cancer, breast cancer, small cell lung cancer, adenocarcinoma, melanoma or neuroendocrine cancer.

In some embodiments, the cancer is pancreatic cancer, osteosarcoma, gastric cancer, prostate cancer, breast cancer, small cell lung cancer, adenocarcinoma, neuroendocrine cancer, or melanoma or lymphoma.

One type of cancer which can be treated using Compound 1 of the disclosure is prostate cancer, for example castrate resistant prostate cancer (CRPC). In US and EU, prostate cancer (PC) is the most common malignancy in men. Despite high cure rates after prostatectomy or radiation therapy or both, a proportion of patients will suffer disease relapse. Men who experience rising values of prostate specific antigen (PSA) after therapy for localized PC may be offered androgen deprivation treatment (ADT). This typically induces PSA declines, but eventually, virtually all patients develop CRPC, characterized by rising levels of PSA despite castrate levels of testosterone, in the absence or presence of radiographic evidence of distant metastatic disease. Blockade of biosynthesis of androgenic hormones with abiraterone or next generation androgen-antagonists such as enzalutamide are combined with ADT and represent the standard of care for metastatic CRPC. Although management of advanced/metastatic PC obtained the approvals of several new agents over the last years, the general principles of these therapeutics, i.e., inhibition of the androgen receptor (AR) and taxane based chemotherapy regimens, still comprise the main treatment options. Acquired resistance to therapy in CRPC is multifactorial. Disease progression following first-line ADT is typically associated with re-activation of AR signaling mediated by mutation, amplification or structural rearrangement of the AR gene itself. For these patients, treatment with next generation AR signaling inhibitors has shown to provide clinical benefit and prolongation of life. However, with an increasingly earlier use of such more potent and newer drugs targeting the AR, AR-indifferent PC has emerged as a clinically distinct entity, frequently displaying a combined Rb/p53 loss-of-function which was identified to be associated with shortest overall survival (OS) in CRPC. AR-indifferent PC has emerged as a clinically distinct entity. It is associated with low AR signaling, combined Rb/p53 loss-of-function, loss of luminal prostate markers and trans-differentiation leading to small cell neuroendocrine (NE) features through a process termed lineage plasticity, i.e., the ability of cells to transition from one committed developmental pathway to another. Such treatment-emergent NE-prostate cancer (NEPC) is described in later stages of PC progression in up to 15-20% of patients. Androgen deprivation increases p300 expression and advanced CRPC frequently exhibits combined loss of Rb/p53 function.

As a crucial coactivator of androgen receptor (AR) signaling, p300 has been associated with tumor progression and poor prognosis in prostate cancer. p300 expression is increased upon androgen deprivation treatment (ADT) and docetaxel treatment. In CRPC, combined loss of Rb and p53 is a frequent event in resistance development to AR-pathway inhibitors and indicative of lineage plasticity. In CRPC, Compound 1 of the disclosure has been found to be efficacious at all levels of lineage plasticity, and to trigger tumor regression in multi-drug resistant patient-derived xenograft models.

In some embodiments, the prostate cancer is resistant to androgen receptor (AR) pathway inhibitors. Exemplary AR pathway inhibitors include, but are not limited to, abiraterone acetate, enzalutamide, apalutamide, darolutamide or bicalutamide. In some embodiments, the prostate cancer is neuroendocrine prostate cancer. In some embodiments, the prostate cancer is adenocarcinoma prostate cancer.

In some embodiments, the prostate cancer is the prostate cancer is neuroendocrine prostate cancer (NEPC).

In some embodiments, the prostate cancer is the prostate cancer is AR negative (AR−), androgen independent prostate cancer.

In some embodiments, the prostate cancer is androgen driven, AR positive adenocarcinoma.

In some embodiments, the prostate cancer comprises both AR positive and AR negative cells.

Further types of cancers which can be treated using Compound 1 include hematological cancers. Changes in p53, RB1, ASXL1, RUNX1, and paralogs of ASXL1 and RUNX1, are correlated with the susceptibility hematological cancers to the compounds of the disclosure. In some embodiments, changes in p52, ASXL1, RUNX1, and paralogs of ASXL1 and RUNX1, are correlated with the susceptibility of hematological cancers to Compound 1.

In some embodiments, the cancer is a hematological cancer. In some embodiments, the hematological cancer is acute lymphocytic leukemia (ALL), acute myeloid leukemia (AML), B cell lymphoma (BCL), chronic lymphocytic leukemia (CLL), chronic myeloid leukemia (CML), diffuse large B cell lymphoma (DLBCL), Epstein Barr driven hematological cancer, multiple myeloma (MM), T cell lymphoma (TCL), Hodgkin lymphoma or non-Hodgkin lymphoma. In some embodiments, the hematological cancer is ALL, AML, DLBCL, or MM.

In some embodiments, the cancer comprises a liquid tumor or a solid tumor.

In some embodiments, the cancer is prostate cancer, renal cancer, pancreatic cancer, liver cancer, breast cancer, gastric cancer, colon cancer, cervical cancer, ovarian cancer, head-and-neck cancer, esophageal cancer, leukemia, lymphoma, lung cancer, brain cancer, stomach cancer, cancer of the central nervous system, or skin cancer.

In some embodiments, the cancer is lung cancer, gastric cancer, prostate cancer, or colon cancer.

Further types of cancers which can be treated using Compound 1 include small cell lung cancer. Small cell lung cancer accounts for approximately 15% of all lung cancer and is the leading cause of cancer death among men and the second leading cause of cancer death among women worldwide. The prognosis of patients with SCLC is dismal with a 5-year survival rate of less than 5% and an average overall survival (OS) period of only 2-4 months for patients not receiving any active treatment. Expression of p300 and CBP in SCLC is associated with poor prognosis, with high p300 and CBP expressions being independent prognostic markers of poor OS for resected SCLC patients. Moreover, SCLC displays a combined loss-of-function of Rb1 and p53 at a very high frequency, which renders SCLC particularly sensitive to Compound 1.

Therapeutic options for SCLC are limited and have not changed substantially during the past two decades. Currently, chemotherapy (platinum plus etoposide) remains the standard treatment for first-line management of SCLC. Only recently, immunotherapeutic drugs (atezolizumab and durvalumab) have made their entry into treatment of SCLC in 1st line. When patients with SCLC relapse, few therapeutic options are available. Until recently, topotecan was the only approved drug for second-line treatment of patients with a chemotherapy-free interval longer than 60 days with relatively modest clinical benefit (overall response rate (ORR) in around 16% of patients and median OS of 6-8 months). Further, SCLC is the tumor entity with the highest incidence of combined Rb1/p53 loss-of-function of up to 90% overall, and the expression of p300 and CBP is associated with poor prognosis.

A cancer that is to be treated can be staged according to the American Joint Committee on Cancer (AJCC) TNM classification system, where the tumor (T) has been assigned a stage of TX, T1, T1mic, T1a, Tib, Tic, T2, T3, T4, T4a, T4b, T4c, or T4d; and where the regional lymph nodes (N) have been assigned a stage of NX, NO, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pNO, PNO (I−), PNO (I+), PNO (mol−), PNO (mol+), PN1, PN1(mi), PNia, PNib, PNic, pN2, pN2a, pN2b, pN3, pN3a, pN3b, or pN3c.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. In some embodiments, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "monotherapy" refers to the administration of a single active or therapeutic compound to a subject in need thereof. In some embodiments, monotherapy will involve administration of a therapeutically effective amount of an active compound. For example, cancer monotherapy with one of the compound of the present invention, or a pharmaceutically acceptable salt, polymorph, solvate, analog or derivative thereof, to a subject in need of treatment of cancer. Monotherapy may be contrasted with combination therapy, in which a combination of multiple active compounds is administered, with each component of the combination present in a therapeutically effective amount. In one aspect, monotherapy with a compound of the present invention, or a pharmaceutically acceptable salt, polymorph or solvate thereof, is more effective than combination therapy in inducing a desired biological effect.

As used herein, "treating" or "treat" describes the management and care of a patient for the purpose of combating a disease, condition, or disorder and includes the administration of a compound of the present invention, or a pharmaceutically acceptable salt, polymorph or solvate thereof, to alleviate one or more symptoms or complications of a disease, condition or disorder, or to eliminate the disease, condition or disorder. The term "treat" can also include treatment of a cell in vitro or an animal model.

Compound 1, or a pharmaceutically acceptable salt, polymorph or solvate thereof, can also be used to prevent a disease, condition or disorder, or used to identify suitable candidates for such purposes. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In some embodiments, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. Signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

Treating cancer can result in a reduction in size of a tumor. A reduction in size of a tumor may also be referred to as "tumor regression". In some embodiments, after treatment, tumor size is reduced by 5% or greater relative to its size prior to treatment; tumor size is reduced by 10% or greater; reduced by 20% or greater; reduced by 30% or greater; reduced by 40% or greater; reduced by 50% or greater; or reduced by greater than 75% or greater. Size of a tumor may be measured by any reproducible means of measurement. The size of a tumor may be measured as a diameter of the tumor.

Treating cancer can result in a reduction in tumor volume. In some embodiments, after treatment, tumor volume is reduced by 5% or greater relative to its size prior to treatment; tumor volume is reduced by 10% or greater; reduced by 20% or greater; reduced by 30% or greater; reduced by 40% or greater; reduced by 50% or greater; or reduced by greater than 75% or greater. Tumor volume may be measured by any reproducible means of measurement.

Treating cancer results in a decrease in number of tumors. In some embodiments, after treatment, tumor number is reduced by 5% or greater relative to number prior to treatment; tumor number is reduced by 10% or greater; reduced by 20% or greater; reduced by 30% or greater; reduced by 40% or greater; reduced by 50% or greater; or reduced by greater than 75%. Number of tumors may be measured by any reproducible means of measurement. The number of tumors may be measured by counting tumors visible to the naked eye or at a specified magnification. In some embodiments, the specified magnification is 2×, 3×, 4×, 5×, 10×, or 50×.

Treating cancer can result in a decrease in number of metastatic lesions in other tissues or organs distant from the primary tumor site. In some embodiments, after treatment, the number of metastatic lesions is reduced by 5% or greater relative to number prior to treatment; the number of metastatic lesions is reduced by 10% or greater; reduced by 20% or greater; reduced by 30% or greater; reduced by 40% or greater; reduced by 50% or greater; or reduced by greater than 75%. The number of metastatic lesions may be measured by any reproducible means of measurement. The number of metastatic lesions may be measured by counting metastatic lesions visible to the naked eye or at a specified magnification. In some embodiments, the specified magnification is 2×, 3×, 4×, 5×, 10×, or 50×.

Treating cancer can result in an increase in average survival time of a population of treated subjects in comparison to a population receiving carrier alone. In some embodiments, the average survival time is increased by more than 30 days; by more than 60 days; by more than 90 days; or by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. In some embodiments, the average survival time is increased by more than 30 days; by more than 60 days; by more than 90 days; or by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, polymorph, solvate, analog or derivative thereof. In some embodiments, the average survival time is increased by more than 30 days; by more than 60 days; by more than 90 days; or by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, polymorph, solvate, analog or derivative thereof. In some embodiments, the mortality rate is decreased by more than 2%; by more than 5%; by more than 10%; or by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. In some embodiments, after treatment, tumor growth rate is reduced by at least 5% relative to number prior to treatment; tumor growth rate is reduced by at least 10%; reduced by at least 20%; reduced by at least 30%; reduced by at least 40%; reduced by at least 50%; reduced by at least 50%; or reduced by at least 75%. Tumor growth rate may be measured by any reproducible means of measurement. Tumor growth rate can be measured according to a change in tumor diameter per unit time.

Treating cancer can result in a decrease in tumor regrowth. In some embodiments, after treatment, tumor regrowth is less than 5%; tumor regrowth is less than 10%; less than 20%; less than 30%; less than 40%; less than 50%; less than 50%; or less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating cancer can result in a reduction in the rate of cellular proliferation. In some embodiments, after treatment, the rate of cellular proliferation is reduced by at least 5%; by at least 10%; by at least 20%; by at least 30%; by at least 40%; by at least 50%; by at least 50%; or by at least 75%. The rate of cellular proliferation may be measured by any reproducible means of measurement. The rate of cellular proliferation is measured, for example, by measuring the number of dividing cells in a tissue sample per unit time.

Treating cancer can result in a reduction in the proportion of proliferating cells. In some embodiments, after treatment, the proportion of proliferating cells is reduced by at least 5%; by at least 10%; by at least 20%; by at least 30%; by at least 40%; by at least 50%; by at least 50%; or by at least 75%. The proportion of proliferating cells may be measured by any reproducible means of measurement. In some embodiments, the proportion of proliferating cells is measured, for example, by quantifying the number of dividing cells relative to the number of non-dividing cells in a tissue sample. The proportion of proliferating cells can be equivalent to the mitotic index.

Treating cancer can result in a decrease in size of an area or zone of cellular proliferation. In some embodiments, after treatment, size of an area or zone of cellular proliferation is reduced by at least 5% relative to its size prior to treatment; reduced by at least 10%; reduced by at least 20%; reduced by at least 30%; reduced by at least 40%; reduced by at least 50%; reduced by at least 50%; or reduced by at least 75%. Size of an area or zone of cellular proliferation may be measured by any reproducible means of measurement. The size of an area or zone of cellular proliferation may be measured as a diameter or width of an area or zone of cellular proliferation.

Treating cancer can result in a decrease in the number or proportion of cells having an abnormal appearance or morphology. In some embodiments, after treatment, the number of cells having an abnormal morphology is reduced by at least 5% relative to its size prior to treatment; reduced by at least 10%; reduced by at least 20%; reduced by at least 30%; reduced by at least 40%; reduced by at least 50%; reduced by at least 50%; or reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

Treating cancer can result in cell death. In some embodiments, cell death results in a decrease of at least 10% in number of cells in a population. In some embodiments, cell death means a decrease of at least 20%; a decrease of at least 30%; a decrease of at least 40%; a decrease of at least 50%; a decrease of at least 75%; a decrease of at least 80%; a decrease of at least 85%; a decrease of at least 90%; a decrease of at least 95%; a decrease of at least 95%; a decrease of at least 99%; or complete cell death of the population of cancer cells. Number of cells in a population may be measured by any reproducible means. A number of cells in a population can be measured by fluorescence-activated cell sorting (FACS), immunofluorescence microscopy and light microscopy. Methods of measuring cell death are as shown in Li et al., Proc Natl Acad Sci USA. 100(5): 2674-8, 2003. In an aspect, cell death occurs by apoptosis.

Treating cancer can result in senescence of cancer cells. Senescent cells are cells that have undergone an irreversible growth arrest. Senescence is characterized by characterized by distinct morphology, gene expression pattern, and secretory phenotype.

As used herein, the term "selectively" means tending to occur at a higher frequency in one population than in another population. The compared populations can be cell populations. In some embodiments, a compound of the present invention, or a pharmaceutically acceptable salt, polymorph or solvate thereof, acts selectively on a cancer or precancerous cell but not on a normal cell. In some embodiments, a compound of the present invention, or a pharmaceutically acceptable salt, polymorph or solvate thereof, acts selectively to modulate one molecular target (e.g., p300) but does not significantly modulate another molecular target (e.g., a non-target protein). The invention also provides a method for selectively inhibiting the activity of a protein such as p300. In some embodiments, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; greater than fifty times; greater than 100 times; or greater than 1000 times more frequently in population A as compared to population B. For example, cell death would be said to occur selectively in cancer cells if it occurred greater than twice as frequently in cancer cells as compared to normal cells.

Contacting a cell with Compound 1 of the present invention, or a pharmaceutically acceptable salt, polymorph or solvate thereof, can induce or activate cell death selectively in cancer cells. Administering to a subject in need thereof Compound 1 of the present invention, or a pharmaceutically acceptable salt, polymorph or solvate thereof, can induce or activate cell death selectively in cancer cells. Contacting a cell with Compound 1 of the present invention, or a pharmaceutically acceptable salt, polymorph or solvate thereof, can induce cell death selectively in one or more cells affected by a cell proliferative disorder. In some embodiments, administering to a subject in need thereof Compound 1 of the present invention, or a pharmaceutically acceptable salt, polymorph or solvate thereof, induces cell death selectively in one or more cells affected by a cell proliferative disorder.

Biomarkers

In one aspect, the present disclosure provides methods of treating a cancer with Compound 1 of the disclosure. In some embodiments, the cancer is deficient in the expression or function of p53, Rb, or a combination thereof. In some embodiments, the cancer is deficient in the expression or function of p53, ASXL1 or a paralog thereof, or RUNX1 or a paralog thereof. Loss of expression of expression or function of p53, Rb or a combination thereof occurs not only through loss of expression or mutation of p53 and/or Rb, but also through loss of expression or mutation of one or genes in the p53 and/or Rb pathways.

Changes in p53 and/or Rb signaling are correlated with the susceptibility cancers to Compound 1.

Any genes involved in the p53 and/or Rb signaling pathways whose altered expression, activity or function is correlated with susceptibility of cancer cells to Compound 1 is envisaged as within the scope of the instant disclosure. Any genes involved in DNA damage repair (DDR), including genes in the p53 and/or Rb signaling pathways, are envisaged as within the scope of the instant disclosure.

Members of the p53 and Rb signaling pathways include, but are not limited to, upstream regulators of p53 and Rb, interaction partners of p53 and Rb, and downstream targets of p53 and Rb. Members of the p53 and Rb pathways, as well as additional DNA damage repair (DDR) genes. The p53 and Rb pathways are described in PCT/EP2021/050574, the contents of which are incorporated by reference herein in their entirety.

In canonical p53 signaling, activatory signals stabilize p53 protein through phosphorylation. Under normal homeostatic conditions, p53 is degraded following MDM2-mediated ubiquitination. Signals that activate p53, such as stress, oncogenic activation, or DNA damage, induce stabilization of the p53 protein through phosphorylation by protein kinases including ATM serine/threonine kinase (ATM), ATR serine/threonine kinase (ATR), checkpoint kinase 1 (Chk1), checkpoint kinase 2 (Chk2) and others. This phosphorylation also promotes binding of p53 to DNA (e.g., at p53 target promoters). The ARF product of the cyclin dependent kinase inhibitor 2A (CDKN2A) locus also regulates p53 by inhibiting MDM2 regulation of p53, stabilizing p53 as a result. DNA-bound p53 then recruits the transcriptional machinery to activate transcription of p53 target genes.

Genes upstream of P53 include, but are not limited to, genes involved in extracellular matrix interactions, hypoxia response, DNA damage response, response to microtubule disruption, regulators of cellular reduction-oxidation states, and regulators of cellular metabolism. Exemplary genes upstream of p53 include, but are not limited to MDM2 proto-oncogene (MDM2), and the p14ARF product of the CDKN2A locus.

Genes that interact with p53 include, but are not limited to, genes that regulate post-translational modification of p53, genes that inhibit p53 or regulate its interaction with inhibitors, and genes that function as co-factors for p53 or regulate the interaction of p53 with co-factors. Both direct and indirect interactions are within the scope of the instant disclosure. Exemplary genes involved in the post translational modification of p53, either directly or indirectly, include, but are not limited to, casein kinase 1 alpha 1 (CK1), casein kinase 2 alpha 1 (CK2), kinases such as ATM serine/threonine kinase (ATM), ATR serine/threonine kinase (ATR), Chk1 and Chk2, Pin1, dual specificity tyrosine phosphorylation regulated kinase 2 (DYRK2), homeodomain interacting protein kinase 2 (HIPK2), MDM2, dual specificity tyrosine phosphorylation regulated kinase 2 (Cop1), ARF, MSL complex subunit 2 (MSL2), lysine acetyltransferase 5 (TIP60), lysine acetyltransferase 8 (MOF) and CBP/p300. Exemplary p53 co-factors include, but are not limited to, ASPP1 and ASPP2, which facilitate binding of p53 to target promoters, and others such as Strap, JMY and p300.

p53 generally functions as a transcriptional activator. p53 transcriptional targets include, but are not limited to, genes involved in cell cycle regulation, apoptosis, senescence, genetic stability, cell adhesion, motility, invasion, epithelial to mesenchymal transition (EMT) and angiogenesis. Exemplary but non-limiting p53 target genes are described in Table 2, below. These include, but are not limited to, target genes involved in cell cycle regulation, such as cyclin dependent kinase 1 (CDK1), Cyclin A2, E2F transcription factor 7 (E2F7), BAG anti-proliferation factor 2 (BTG2), growth arrest and DNA damage inducible alpha (GADD45A), SFN (Stratifin), and cyclin dependent kinase inhibitor 1A (CDKN1A); translation control, such as sestrin 1 (SESN1) and SESN2 (sestrin 2); apoptosis, such as TNF receptor superfamily member 10 A-D (TNFRSF10A-D), TNF receptor associated factor 4 (TRAF4), p53 apoptosis effector related to PMP22 (PERP), BCL2 binding component 3 (BBC3), phorbol-12-myristate-13-acetate-induced protein 1 (PMAIP1), TP53 regulated inhibitor of apoptosis 1 (TRIAPI), sushi domain containing 6 (SUSD6), Fas cell surface death receptor (FAS), BCL2 associated X, apoptosis regulator (BAX), apoptotic peptidase activating factor 1 (APAF1) and apoptosis enhancing nuclease (AEN); metabolism, such as glutaminase 2 (GLS2), ferredoxin reductase (FDXR), alpha-L-fucosidase 1 (FUCA1), protein kinase AMP-activated non-catalytic subunit beta 1 (PRKAB1), TP53 induced glycolysis regulatory phosphatase (TIGAR) and pantothenate kinase 1 (PANK1); autophagy, such as protein kinase AMP-activated non-catalytic subunit beta 1 (PRKAB1) and DNA damage regulated autophagy modulator 1 (DRAMI1); and regulation of p53 through feedback mechanisms, such as MDM2, cyclin G1 (CCNG1) and protein phosphatase, Mg2+/Mn2+ dependent 1D (PPM1D). p53 also regulates the expression of matrix metalloproteinases (MMPs) such as MMP1 and MMP2, and the MMP1 receptor discoidin domain receptor tyrosine kinase 1 (DDR1), whose expression is correlated with cancer progression.

The Rb tumor suppressor gene, originally identified in a retinoblastoma, is functionally inactivated cancer cells with high frequency in a majority of human cancers. Mammalian Rb1 is a member of a family of three related proteins, RB transcriptional corepressor 1 (Rb1), RB transcriptional corepressor like 1 (p107) and RB transcriptional corepressor like 2 (p130). Phosphorylation plays a key role in regulating Rb family members. Rb1 contains numerous phosphorylation sites that are phosphorylated by cyclin D/CDK4/6, cyclin E/CDK2, and cyclin A/CDK2 complexes during cell cycle progression. Generally, hypophosphorylated Rb1 acts to inhibit cell proliferation and tumor suppression, while hyperphosphorylated Rb1 is less active, or inactive.

Rb proteins play an important role in regulating the G1 to S phase transition during the cell cycle. In early G1, Rb family members are hypophosphorylated and associate with E2F transcription factors to prevent the expression of cell cycle expression genes. As cells progress through G1, cyclin D and CDK4/6 promote the hyperphosphorylation of Rb family proteins. This results in dissociation of the Rb protein from E2F transcription factors, and allows progression through G1 and eventually S-phase entry. Rb1 recruits chromatin remodeling factors needed to regulate the expression of genes required for S-phase entry, including histone deacetylases, the SWI/SNF chromatin remodeling complex, and helicases involved in chromatin remodeling such as SWI/SNF related, matrix associated, actin dependent regulator of chromatin, subfamily a, member 4 (Brg1) and SWI/SNF related, matrix associated, actin dependent regulator of chromatin, subfamily a, member 2 (Brm). Rb1 may also regulate transcription via chromatin methylation, which inhibits transcription, and play a role in initiating DNA replication during S-phase.

Rb1 also regulates senescence in cells. Under stress conditions, the CDKN2A gene product p16INK is upregulated, leading to Rb1 upregulation. This leads to chromatin reorganization, repression of E2F family transcription factor target genes, and exit from the cell cycle into senescence. Without wishing to be bound by theory, it is thought that one way that Rb signaling may prevent proliferation of cancer cells is through the promotion of cellular senescence in cancer cells.

Rb signaling also likely plays a direct role in regulating cellular differentiation, by interacting not just with E2F family transcription factors, but other developmental transcription factors as well. Without wishing to be bound by theory, it is thought that another way Rb signaling may prevent cancer cell proliferation is by activating cellular differentiation pathways. This causes cancer cells to undergo terminal differentiation and stop proliferating. For example, mutation of Rb in mouse lungs led to more neuroendocrine cell differentiation, which suggested that Rb can regulate differentiation in lung cells by specifically inhibiting neuroendocrine cell fate (Wilkenheiser-Brokamp, K. A., Development, 2004, 131:4299).

Dysfunction of the p53 and/or Rb1 pathways in cancer cells are predictive of the anti-proliferative effects of Compound 1. Although p53 and Rb1 are not direct targets of Compound 1, Compound 1 is able to specifically drive apoptosis in cancer cells with lesions in p53 and Rb1. This is in contrast to previous studies carried out with CBP/p300 histone acetyltransferase (HAT) or bromodomain inhibitors, which pointed to the efficacy of CBP/p300 inhibitors in cells with lesions in either p300 or CBP, producing the so-called "synthetic lethality" effect (for a better understanding, see Ogiwara H. et al. Cancer Discov. 2016 April; 6(4):430-45).

Accordingly, the disclosure provides methods of treating a cancer with Compound 1, comprising: (a) determining the activity, function or expression of at least one p53 or Rb pathway gene in a cancer cell of the subject, where dysregulation or loss of function of p53 or Rb pathway signaling indicates that the cancer will respond to treatment with Compound 1 as described herein. In some embodiments, the method comprises administering Compound 1 to the subject.

The disclosure also provides methods of treating a subject with a cancer, comprising: (a) determining the activity or expression of at least one gene in a cancer cell of the subject, wherein the at least one gene in the p53 or Rb pathway; and administering Compound 1 to the subject when the activity or expression of the at least one gene in the cancer is different from the activity or expression of the at least one gene in non-cancerous control cells. In some embodiments, the at least one gene comprises ABL proto-oncogene 1 (c-ABL), protein phosphatase 1 regulatory subunit 13B (ASPP1), tumor protein p53 binding protein 2 (ASPP2), AKT serine/threonine kinase 1 (AKT1), APAF1, ATM, ATR, BCL2 antagonist/killer 1 (Bak1), BAX, BCL2 apoptosis regulator (Bcl2), BCL2 like 1 (Bcl2L1), BH3 interacting domain death agonist (BID), BRCA1 DNA repair associated (BRCA1), distal-less homeobox 4 (BP1), DDR1, DYRK2, cyclin dependent kinase 4 (CDK4), cyclin dependent kinase 6 (CDK6), cyclin dependent kinase inhibitor 1A (CDKN1A), CDKN2A, Fos proto-oncogene, AP-1 transcription factor subunit (FOS), CHK1, CHK2, COP1, casein kinase 1 (CSNK1), Cyclin D, Cyclin E, Cytochrome C (CYCS), E2F transcription factor 1 (E2F1), mitogen-activated protein kinase 1 (ERK2), GADD45A, glycogen synthase kinase 3 beta (GSK3B), H19 imprinted maternally expressed transcript (H19), histone deacetylase 1 (HDAC1), hypoxia inducible factor 1 subunit alpha (HIF1a), homeodomain interacting protein kinase 2 (HIPK2), mitogen-activated protein kinase 8 (INK), junction mediating and regulatory protein, p53 cofactor (JMY), long intergenic non-protein coding RNA, regulator of reprogramming (Linc-ROR), metastasis associated lung adenocarcinoma transcript 1 (MALAT-1), MDM2 proto-oncogene (MDM2), MDM4 regulator of p53 (MDMX), maternally expressed 3 (MEG3), MOF, MSL complex subunit 2 (MSL2), Nibrin (NBS1), PMAIP1, mitogen-activated protein kinase 14 (p38), p53, poly(ADP-ribose) polymerase 1 (PARP1), lysine acetyltransferase 2 (PCAF), protein inhibitor of activated STAT 1 (PIAS1), phosphatidylinositol glycan anchor biosynthesis class S (PIGS), promyelocytic leukemia (PML), phosphatase and tensin homolog (PTEN), BCL2 binding component (PUMA), sirtuin 1 (SIRT1), sirtuin 2 (SIRT2), serine/threonine kinase receptor associated protein (STRAP), TATA-box binding protein associated factor 1 (TAF1), TIP60, MOF or ubiquitin specific peptidase 7 (USP7). In some embodiments, the at least one gene comprises at least two genes, and the at least two genes comprise at least one gene selected from the group consisting of c-ABL, ASPP1, ASPP2, AKT1, APAF1, ATM, ATR, Bak1, BAX, Bcl2, Bcl2L1, BID, BRCA1, BP1, DDR1, DYRK2, CDK4, CDK6, CDKN1A (p21), FOS, CHK1, CHK2, NBS1, PARP1, COP1, CSNK1, Cyclin D, Cyclin E, CYCS, E2F1, ERK2, GADD45A, GSK3B, H19, HDAC1, HIF1a, HIPK2, INK, JMY, Linc-ROR, MALAT-1, MDM2, MDMX, MEG3, MOF, MSL2, NOXA, p38, p53, PCAF, PIAS1, PIGS, PML, PTEN, PUMA, SIRT1, SIRT2, STRAP, TAF1, TIP60, MOF and USP7; and CDKN2A.

In some embodiments of the methods of the disclosure, the at least one gene comprises forkhead box M1 (FOXM1), MYC proto-oncogene (c-Myc), APAF1, Ampk-alpha2, ASPP2, ATM, BCL2 like 11 (Bim), BRG1, BMI1 proto-oncogene, polycomb ring finger (Bmi-1), BRM, caspase 3 (CASP3), caspase 7 (CASP7), caspase 8 (CASP8), caspase 9 (CASP9), CDC6, CDK1, CDK2, CDK4, CDK6, CDKN1B, CDKN2A, CDKN2B, CDKN2C, CHK1, CHK2, NBS1, PARP1, Cyclin A, Cyclin D, Cyclin E, E2F1, E2F2, E2F3, E2F4, E2F5, E2F6, E2F7, E2F8, F-box protein 5 (Emi-1), HDAC1, helicase, lymphoid specific (HELLS), DNA polymerase alpha catalytic subunit (Pol alpha), Pbx homeobox 1 (Pbx1), p107, p130, tumor protein p73 (p73), RAS proto-oncogene, GTPase (Ras), Rb1, SIVA1 apoptosis inducing factor (Siva1) or Thymidine kinase (Tk). In some embodiments, the at least one gene comprises at least two genes, and the at least two genes comprise at least one gene selected from the group consisting of FOXM1, c-Myc, APAF1, Ampk-alpha2, ASPP2, ATM, Bim, BRG1, Bmi-1, BRM, CASP3, CASP7, CASP8, CASP9, cell division cycle 6 (CDC6), CDK1, CDK2, CDK4, CDK6, CDKN1B, CDKN2B, CDKN2C, CHK1, CHK2, NBS1, PARP1, Cyclin A, Cyclin D, Cyclin E, E2F1, E2F2, E2F3, E2F4, E2F5, E2F6, E2F7, E2F8, Emi-1, HDAC1, HELLS, Pol alpha, Pbx1, p107, p130, p73, Ras, Rb1, Siva1 and Tk; and CDKN2A.

In some embodiments, the at least one gene comprises one gene selected from the group consisting of c-ABL, ASPP1, ASPP2, AKT1, APAF1, ATM, ATR, Bak1, BAX, Bcl2, Bcl2L1, BID, BRCA1, BP1, DDR1, DYRK2, CDK4, CDK6, CDKN1A (p21), CDKN2A, FOS, CHK1, CHK2, NBS1, PARP1, COP1, CSNK1, Cyclin D, Cyclin E, CYCS, E2F1, ERK2, GADD45A, GSK3B, H19, HDAC1, HIF1a, HIPK2, INK, JMY, Linc-ROR, MALAT-1, MDM2, MDMX, MEG3, MOF, MSL2, NOXA, p38, p53, PCAF, PIAS1, PIGS, PML, PTEN, PUMA, SIRT1, SIRT2, STRAP, TAF1, TIP60, MOF and USP7; and one gene selected from the group consisting of FOXM1, c-Myc, APAF1, Ampk-alpha2, ASPP2, ATM, Bim, BRG1, Bmi-1, BRM, CASP3, CASP7, CASP8, CASP9, CDC6, CDK1, CDK2, CDK4, CDK6, CDKN1B, CDKN2A, CDKN2B, CDKN2C, CHK1, CHK2, NBS1, PARP1, Cyclin A, Cyclin D, Cyclin E, E2F1, E2F2, E2F3, E2F4, E2F5, E2F6, E2F7, E2F8, Emi-1, HDAC1, HELLS, Pol alpha, Pbx1, p107, p130, p73, Ras, Rb1, Siva1 and Tk. In some embodiments, the at least one gene comprises, or further comprises, CDKN2A.

In some embodiments, the at least one gene comprises Rb1, CDKN2B, CDKN2C, BRG1, BRM, Cyclin D1, CDK4, CDK6, E2F1, FOXM1, c-Myc, or HDAC1.

In some embodiments, the difference in the activity or expression of the at least one gene comprises a loss of expression or function of Rb1, CDKN2A, CDKN2B, CDKN2C, BRG1 or BRM, or an increase of expression or function of Cyclin D1, E2F1, or HDAC1.

In some embodiments, the at least one gene comprises p53, CDKN1A, ATM, ATR, CHK1, CHK2, NBS1, PARP1, c-Abl or MDM2. In some embodiments, the difference in the activity or expression of the at least one gene comprises a loss of expression or function of p53, CDKN1A, ATM, ATR, CHK1, CHK2, NBS1, PARP1, or c-Abl, or an increase in expression or function of MDM2.

In some embodiments, the at least one gene comprises CDKN2A. The CDKN2A gene, or locus, encodes several proteins, including P16INK4A (also called p16, INK4, INK4A and p16INK4A) and p14ARF (also called p14 and ARF). P16INK4A binds to CDK4/6, while p14ARF prevents p53 degradation. CDKN2A transcripts include, but are not limited to the non-coding RNAs CDKN2B antisense RNA 1 (CKN2B-AS1), and the proteins p14ARF, P16INK4A, isoform p12, isoform p16 and any additional isoforms thereof All transcript variants and proteins products of CDKN2A are envisaged as within the scope of the disclosure.

In some embodiments, the at least one gene comprises Rb1. In some embodiments, the change in function, activity or expression of the at least one gene comprises a change in function, activity or expression of Rb1. In some embodiments, the change in function, activity or expression of Rb1 comprises a mutation in the Rb1 gene.

In some embodiments, the at least one gene comprises p53. The p53 locus encodes multiple isoforms of p53, all of which are considered as within the scope of the instant disclosure. In some embodiments, the change in function, activity or expression of the at least one gene comprises a change in function, activity or expression of p53. In some embodiments, the change in function, activity or expression of p53 comprises a mutation in the p53 gene.

In some embodiments, the at least one gene comprises CDKN1A (also called p21). The CDKN1A locus encodes multiple isoforms of CDKN1A, all of which are considered as within the scope of the instant disclosure. In some embodiments, the change in function, activity or expression of the at least one gene comprises a change in function, activity or expression of CDKN1A. In some embodiments, the change in function, activity or expression of CDKN1A comprises a mutation in the CDKN1A gene.

In some embodiments, the at least one gene comprises (a) Rb1, CDKN2B, CDKN2C, BRG1, BRM, Cyclin D1, CDK4, CDK6, E2F1 or HDAC1; and (b) p53, CDKN1A, ATM, ATR, CHK1, CHK2, NBS1, PARP1, c-Abl or MDM2. In some embodiments, the at least one gene further comprises CDKN2A. In some embodiments, the at least one gene comprises p53, Rb1 and CDKN2A. In some embodiments, the at least one gene comprises p53 or CDKN1A, Rb1 and CDKN2A.

In some embodiments, the at least one gene comprises (a) Rb1, CDKN2B, CDKN2C, BRG1, BRM, Cyclin D1, CDK4, CDK6, E2F1 or HDAC1, 53, CDKN1A, ATM, ATR, CHK1, CHK2, NBS1, PARP1, c-Abl or MDM2; and CDKN2A.

In some embodiments, the difference in the activity or expression of the at least one gene comprises: (a) a loss of expression or function of Rb1, CDKN2A, CDKN2B, CDKN2C, BRG1 or BRM, or an increase of expression or function of Cyclin D1, E2F1 or HDAC1; and (b) a loss of expression or function of p53, CDKN1A, ATM, ATR, CHK1, CHK2, NBS1, PARP1, or c-Abl, or an increase in expression or function of MDM2.

In some embodiments, the at least one gene comprises one of: (a) p53 and CDKN2A; (b) CDKN1A and CDKN2A; (c) Rb1 and CDKN2A; (d) p53 and Rb1; (e) CDKN1A and Rb1; (f) CDKN1A, Rb1 and CDKN2A; or (g) p53, Rb1 and CDKN2A. In some embodiments, the difference in the activity or expression of the at least one gene comprises a loss in activity or expression of any one or more of p53, CDKN1A, Rb1 or CDK2NA.

In some embodiments, at least one gene comprises p53 and Rb1, and the difference in activity or expression of the at least one gene comprises a loss of expression or function of Rb1 and p53.

The disclosure provides methods of determining the susceptibility of a cancer, for example a hematological cancer, to Compound 1 comprising assaying the activity, expression or function of p53 signaling pathway gene in a cancer cell and a non-cancerous control cell, optionally assaying the activity, expression or function of ASXL transcriptional regulator 1 (ASXL1) or a paralog thereof, or RUNX1 or a paralog thereof, in a cancer cell and a non-cancerous control cell, and comparing the activity, expression or function of a p53 signaling pathway gene and ASXL1 or a paralog thereof, or RUNX1 or a paralog thereof, between the cancer cell and the control cell. In some embodiments, the methods comprise assaying the activity, expression of function of p53, and both ASXL1 or a paralog thereof, and RUNX1 or a paralog thereof In some embodiments, the methods comprise assaying the activity, expression of function of p53, ASXL1 and RUNX1. In other aspects, the methods comprise assaying the activity of p53, and ASXL1 or a paralog thereof In still further aspects, the methods comprise assaying the activity of p53 and RUNX1 or a paralog thereof Changes in p53, ASXL1 and RUNX1 are correlated with the susceptibility hematological cancers to CBP/p300 modulators. In some embodiments, for example those embodiments where the hematological cancer cell comprises dysfunction p53 and/or ASXL1 or RUNX1, a therapeutically effective amount of Compound 1 is administered to the subject.

ASXL transcriptional regulator 1 (ASXL1) is a chromatin binding protein and member of the Polycomb group of proteins, which are necessary for maintaining stable repression of certain genes. There are multiple alternative splice variants, and all transcripts and isoforms are envisaged as within the scope of the instant disclosure. ASXL1 paralogs include, but are not limited to, ASXL transcriptional regulator 2 (ASXL2) and ASXL transcriptional regulator 3 (ASXL3).

RUNX family transcription factor 1 (RUNX1) is a heterodimeric transcription factor that can make up part of the core transcriptional machinery. RUNX1 can be transcribed from two alternative promoters, and also undergo alternative splicing. All RUNX1 isoforms and transcripts are envisaged as within the scope of the instant disclosure. RUNX1 paralogs, include, but are not limited to, RUNX family transcription factor 2 (RUNX2), and RUNX family transcription factor 3 (RUNX3).

Mutations that alter the function of any of the genes described herein can be substitutions, insertions, deletions or inversions in the gene sequences. Mutations can be in protein coding sequences, or in non-coding sequences such as promoters, introns or cis-regulatory elements. Mutations in protein coding sequences include non-synonymous mutations, i.e. causes a change in the amino acid sequence, mis-sense mutations, frameshift mutations or mutations that cause premature stops in the amino acid sequence. Alternatively, expression of the genes described herein can be altered in the absence of the gene sequence itself. For example, epigenetic modification of a locus can result in reduced gene expression, or mutation of a transcriptional regulator of a gene can result in loss of expression of the gene.

Any differences in the activity, expression or function of genes in the p53 and/or Rb pathways, or ASXL1, RUNX1 or paralogs thereof, between cancer cells and non-cancerous control cells are envisaged as within the scope of the instant disclosure.

Differences in activity, expression or function of genes in the Rb and/or p53 pathways, as well as RUNX1, ASXL1 or paralogs thereof, between cancer and control cells include, but are not limited to increases and decreases in the levels of protein or RNA products encoded by genes, changes in levels of non-coding RNAs encoded by genes, changes protein modification status, and mutations in the genes in the pathways.

As used herein, "protein modification" refers to addition of a peptidic or non-peptidic moiety to a protein that cannot be considered as the elongation of the peptidic chain of the protein. The addition of the peptidic or non-peptidic moiety can be in vivo or in vitro. The peptidic or non-peptidic moiety can be added to a pure protein or a protein or peptidic component of a complex containing such protein or peptide. Protein modification frequently occur post-translationally. Exemplary post-translational protein modification include phosphorylation, acetylation, methylation, ADP-ribosylation, SUMOylation, ubiquitination, addition of a polypeptide side chain, addition of a hydrophobic group, and addition of a carbohydrate. Phosphorylation can include phosphorylation of a tyrosine, serine, threonine or histidine.

Protein modifications can contribute to the activity of the protein. Among various post-translational modifications, protein phosphorylation is a common mechanism for switching a protein from its active state to an inactive state. For example, phosphorylation of Rb1 modulates its interaction with E2F family transcription factors. As a further example, acetylation of p53 is associated with a change of its transcriptional activity after DNA damage.

Changes in expression, activity and function of p53 and/or Rb pathway genes, as well as RUNX1, ASXL1 or paralogs thereof, can include changes in the expression of the RNA product encoded by the gene or genes. RNAs include protein coding RNAs (messenger RNAs, or mRNAs) and non-coding RNAs such as long non-coding RNAs (lncRNAs). Changes in expression can be quantitative, i.e., a decrease or increase in the level of the RNA in a cancer cell relative to a control cell, or qualitative, i.e. the expression of an RNA in a cell type that does not normally express the RNA in the control cells, or the loss of expression of an RNA in a cell that normally expresses the RNA (i.e., in the control cells).

Changes in RNA or protein expression level can be caused by many mechanisms, all of which are envisaged as within the scope of the instant disclosure. For example, increased copy number (expansion) of genes can cause increased expression, while decreases in copy number can cause decreases in expression. Changes in epigenetic modification of DNA, e.g. in histone methylation, ubiquitination, phosphorylation, or acetylation, or mutational changes in non-coding sequences, such as regulatory elements, can also cause changes in gene expression, as can mutations in regulatory regions of genes. Loss of expression can be full, or can be partial. For example, a loss of expression in cancer cells can be a loss of at least 5%, 10%, 15%, 20%, 25%, 30%, 35%, 40%, 45%, 50%, 55%, 60%, 65%, 70%, 75%, 80%, 85%, 90%, 95% of the expression when compared to expression in non-cancerous control cells. Loss of expression can also be complete loss of expression (100%).

Expression, activity and function of p53 and/or Rb pathway genes, as well as RUNX1, ASXL1 or paralogs thereof, can be modified by mutation of the genes themselves. The mutation, or mutations, can be an insertion, a deletion, a point mutation, an inversion or a combination thereof Mutations in p53 and/or Rb pathway genes can occur in protein coding sequences (i.e., exons), or in non-coding sequences such as cis-regulatory sequences, introns, promoters, or intergenic regions. Mutations in coding sequences include missense, frameshift mutations, nonsense mutations and mutations that introduce premature stop codons resulting in truncated protein products. Depending on the mutation, mutations can be loss of function, or gain of function, mutations. Loss of function can be partial, i.e. a partial reduction in function, or complete (a null mutation). A loss of function in cancer cells can be a loss of at least 5%, 10%, 15%, 20%, 25%, 30%, 35%, 40%, 45%, 50%, 55%, 60%, 65%, 70%, 75%, 80%, 85%, 90%, 95% of the function when compared to expression in non-cancerous control cells. Loss of function can also be complete loss of function (100%).

Cancer cells can be heterozygous for mutations in p53 and/or Rb pathway genes, as well as RUNX1, ASXL1 or paralogs thereof, homozygous, or hemizygous. Mutations in these genes can be present in some, or all, of the cells of the cancer. For example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 99% of the cancer cells may carry a mutation in a p53 or Rb pathway gene as described herein.

Mutations in p53, and databases of mutations in p53, are described in Leroy et al. 2014, Human Mutation 35(6): 672-688, the contents of which are incorporated by reference herein. In exemplary embodiments, mutations include missense, nonsense and frameshift mutations in exons 5-8 of p53, which are frequently identified in cancers.

In some embodiments, determining the activity or expression of at least one gene comprises measuring a level of mRNA expression of the at least one gene, measuring protein expression of the at least one gene, determining a genomic or mRNA sequence of the at least one gene, measuring a post-translational modification in the protein product of the at least one gene, or measuring a change in epigenetic modification of the at least one gene.

All methods of measuring gene expression, function and activity known in the art can be employed with the methods of the instant disclosure.

The practice of the present disclosure employs, unless otherwise indicated, conventional techniques of biochemistry, chemistry, molecular biology, microbiology, cell biology, genomics and recombinant DNA, which can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Methods of characterizing gene expression, function and activity are described, for example, in US200301503014A1 and US20110212104A1, the contents of each of which are incorporated by reference in their entireties herein.

Levels of p53 and/or Rb pathway proteins, DDR proteins, or ASXL1, RUNX1 or paralogs thereof, can be quantified by any method known in the art, including but not limited to, mass spectrometry, Western blot, IBC or ELISA. Means for determining the levels of the proteins of the present disclosure include, but are not limited to, the methods disclosed herein, and their equivalents.

In some embodiments, p53 and/or Rb pathway protein levels, levels of DDR proteins, or levels of ASXL1, RUNX1 or paralogs thereof, are determined by Western blot (immunoblot). In other embodiments, protein levels are determined by enzyme-linked immunosorbent assay (ELISA).

Antibodies specific to post-translationally modified forms of proteins, for example antibodies specific to K382 acetylated p53, can be used to detect post-translational modifications. Alternatively, or in addition, methods that determine protein size such as the gel electrophoresis and mass spectrometry methods described herein can be used to characterize protein post-translational modifications. Lateral flow format immunoassays (immunochromatographic assay) may also be used. Any other suitable assay format may be used to detect the p53 and/or Rb pathway proteins, DDR proteins, RUNX1, ASXL1 or paralogs thereof, of the instant disclosure, such as radioimmunoassays, nephelometry/turbidimetry, specifically immunoturbidimetry, which involves measurement of light scattering caused by suspended insoluble antigen (p53 or Rb protein)/antibody complexes. See, e.g. U.S. Pat. No. 4,605,305. Other methods include radial immunodiffusion (RID), which is observation of a precipitin ring generated by complex formation between an antigen (p53 or Rb protein) and an antibody, e.g. in an agar/agarose slab. See, e.g. U.S. Pat. No. 3,947,250.

In other embodiments, the p53 or Rb pathway proteins, DDR proteins, RUNX1, ASXL1 or paralogs thereof, may be detected by mass spectrometric methods. Mass spectrometric methods include time-of-flight, magnetic sector, quadrupole filter, ion trap, ion cyclotron resonance, electrostatic sector analyzer and hybrids of these. In such embodiments, the p53 or Rb pathway protein in the sample can be identified and quantified using isotope labeled identical synthetic peptides spiked into the sample. In another mass spectrometric embodiment, the sample is optionally chromatographically fractionated, and p53 or Rb pathway protein is then captured on a bio-affinity resin, e.g. a resin derivatized with an antibody. The protein is then eluted from the resin and analyzed by MALDI, electrospray, or another ionization method for mass spectrometry. In yet another embodiment, the sample is fractionated on an anion exchange resin and detected directly by MALDI or electrospray mass spectrometry.

In other embodiments, the level of gene expression of p53 and/or Rb pathway genes, DDR genes, RUNX1, ASXL1 or paralogs thereof, may be determined at the RNA level. Gene expression at the nucleic acid level can be quantitated by any method known in the art, including but not limited to, Northern blot analysis, gene chip expression analysis, or RT-PCR (real-time polymerase chain reaction) and high throughput sequencing of either mRNA (RNA-Seq).

In some embodiments, the levels of gene expression of p53 and/or Rb pathway genes, DDR genes, RUNX1, ASXL1 or paralogs thereof, is quantified by Northern blot analysis. Northern blot analysis is a standard method for detection and quantitation of mRNA. RNA is isolated from a sample to be assayed (e.g., a cancer biopsy). RNA is separated by size by electrophoresis in an agarose gel under denaturing conditions, transferred to a membrane, crosslinked, and hybridized with a labeled probe.

In some embodiments, expression of p53 and or Rb pathway genes, DDR genes, RUNX1, ASXL1 or paralogs thereof, is determined using a gene chip (probe array). A biological sample of interest is prepared and hybridized to the chip, which is subsequently washed, stained and scanned.

In some embodiments, expression of p53 and or Rb pathway genes, DDR genes, RUNX1, ASXL1 or paralogs thereof, is determined using high throughput sequencing. In some embodiments, RNA from cancer cells from a subject, and optionally control cells is reverse transcribed to make cDNA, which is used to make high throughput sequencing libraries using methods known in the art, e.g. through amplification and the addition of barcodes, sequencing adapters and the like. The libraries are then sequenced using any suitable sequencing platform, for example via Illumina or IonTorrent.

In some embodiments, gene expression is determined using real time PCR (RT-PCR). Design of the primers and probes required for RT-PCR of the p53 and/or Rb pathway genes, DDR genes, RUNX1, ASXL1 or paralogs thereof, of the present disclosure is within the skill in the art.

In some embodiments, genomic DNA from cancer cells from a subject, and optionally control cells, is isolated using methods known in the art and sequenced using high throughput sequencing. High throughput sequencing can be used to determine changes in gene copy number through the quantification of reads, or to identify mutations in genes such as p53 and/or Rb pathway genes, or RUNX1, ASXL1 or paralogs thereof High throughput sequencing of genomic DNA can be used to identify mutations in genes such as p53 and/or Rb pathway genes and quantify the frequency of such mutations in cancer cells in a subject.

P53 or Rb pathway genes, DDR genes, RUNX1, ASXL1 or paralogs thereof, or expression thereof may be detected using commercially available kits and reagents (e.g. as disclosed in the examples), or using custom assays with commercially available antibodies obtained from suppliers well known in the art, or using custom assays and antibodies raised by the investigator. Antibodies to p53 pathway genes will be known to persons of ordinary skill in the art and are commercially available. See, for example www.abcam.com/primary-antibodies/p53-antibody-marker-panel for a panel of p53 antibodies including antibodies to phosphorylated and acetylated forms of p53. Antibodies to Rb pathway genes will likewise be known to persons of ordinary skill in the art.

Combination Therapies

Compound 1 of the disclosure can be administered in therapeutically effective amounts in a combinational therapy with one or more therapeutic agents (pharmaceutical combinations) or modalities, e.g., an anti-proliferative, anti-cancer, immunomodulatory or anti-inflammatory agent. Where Compound 1 is administered in conjunction with other therapies, dosages of the co-administered compounds will of course vary depending on the type of co-drug employed, on the specific drug employed, on the condition being treated and so forth. Compound 1 can be administered in therapeutically effective amounts in a combinational therapy with one or more therapeutic agents (pharmaceutical combinations) or modalities, e.g., anti-proliferative, anti-cancer, immunomodulatory or anti-inflammatory agent, and/or non-drug therapies, etc. For example, synergistic effects can occur with anti-proliferative, anti-cancer, immunomodulatory or anti-inflammatory substances. Where Compound 1 is administered in conjunction with other therapies, dosages of the co-administered compounds will of course vary depending on the type of co-drug employed, on the specific drug employed, on the condition being treated and so forth.

Combination therapy includes the administration of the subject compounds in further combination with one or more other biologically active ingredients. For instance, the Compound 1 can be used in combination with other pharmaceutically active compounds, (e.g., compounds that are able to enhance the effect of the compounds of the application). Compound 1 can be administered simultaneously (as a single preparation or separate preparation), in temporal proximity, or sequentially to the other drug therapy or treatment modality. In general, a combination therapy envisions administration of two or more drugs during a single cycle or course of therapy.

In other aspects, Compound 1 may be administered in combination with one or more separate pharmaceutical agents, e.g., a chemotherapeutic agent, an immunotherapeutic agent, or an adjunctive therapeutic agent.

EMBODIMENTS

In further embodiments, enumerated as embodiments 1-78 below, the present disclosure includes:

Embodiment 1. A method of treating cancer comprising administering to a subject in need thereof Compound 1:

(Compound 1)

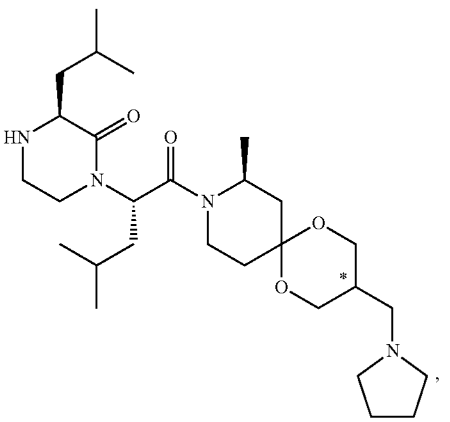

or a pharmaceutically acceptable salt, hydrate, solvate, or stereoisomer thereof, at a dosage from about 0.01 mg/kg to about 60 mg/kg.

Embodiment 2. The method of embodiment 1, wherein Compound 1 is a methanesulfonic acid salt (mesylate).

Embodiment 3. The method of embodiment 1, wherein Compound 1 is Compound 1':

(Compound 1')

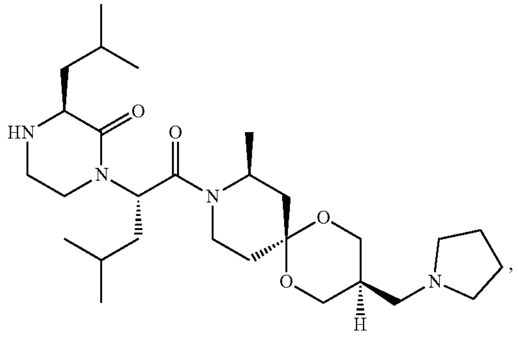

or a pharmaceutically acceptable salt, hydrate, solvate, or stereoisomer thereof.

Embodiment 4. The method of embodiment 1, wherein Compound 1' is a methanesulfonic acid salt (mesylate).

Embodiment 5. The method of any one of embodiments 1-4, wherein Compound 1 is administered at a dosage from about 0.4 mg/kg to about 15 mg/kg.

Embodiment 6. The method of any one of embodiments 1-4, wherein Compound 1 is administered at a dosage from about 0.8 mg/kg to about 6 mg/kg.

Embodiment 7. The method of any one of embodiments 1-4, wherein Compound 1 is administered at a dosage of about 1.2 mg/kg.

Embodiment 8. The method of any one of embodiments 1-4, wherein Compound 1 is administered at a dosage of about 2.4 mg/kg.

Embodiment 9. The method of any one of embodiments 1-4, wherein Compound 1 is administered at a dosage of about 4.8 mg/kg.

Embodiment 10. The method of any one of embodiments 1-9, wherein Compound 1 is administered once every seven days.

Embodiment 11. The method of any one of embodiments 1-10, wherein Compound 1 is administered once every seven days for one week.

Embodiment 12. The method of any one of embodiments 1-10, wherein Compound 1 is administered once every seven days for two weeks.

Embodiment 13. The method of any one of embodiments 1-10, wherein Compound 1 is administered once every seven days for three weeks.

Embodiment 14. The method of any one of embodiments 1-10, wherein Compound 1 is administered once every seven days for four weeks.

Embodiment 15. The method of any one of embodiments 1-10, wherein Compound 1 is administered once every seven days for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

Embodiment 16. The method of any one of embodiments 1-10, wherein Compound 1 is administered once every seven days followed by a dosing holiday.

Embodiment 17. The method of any one of embodiments 1-10, wherein Compound 1 is administered once every seven days followed by a one week dosing holiday, a two week dosing holiday, a three week dosing holiday, a four week dosing holiday, a six week dosing holiday, an eight week dosing holiday, a 10 week dosing holiday, a 12 week dosing holiday, a 14 week dosing holiday, a 16 week dosing holiday, an 18 week dosing holiday, a 20 week dosing holiday, a 22 week dosing holiday, a 24 week dosing holiday, a 28 week dosing holiday, a 32 week dosing holiday, a 36 week dosing holiday, a 40 week dosing holiday, a 44 week dosing holiday, a 48 week dosing holiday, or a 52 week dosing holiday.

Embodiment 18. The method of embodiment 16 or 17, wherein the dosing holiday is followed by resuming administration of Compound 1 once every seven days.

Embodiment 19. The method of any one of embodiments 1-4, wherein Compound 1 is administered at a dosage from about 0.08 mg/kg to about 1.2 mg/kg.

Embodiment 20. The method of any one of embodiments 1-4, wherein Compound 1 is administered at a dosage from about 0.1 mg/kg to about 0.3 mg/kg.

Embodiment 21. The method of any one of embodiments 1-4, wherein Compound 1 is administered at a dosage of about 0.12 mg/kg.

Embodiment 22. The method of any one of embodiments 1-4, wherein Compound 1 is administered at a dosage of about 0.24 mg/kg.

Embodiment 23. The method of any one of embodiments 19-22, wherein Compound 1 is administered once daily for seven days.

Embodiment 24. The method of any one of embodiments 19-22, wherein Compound 1 is administered once daily for two weeks.

Embodiment 25. The method of any one of embodiments 19-22, wherein Compound 1 is administered once daily for three weeks.

Embodiment 26. The method of any one of embodiments 19-22, wherein Compound 1 is administered once daily for four weeks.

Embodiment 27. The method of any one of embodiments 19-22, wherein Compound 1 is administered once daily for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

Embodiment 28. The method of any one of embodiments 19-22, wherein Compound 1 is administered once daily followed by a dosing holiday.

Embodiment 29. The method of any one of embodiments 19-22, wherein Compound 1 is administered once daily for seven days followed by a seven day dosing holiday.

Embodiment 30. The method of any one of embodiments 19-22, wherein Compound 1 is administered once daily followed by a one week dosing holiday, a two week dosing holiday, a three week dosing holiday, a four week dosing holiday, a six week dosing holiday, an eight week dosing holiday, a 10 week dosing holiday, a 12 week dosing holiday, a 14 week dosing holiday, a 16 week dosing holiday, an 18 week dosing holiday, a 20 week dosing holiday, a 22 week dosing holiday, a 24 week dosing holiday, a 28 week dosing holiday, a 32 week dosing holiday, a 36 week dosing holiday, a 40 week dosing holiday, a 44 week dosing holiday, a 48 week dosing holiday, or a 52 week dosing holiday.

Embodiment 31. The method of any one of embodiments 28-30, wherein the dosing holiday is followed by resuming administration of Compound 1 once daily.

Embodiment 32. The method of any one of embodiments 1-4, wherein Compound 1 is administered at a dosage from about 0.01 mg/kg to about 0.8 mg/kg.

Embodiment 33. The method of any one of embodiments 1-4, wherein Compound 1 is administered at a dosage from about 0.03 mg/kg to about 0.55 mg/kg.

Embodiment 34. The method of any one of embodiments 1-4, wherein Compound 1 is administered at a dosage of about 0.08 mg/kg.

Embodiment 35. The method of any one of embodiments 1-4, wherein Compound 1 is administered at a dosage of about 0.24 mg/kg.

Embodiment 36. The method of any one of embodiments 1-4, wherein Compound 1 is administered at a dosage of about 0.48 mg/kg.

Embodiment 37. The method of any one of embodiments 32-36, wherein Compound 1 is administered once daily.

Embodiment 38. The method of embodiment 37, wherein Compound 1 is administered once daily for seven days.

Embodiment 39. The method of embodiment 37, wherein Compound 1 is administered once daily for two weeks.

Embodiment 40. The method of embodiment 37, wherein Compound 1 is administered once daily for three weeks.

Embodiment 41. The method of embodiment 37, wherein Compound 1 is administered once daily for four weeks.

Embodiment 42. The method of embodiment 37, wherein Compound 1 is administered once daily for six weeks, eight weeks, 10 weeks, 12 weeks, 14 weeks, 16 weeks, 18 weeks, 20 weeks, 22 weeks, 24 weeks, 28 weeks, 32 weeks, 36 weeks, 40 weeks, 44 weeks, 48 weeks, or 52 weeks.

Embodiment 43. The method of any one of embodiments 1-42, wherein Compound 1 is administered followed by a dosing holiday.

Embodiment 44. The method of any one of embodiments 1-42, wherein Compound 1 is administered followed by a one week dosing holiday, a two week dosing holiday, a three week dosing holiday, a four week dosing holiday, a six week dosing holiday, an eight week dosing holiday, a 10 week dosing holiday, a 12 week dosing holiday, a 14 week dosing holiday, a 16 week dosing holiday, an 18 week dosing holiday, a 20 week dosing holiday, a 22 week dosing holiday, a 24 week dosing holiday, a 28 week dosing holiday, a 32 week dosing holiday, a 36 week dosing holiday, a 40 week dosing holiday, a 44 week dosing holiday, a 48 week dosing holiday, or a 52 week dosing holiday.

Embodiment 45. The method of embodiment 43 or 44, wherein the dosing holiday is followed by resuming administration of Compound 1.

Embodiment 46. The method of any one of embodiments 1-4, wherein Compound 1 is administered once every seven days at a dosage of about 1.2 mg/kg.

Embodiment 47. The method of any one of embodiments 1-4, wherein Compound 1 is administered once every seven days at a dosage of about 2.4 mg/kg.

Embodiment 48. The method of any one of embodiments 1-4, wherein Compound 1 is administered once every seven days at a dosage of about 4.8 mg/kg.

Embodiment 49. The method of any one of embodiments 1-4, wherein Compound 1 is administered for seven consecutive days followed by a seven day dosing holiday at a dosage of about 0.12 mg/kg.

Embodiment 50. The method of any one of embodiments 1-4, wherein Compound 1 is administered for seven consecutive days followed by a seven day dosing holiday at a dosage of about 0.24 mg/kg.

Embodiment 51. The method of embodiment 49 or 50, wherein the dosing holiday is followed by resuming administration Compound 1.

Embodiment 52. The method of any one of embodiments 1-4, wherein Compound 1 is administered once daily at a dosage of about 0.08 mg/kg.

Embodiment 53. The method of any one of embodiments 1-4, wherein Compound 1 is administered once daily at a dosage of about 0.24 mg/kg.

Embodiment 54. The method of any one of embodiments 1-4, wherein Compound 1 is administered once daily at a dosage of about 0.48 mg/kg.

Embodiment 55. A composition comprising Compound 1, or a pharmaceutically acceptable salt thereof, for use in treating cancer in a subject in need thereof at a dosage from about 0.01 mg/kg to about 60 mg/kg.

Embodiment 56. Compound 1, or a pharmaceutically acceptable salt thereof, for use in treating cancer in a subject in need thereof at a dosage from about 0.01 mg/kg to about 60 mg/kg.

Embodiment 57. Use of a composition comprising Compound 1, or a pharmaceutically acceptable salt thereof, for the treatment of cancer in a subject in need thereof at a dosage from about 0.01 mg/kg to about 60 mg/kg.

Embodiment 58. Use of Compound 1, or a pharmaceutically acceptable salt thereof, for the treatment of cancer in a subject in need thereof at a dosage from about 0.01 mg/kg to about 60 mg/kg.

Embodiment 59. Use of a composition comprising Compound 1, or a pharmaceutically acceptable salt thereof, for the manufacture of a medicament for the treatment of cancer in a subject in need thereof at a dosage from about 0.01 mg/kg to about 60 mg/kg.

Embodiment 60. Use of Compound 1, or a pharmaceutically acceptable salt thereof, for the manufacture of a medicament for the treatment of cancer in a subject in need thereof at a dosage from about 0.01 mg/kg to about 60 mg/kg.

Embodiment 61. The method, compound, composition, or use of any one of embodiments 1-60, wherein the subject is a human.

Embodiment 62. The method, compound, composition, or use of any one of embodiments 1-61, wherein the cancer comprises a liquid tumor or a solid tumor.

Embodiment 63. The method, compound, composition, or use of any one of embodiments 1-62, wherein cells of the cancer express p300 and/or CBP.

Embodiment 64. The method, compound, composition, or use of any one of embodiments 1-63, wherein cells of the cancer have lost expression or function of p53, Rb, or a combination thereof.

Embodiment 65. The method, compound, composition, or use of any one of embodiments 1-64, wherein the cancer is Stage II, Stage III, or Stage IV cancer.

Embodiment 66. The method, compound, composition, or use of any one of embodiments 1-64, wherein the cancer comprises metastatic cancer.

Embodiment 67. The method, compound, composition, or use of any one of embodiments 1-66, wherein the cancer comprises prostate cancer, renal cancer, pancreatic cancer, liver cancer, breast cancer, gastric cancer, colon cancer, cervical cancer, ovarian cancer, head-and-neck cancer, esophageal cancer, hematological cancer, brain cancer, stomach cancer, cancer of the central nervous system, or skin cancer.

Embodiment 68. The method, compound, composition, or use of embodiment 67, wherein the cancer comprises lung cancer, gastric cancer, prostate cancer, breast cancer, hematological cancer, or colon cancer.

Embodiment 69. The method, compound, composition, or use of embodiment 67 or 68, wherein the hematological cancer comprises wherein the hematological cancer is acute lymphocytic leukemia (ALL), acute myeloid leukemia (AML), B cell lymphoma (BCL), chronic lymphocytic leukemia (CLL), chronic myeloid leukemia (CML), diffuse large B cell lymphoma (DLBCL), Epstein Barr driven hematological cancer, multiple myeloma (MM), T cell lymphoma (TCL), Hodgkin's lymphoma, or non-Hodgkin's lymphoma.

Embodiment 70. The method, compound, composition, or use of any one of embodiments 67-69, wherein the prostate cancer comprises castrate resistant prostate cancer (CRPC).

Embodiment 71. The method, compound, composition, or use of any one of embodiments 67-70, wherein the prostate cancer is neuroendocrine prostate cancer (NEPC).

Embodiment 72. The method, compound, composition, or use of any one of embodiments 67-71, wherein the prostate cancer is resistant to Androgen receptor (AR) pathway inhibitors.

Embodiment 73. The method, compound, composition, or use of embodiment 72, wherein the AR pathway inhibitors comprise abiraterone acetate, enzalutamide, apalutamide, darolutamide, or bicalutamide.

Embodiment 74. The method, compound, composition, or use of any one of embodiments 67-73, wherein the prostate cancer is androgen driven, AR positive adenocarcinoma.

Embodiment 75. The method, compound, composition, or use of any one of embodiments 1-74, wherein the cancer has relapsed after treatment with a first and/or second line therapy.

Embodiment 76. The method, compound, composition, or use of any one of embodiments 1-74, wherein the cancer has been unresponsive, or only partially responsive, to a first and/or second line therapy.

Embodiment 77. The method, compound, composition, or use of any one of embodiments 1-76, wherein administering the compound slows or stops tumor progression.

Embodiment 78. The method, compound, composition, or use of embodiment 77, wherein slowing or stopping tumor progression comprises inducing senescence of tumor cells.

Embodiment 79. The method, compound, composition, or use of embodiment 77 or 78, wherein administering the compound reduces tumor size.

Embodiment 80. The method, compound, composition, or use of any one of embodiments 76-79, wherein reducing tumor size comprises inducing apoptosis of tumor cells.

Embodiment 81. The method, compound, composition, or use of any one of the embodiments 1-80, wherein Compound 1, or the pharmaceutically acceptable salt, hydrate, solvate, or stereoisomer thereof, is administered by oral administration.

Embodiment 82. A compound having the structure of Compound 1':

(Compound 1')

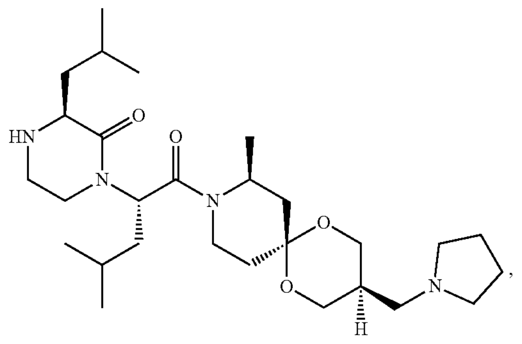

or a pharmaceutically acceptable salt, hydrate, solvate, or stereoisomer thereof.

Embodiment 83. The compound of embodiment 82, wherein Compound 1' is a methanesulfonic acid salt (mesylate).

EXAMPLES

Example 1: In vitro anti-proliferative effect of Compound 1 in cancer cell lines The activity of Compound 1 was tested in a panel of more than 500 cell lines, representing 23 different tumor types.

FIG. 1 shows that Compound 1 exhibited broad anti-proliferative efficacy in a large cell line panel of different tumor types, particularly including cell lines derived from prostate cancer (PC). The amount of cells remaining at the end of the treatment was estimated by CellTiter-Glo (Promega).

While Compound 1 triggered cytostatic effects in many cell lines, a maximum inhibition of >90% in a subset of cell lines indicated that these were affected in an apoptotic fashion, and low inhibitory values were correlated with such cytotoxic effects. Interestingly, many cell lines in this subset featured a combined deficiency in the Rb1 and p53 pathways.

Figure 2:
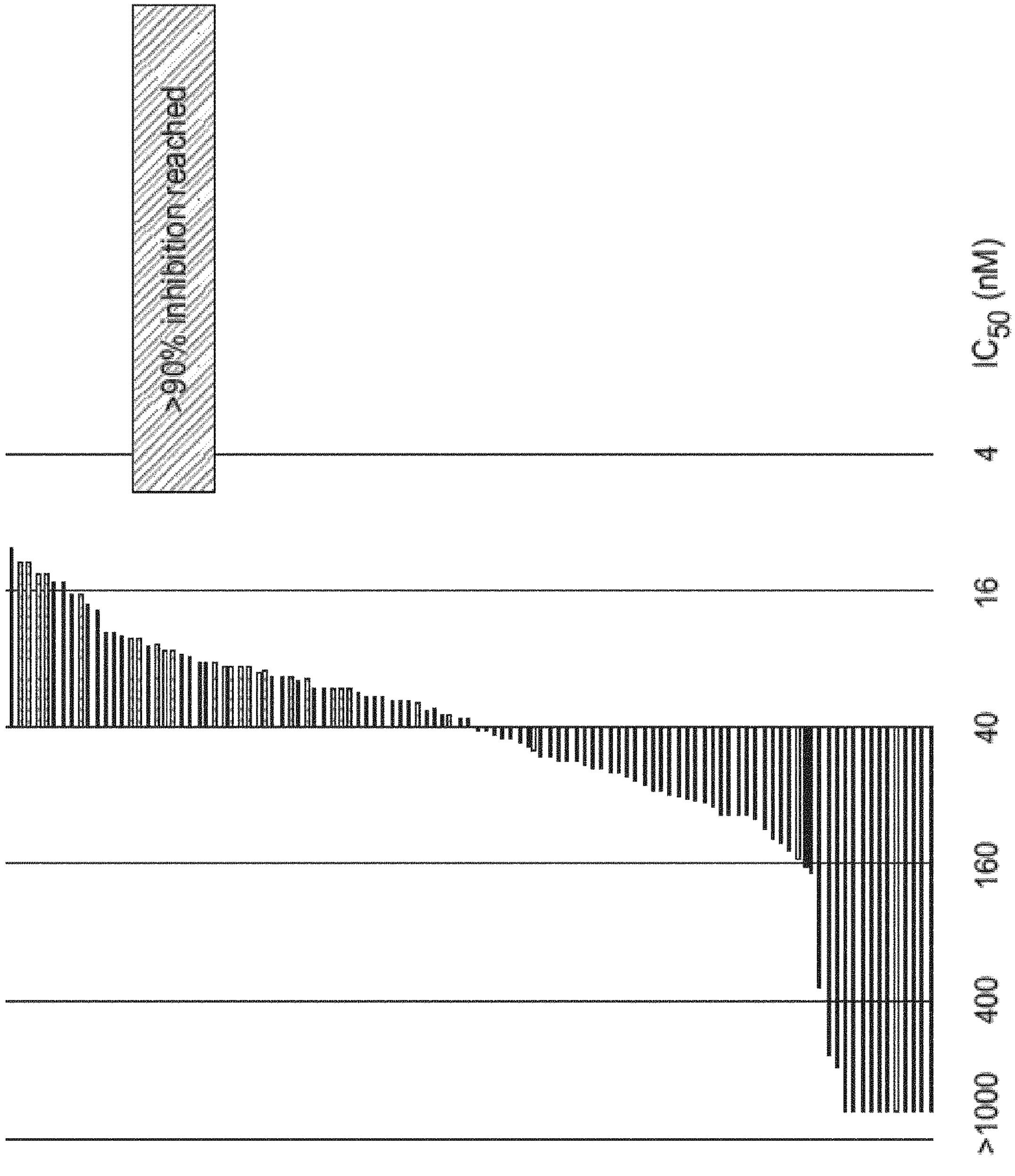
FIG. 2 shows half maximal inhibition concentration ($IC_{50}$) values for Compound 1 induced growth inhibition after 5 days on a set of 110 cancer cell lines. Note the increasing frequency of such a putative apoptotic reaction in cell lines responding to lower concentrations of Compound 1. Cell lines assayed, from top to bottom, are: MM.1S, JJN-3, RKO, PC-9, DU 145, A-204, JEG-3, A2058, HuP-T4, HCC1954, A-673, SNU-5, SW1990, KU812, NCI-H2286, NUGC-4, MONO-MAC-6, MM.1R, NCI-H1792, FaDu, KMS-11, MOLP8, NCI-H2122, CAL-27, LP-1, SNU-16, NCI-H1993, OVCAR-4, BxPC-3, NCI-H460, 22Rv1, KARPAS-299, SJCRH30, HT-1376, A2780, HuT 78, MOLM-13, A-375, JAR, A-875, SU-DHL-6, LCLC-97TM1, OVCAR-5, SW982, JIMT-1, NCI-H3122, ES-2, SCC-4, NCI-H358, NCI-H1944, OVCAR-8, HT-1080, A549, RPMI 8226, SK-BR-3, SK-LU-1, CFPAC-1, EJM, THP-1, NCI-H2052, OAW28, GRANTA-519, NCI-H2170, NCI-H322, NCI-H2452, NCI-H69, BT-549, SiHa, MIA PaCa-2, SNU-668, MCF7, NCI-H446, Caov-3, NCI-H2087, HEL 92.1.7, SU-DHL-8, NCI-H187, SK-MEL-5, SK-MES-1, Daudi, K-562, NCI-H2110, Ca Ski, NCI-H596, C666-1, U-2932, SW756, SW626, TF-1, AMO-1, NCI-H820, Capan-2, NCI-H82, CoC1, NCI-H526, 769-P, NCI-H1838, SW684, NCI-H209, OVCAR-3, NCI-H441, ZR-75-1, NCI-H727, NCI-H1915, NCI-H661, COV644, NCI-H226, TT, SJSA-1, LOU-NH91.

It was noted that cancer cell lines that were growth inhibited at lower concentrations of Compound 1 more frequently responded to Compound 1 exposure with an apoptotic reaction (FIG. 2). Since PC cell lines were among the cancer cell types displaying a particularly high sensitivity to Compound 1 treatment (FIG. 1), the potentially underlying biological reasons for an apoptotic response were investigated in a set of PC cell lines consisting of DU-145, LNCaP, 22Rv1 and PC3 cells. The DU-145 cell line showed an apoptotic response (verified by Caspase 3/7 cleavage, Table 1) upon Compound 1 exposure, whereas the other three cell lines did not. An analysis of potential correlations of these different responses to Compound 1 treatment and the genetic makeup of these cells revealed a putative relationship to the functional status of the tumor suppressor genes Rb1 and p53 (Table 1).

Based on the above findings, Compound 1 was tested in further cell lines with different Rb1/p53 (also referred to as Rb/p53) functional status. As mentioned before, the analysis of the first panel of 4 PC cell lines yielded one apoptotic (DU-145) and three senescent (i.e., growth arrested) responders (LNCaP, 22Rv1, PC3) as depicted in Table 1. Thus, the combined loss/mutation of Rb and p53 was identified as one putative predictor for apoptosis upon Compound 1 treatment as being present in DU-145 cells but not in LNCaP, 22Rv1 and PC3 cells. The examination of eight additional cell lines with a combined deficiency of Rb and p53 (derived from prostate, small cell lung and triple negative breast cancer plus one hematological tumor) confirmed that Compound 1 was able to induce apoptosis in all of these cell lines (Table 1). A retinoblastoma cell line (Y-79) served as an additional step of verification that Rb loss alone was not sufficient for induction of a resulting "synthetic lethality" (Table 1).

The results revealed that a combined deficiency (such as functional mutations, loss-of-function, deletions or no expression) in Rb1 and p53 and the corresponding loss of the G1/S checkpoint represent strong predictors of an apoptotic response (caspase 3/7 activation) to Compound 1 (Table 1) in a set of different cancer cell lines derived from different tumor types, including prostate cancer and small cell lung cancer.

The observed accumulation of DNA damage upon tumor cell exposure to Compound 1, measured as an increase of the DNA damage biomarker γH2A.X (FIG. 3A), is in line with reports of p300/CBP being involved in DNA replication and DNA damage repair (DDR). Of note, the CH1-domain targeted by Compound 1 is contained within the N-terminal approximately 600 amino acids of p300, which was shown to associate with proteins of the DDR machinery. Among these DDR proteins are ATR (ataxia telangiectasia and Rad3-related), which controls crucial cell cycle and repair checkpoints, but also nibrin (NBS1), and poly(ADP-ribose) polymerase 1 (PARP-1).

Figure 3A:
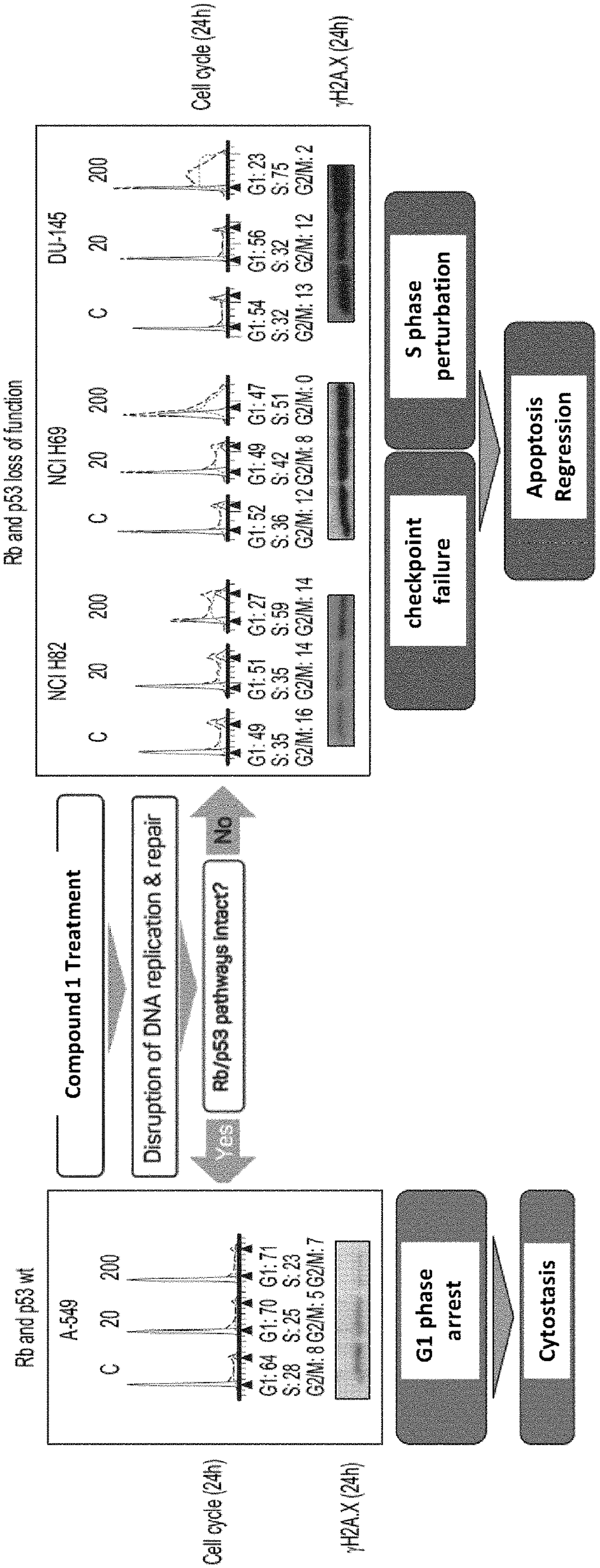
FIG. 3A shows responses to Compound 1 treatment depending on the presence of Rb/p53 pathway defects in prostate (DU-145) and lung cancer (SCLC: NCI-H82, NCI-H69/NSCLC: A549) cells. Cell cycle phase distribution in control (C) cells or cells treated at 20 or 200 nM Compound 1 for 24 hours (24 h) determined by fluorescence activated cell sorting (FACS) analysis, and detection of histone H2A variant H2A.X phosphorylation (γH2A.X, also referred to herein as gamma H2A.X or γH2A.X) by Western blot as DNA damage biomarker.
Figure 3B:
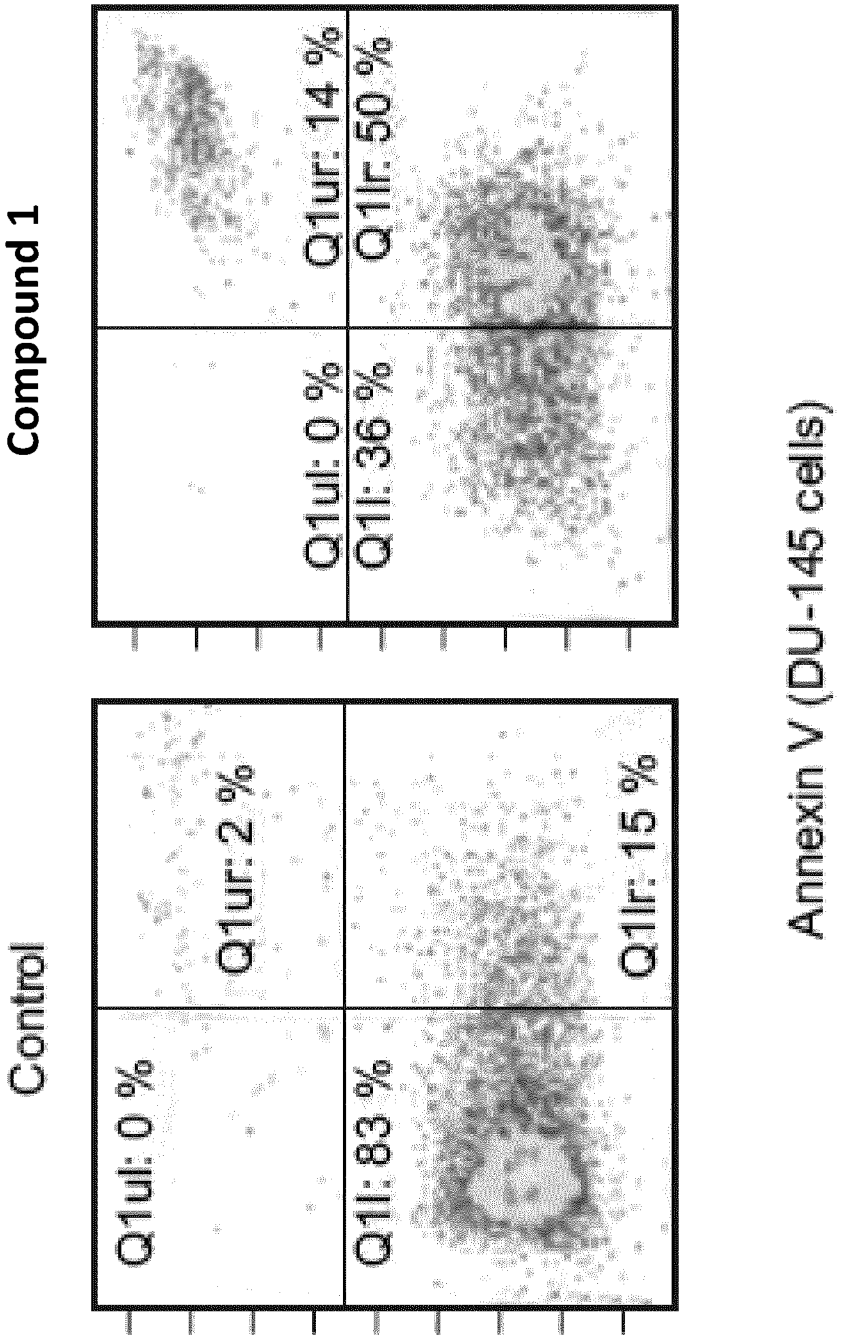
FIG. 3B shows Annexin V staining (lower right) showing the increase of the apoptotic cell fraction.

In FIG. 3A, protein amounts were normalized using total protein load with ImageLab 6.0 Software (BioRad). In prostate cancer cell line DU-145, and in SCLC cells NCI-H82 and NCI-H69 (right panel) deficient for Rb and p53, cell cycle FACS analysis reveals an accumulation of tumor cells in S-phase and accumulation of the DNA damage marker γH2A.X, indicating the presence of increased DNA damage. Annexin V staining in FIG. 3B suggests the induction of apoptosis (here exemplified in DU-145 cells), while A549 NSCLC cells (FIG. 3A, left panel) with a wild-type genotype of Rb and p53 were arrested in G1-phase of the cell cycle.

TABLE 1

Stratification for combined Rb/p53 loss-of-function enriches for apoptotic responders to Compound 1 treatment

| Type | Cell Line | Rb | p53 | Caspase 3/7, 8 | S-Phase Arrest |
|---|---|---|---|---|---|
| Prostate | DU-145 | x | x | + | + |
| | LNCaP | wt | wt | − | − |
| | 22Rv1 | wt | wt | − | − |
| | PC3 | wt | x | − | +/− |
| | NCI-H660 | x | x | + | + |
| SCLC | NCI-H69 | x | x | + | + |
| | NCI-H82 | x | x | + | + |
| | NCI-H146 | x | x | + | + |
| | NCI-H209 | x | x | + | + |
| | SCLC-21H | x | x | + | + |
| T-Cell | Hut-78 | x | x | + | + |
| Breast | BT-549 | x | x | + | + |
| Eye | Y-79 | x | wt | − | − |

In table 1, "wt"=wild-type; "x"=cells harboring Rb and p53 deficiencies; "+" (present) or "−" (absent) indicate the arrest (i.e. accumulation) of cells in S-phase triggered by Compound 1, which coincided with accumulation of the DNA damage marker phosphorylated gamma H2AX (γH2AX; see FIG. 3A). These events are followed by activation of caspases 3 and 7 as indicators of cell apoptosis as indicated by "+" (present) or "−" (absent). In cancer cells with intact Rb and/or p53 functions (wt=wild-type), Compound 1 induced growth arrest but not a substantial increase of cells in S-phase (=S-phase arrest). Upon release of treatment, such cells are able to proliferate again.

Figure 4:
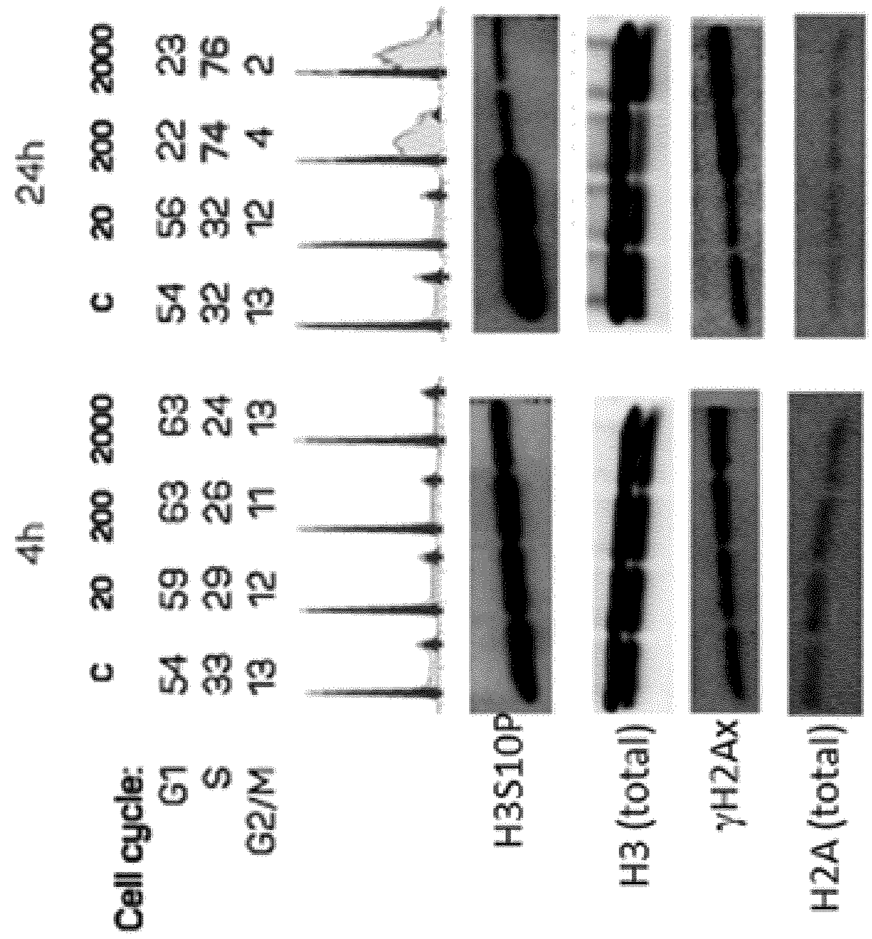
FIG. 4 shows the results of the experimental assessment of cell cycle and DNA damage biomarkers. Cell cycle distribution and Western blot analysis in DU-145 prostate cancer cells are shown. Top: Cell cycle phase distribution upon exposure to Compound 1 at 20, 200 and 2000 nM (C: untreated control) at 4 h and 24 h after treatment start. Middle: Western blot analysis of samples corresponding to treatment conditions given in the top panel, mitotic cell marker histone H3 (total) and amount of H3 phosphorylated on Serine 10 (H3S10P). Bottom: DNA damage marker phosphorylated γH2AX and H2A (total) protein.

Compound 1, by binding to its CH1 target domain, may interfere with the association of such DDR proteins to p300. This is expected to cause comparable consequences as shown experimentally by ATR inhibition, which resulted in deregulating the S/G2 transition, under-replicated DNA and increased DNA damage. This S/G2 checkpoint may, e.g., potentially be deregulated through Compound 1 interfering with a proper p300/ATR interaction. In other words, Compound 1 may induce lethality in tumor cells which harbor a combined Rb/p53 loss-of-function and therefore also a corresponding lack of a functional G1/S checkpoint, by additionally interfering with further downstream cell cycle checkpoints and DDR proteins at the level of S-phase or S/G2 transition. This would cause an accumulation of DNA damage and accumulation of cells in S-phase with subsequent death of tumor cells due to mitotic catastrophe. FIG. 4 shows the results of the experimental assessment of cell cycle and DNA damage biomarkers, particularly the cell cycle distribution and Western blot analysis for Compound 1 in DU-145 prostate cancer cells. The cell cycle phase distribution upon exposure to Compound 1 at 20, 200, and 2000 nM (C: untreated control) at 4 h and 24 h after treatment start (FIG. 4, top). The Western blot analysis of samples corresponding to treatment conditions given in the top panel, mitotic cell marker histone H3 (total) and amount of H3 phosphorylated on Serine 10 (H3S10P) (FIG. 4). DNA damage marker phosphorylated γH2AX and H2A (total) protein are shown at the bottom (FIG. 4).

In in vitro studies using LNCaP PC cells, harboring wild-type Rb and p53 genes, the effect of Compound 1 on the cell cycle was investigated in the absence and presence of siRNA-mediated knock-down of Rb and p53 gene expression. In comparison to control LNCaP cells not treated with siRNA (FIG. 5, control), in LNCaP cells treated with such siRNA, Compound 1 induced an increase of cells in the S-phase of the cell cycle, resembling the response to Compound 1 observed in DU-145 cells which harbor a combined loss-of-function of Rb and p53. This effect is hypothesized to be due to Compound 1-mediated perturbation of the interaction between p300 and DDR factors and subsequent impact on the late cell cycle checkpoints and the DDR leading to cell death.

Figure 5:
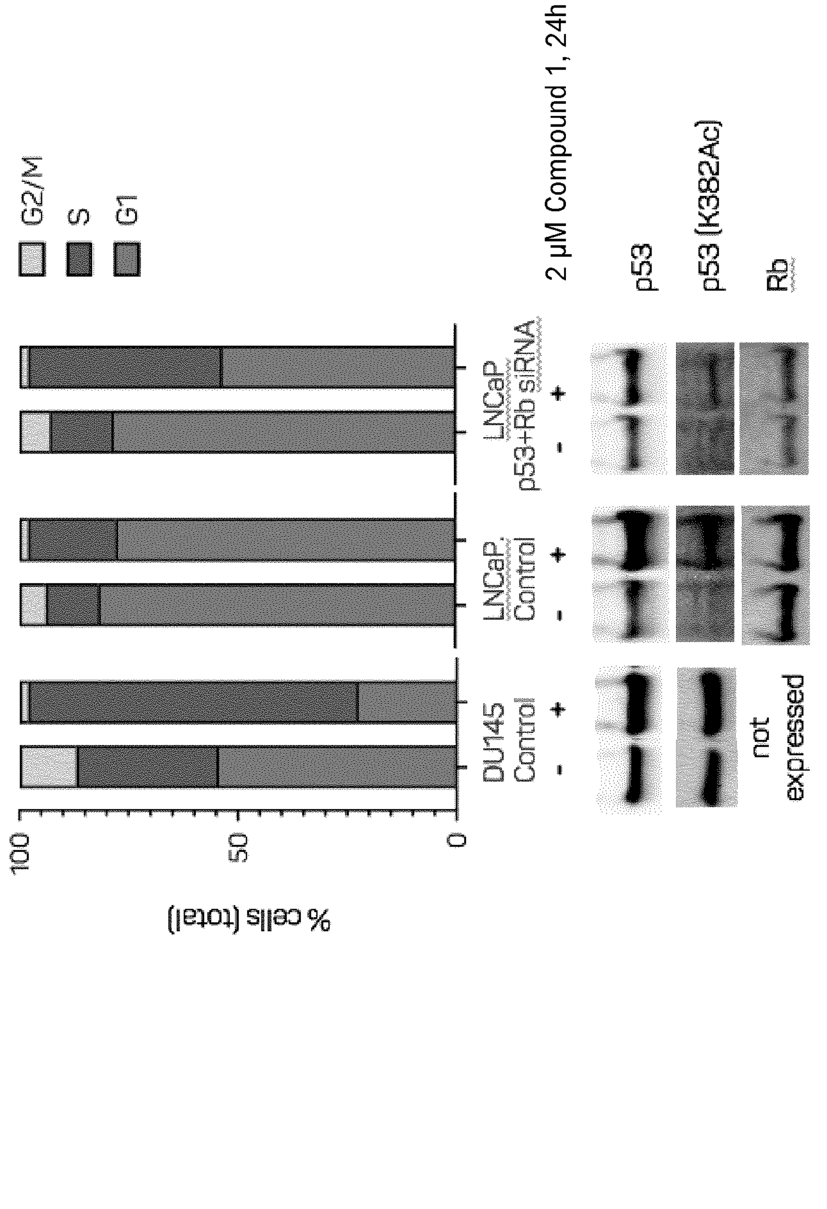
FIG. 5 shows siRNA-mediated Rb/p53 knock-down in LNCaP cells and accumulation of tumor cells in S-phase. Top panel: Cell cycle distribution in LNCap cells treated with siRNA (2 bars on the right) in comparison to control LNCaP cells without siRNA treatment (2 bars in the middle), in the absence (−) or presence (+) of Compound 1 for 24 h at the indicated concentration. For comparison, DU-145 cells harboring a combined Rb1 and p53 loss-of-function are included (2 bars on the left). Lower panel: Western blot analysis according to the same experimental conditions as given for the top panel.

As shown in FIG. 5, the siRNA-mediated knock-down of Rb and p53 in LNCaP cells was only partial, as assessed by western blotting of total Rb and p53 proteins. The amount of p53 specifically acetylated by p300 on amino acid K382 was increased by Compound 1 in control LNCaP cells and subsequently reduced when p53 expression was knocked down by siRNA. The Compound 1 induced p300-specific p53 acetylation on K382 indicates that the HAT/KAT activity of p300 is not inhibited by Compound 1.

Several castration-resistant prostate cancer (CRPC) cell lines, i.e., DU145, PC3, 22Rv1, LNCaP and NCI-H660 (Table 1), representative of different late-stage CRPC with variable Androgen receptor (AR) and Rb/p53 states, indicate that Compound 1 has a broad and strong anti-proliferative effect on all of these prostate cell line types. Specifically, the cell line NCI-H660, derived from a small cell neuroendocrine PC type, responded strongly to Compound 1. This could be verified when employing NCI-H660 cells in an in vivo CDX mouse tumor model (FIG. 10B).

Figure 6A:
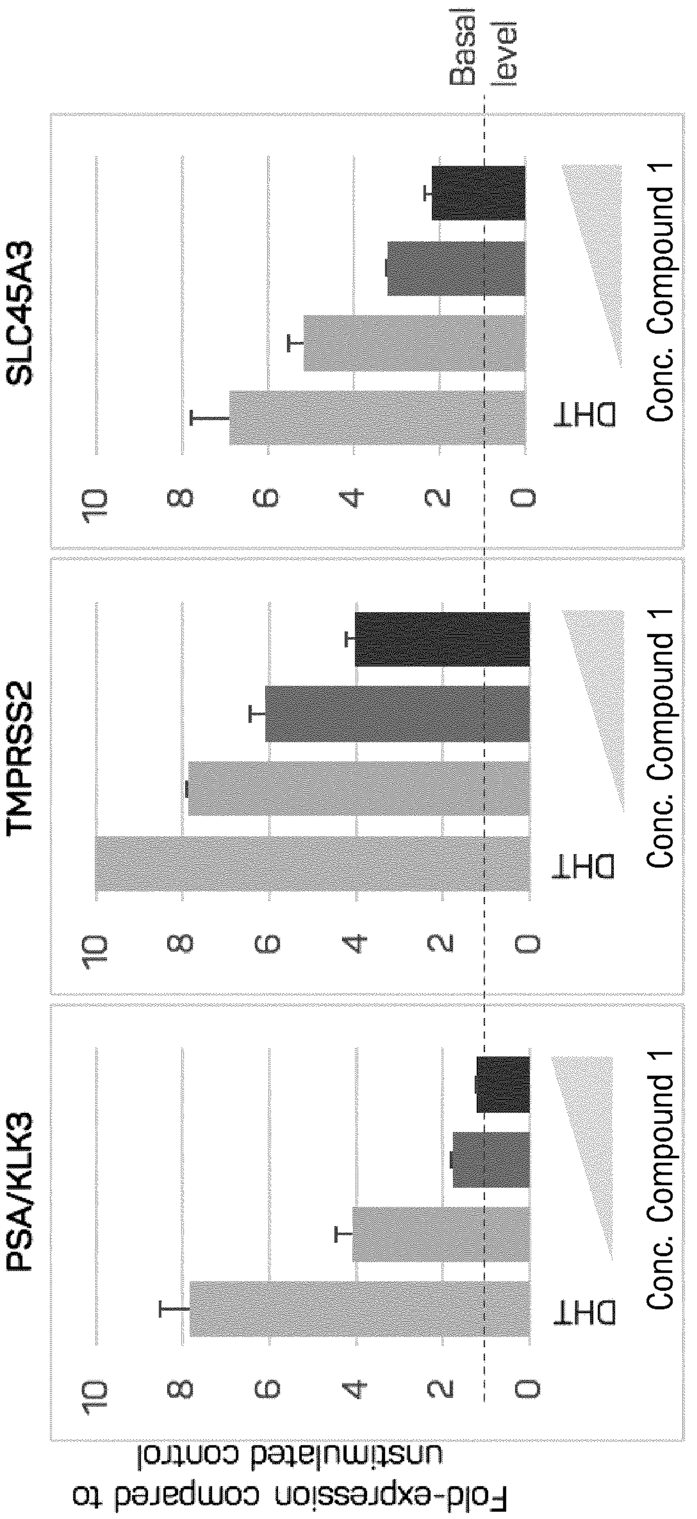
FIG. 6A shows LNCaP prostate cancer cells stimulated with dihydrotestosterone (DHT) and Compound 1-mediated attenuation of expression of PSA (KLK3) and other AR-downstream genes such as TMPRSS2 (transmembrane protease serine subtype 2, middle panel) and SCL45A3 (left panel). Compound 1 concentrations from left to right: 30, 300, 3000 nM. Basal level indicates expression level in cells with no DHT treatment.
Figure 6B:
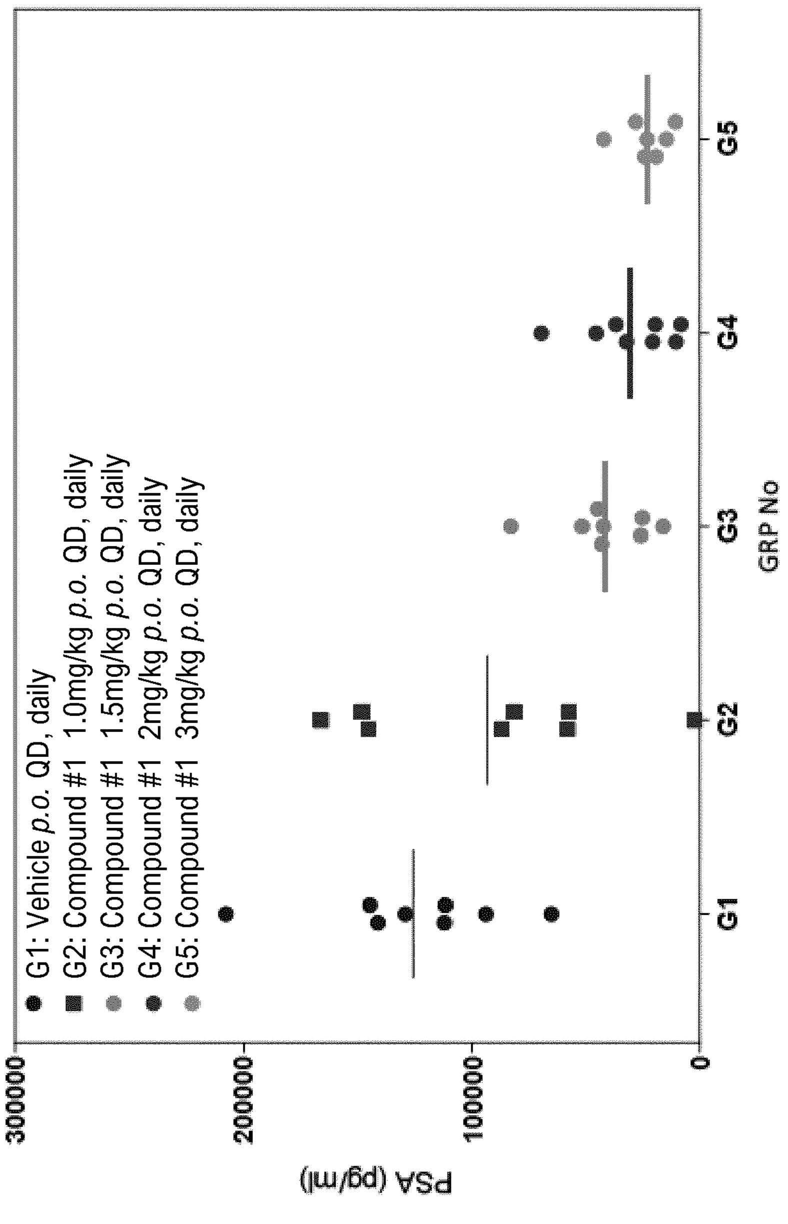
FIG. 6B shows prostate-specific antigen (PSA) in blood of the PR6512 mouse PDX prostate cancer in vivo model (see FIG. 7B for PR6512 efficacy data). Similar data of effective PSA reduction were obtained in the PR6511 prostate cancer derived PDX model.

Furthermore, Compound 1, when tested for its inhibitory activity on AR-driven gene expression, revealed that Compound 1 effectively downregulates target genes (i.e., PSA (KLK3), TMPRSS2, and SLC45A3) of the AR upon induction with dihydrotestosterone (DHT) (FIGS. 6A-6B). In SCLC, the expression of p300 and CBP is associated with poor prognosis (see Gao et al, Int J Clin Exp Pathol. 2014 Jan. 15; 7(2):760-7) with high p300 and CBP expressions being independent prognostic markers of poor overall survival (OS) for resected SCLC patients. Moreover, SCLC displays a combined loss-of-function of Rb1 and p53 at a very high frequency (see George et al., Nature. 2015 Aug. 6; 524(7563):47-53; Sonkin et al., Lung Cancer Manag. 2019 Aug. 21; 8(2):LMT13) which is expected to render this tumor type particularly sensitive to treatment with Compound 1. In line with this, a set of SCLC cancer cell lines harboring combined mutations of Rb1 and p53 responded with induction of apoptosis to Compound 1 treatment (Table 1).

Compound 1 demonstrated potent in vitro growth inhibition of a large number of cancer cell lines representing many different tumor types. While Compound 1 triggered cytostatic effects in many of the tested cell lines, in a subset of cell lines Compound 1 caused growth inhibition of more than 90% which furthermore correlated with low growth inhibitory $IC_{50}$ values, suggesting that these cell lines were affected in an apoptotic fashion. Many of the cell lines in this subset had deficiencies in the Rb1 and p53 tumor suppressor pathways. PC cells were among the most sensitive solid tumor types with IC50 values in the nanomolar range.

Compound 1 appeared to cause "synthetic lethality" in tumor cells lacking the G1/S checkpoint due to a combined Rb/p53 loss-of-function. Compound 1 treatment of tumor cells that harbor combined functional deficiencies in the Rb and p53 pathways caused "synthetic lethality" through an accumulation of DNA damage in tumor cells with subsequent cell death.

Example 2: Anti-Tumoral Effects of Compound 1 in Mouse Tumor Models

To assess the anti-tumor growth activity of Compound 1 in animals, several in vivo mouse tumor models of different cancer origins were tested, including the following two in vivo PDX mouse PC models.

Figure 7A:
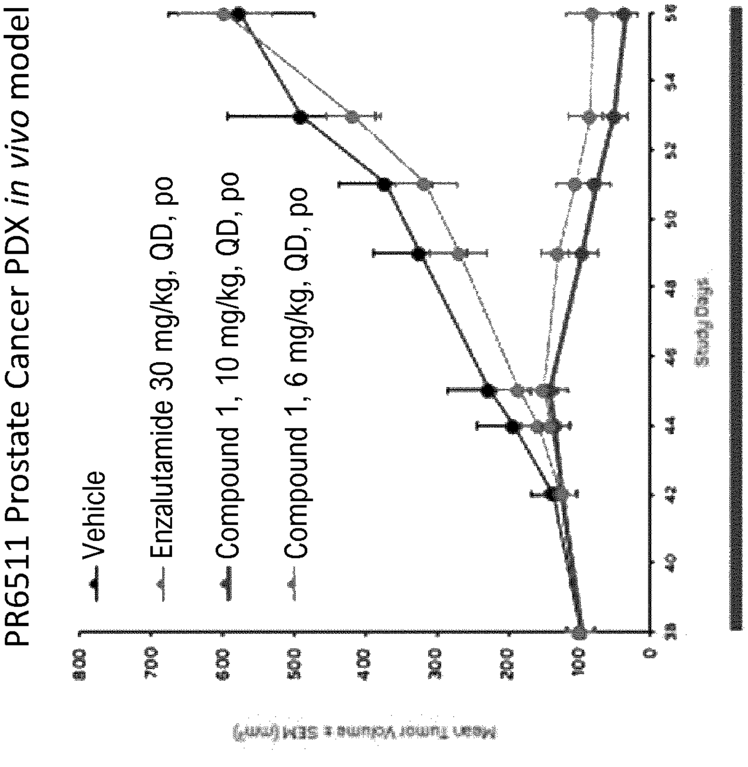
FIG. 7A shows the efficacy of Compound 1 in the in vivo mouse PDX prostate cancer model PR6511. PR6511 represents a model which was not responsive any more to enzalutamide treatment. The dose in the 10 mg/kg group was reduced to 3 mg/kg from day 51 onwards. The respective dosing periods are indicated as bars below the x-axis. QD: once daily treatment. po: per os.

In the PR6511 mouse PDX model, daily oral Compound 1 treatment (6 or 10 mg/kg) during the dosing phase (study days 38-57) resulted in substantial tumor regressions up to erradication of tumors in study mice (FIG. 7A).

Continued observation of mice for additional 3 weeks after the end of treatment showed no re-growth of tumors once tumors had fully regressed (data not shown).

Body weight loss was seen in all groups (incl. the vehicle group) during the dosing phase (study days 38-57) and dosing breaks were given to mice experiencing body weight loss of >10%. Due to weight loss, animals of the 10 mg/kg group received a reduced dose of 3 mg/kg on study days 51 to 57. Even though the dose of 10 mg/kg was effectively given only for approx. 8-10 days before dosing breaks and/or a dose reduction had to be introduced, the resulting anti-tumor activity of Compound 1 led to full tumor regressions (FIG. 7A).

Figure 7B:
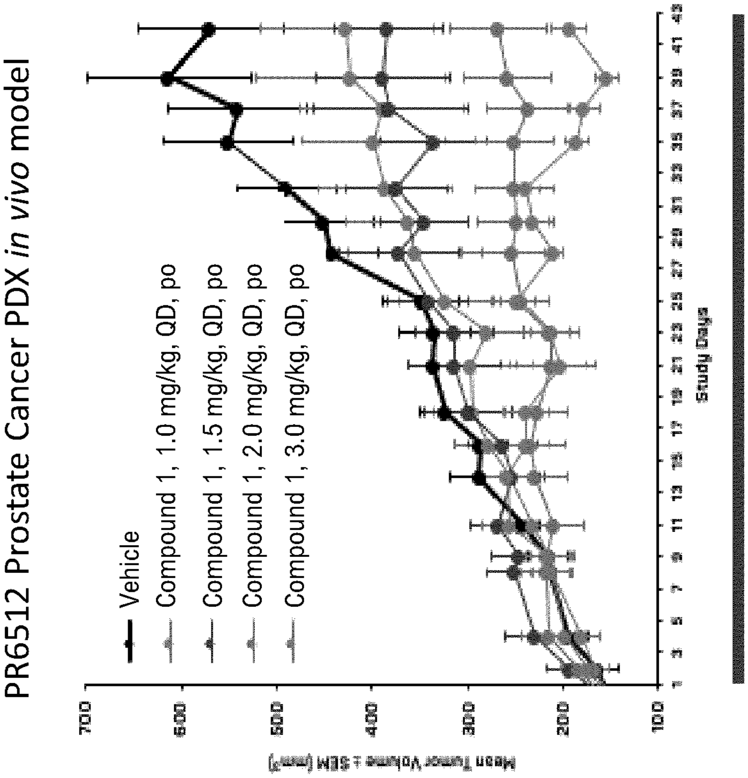
FIG. 7B the efficacy of Compound 1 in the in vivo mouse PDX prostate cancer model PR6512. The respective dosing periods are indicated as bars below the x-axis. QD: once daily treatment. po: per os.

Upon daily oral treatment with Compound 1 (at 1, 1.5, 2, and 3 mg/kg) in the PR6512 mouse PDX prostate cancer model, a dose dependent growth inhibition of tumors was observed. At the highest dose of 3 mg/kg administered QD a complete block of tumor growth was recorded (FIG. 7B). Again, an effect of the body weight was detected in all treatment groups (including the vehicle group).

Figure 8A:
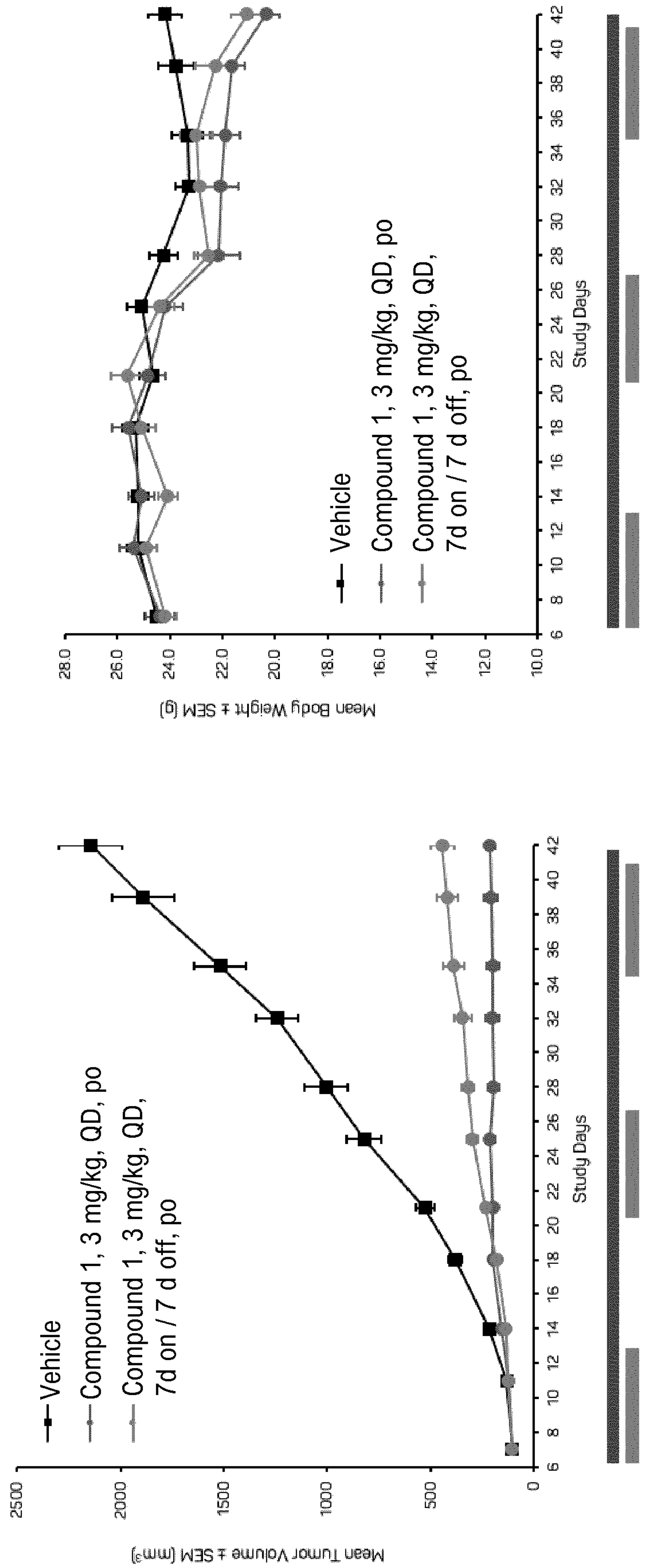
FIG. 8A shows Compound 1 applied in different dosing schemes to a 22Rv1 CDX prostate cancer in vivo mouse model. Left panel: Tumor growth curves. Right panel: Body weight development. The respective dosing regimen is indicated as bars below the x-axis. QD: once daily treatment; po: per os. 7d on/7d off: treatment "every other week" (i.e., repeated cycles of 7 days on treatment/7 days off treatment). p.o.: per oral.
Figure 8B:
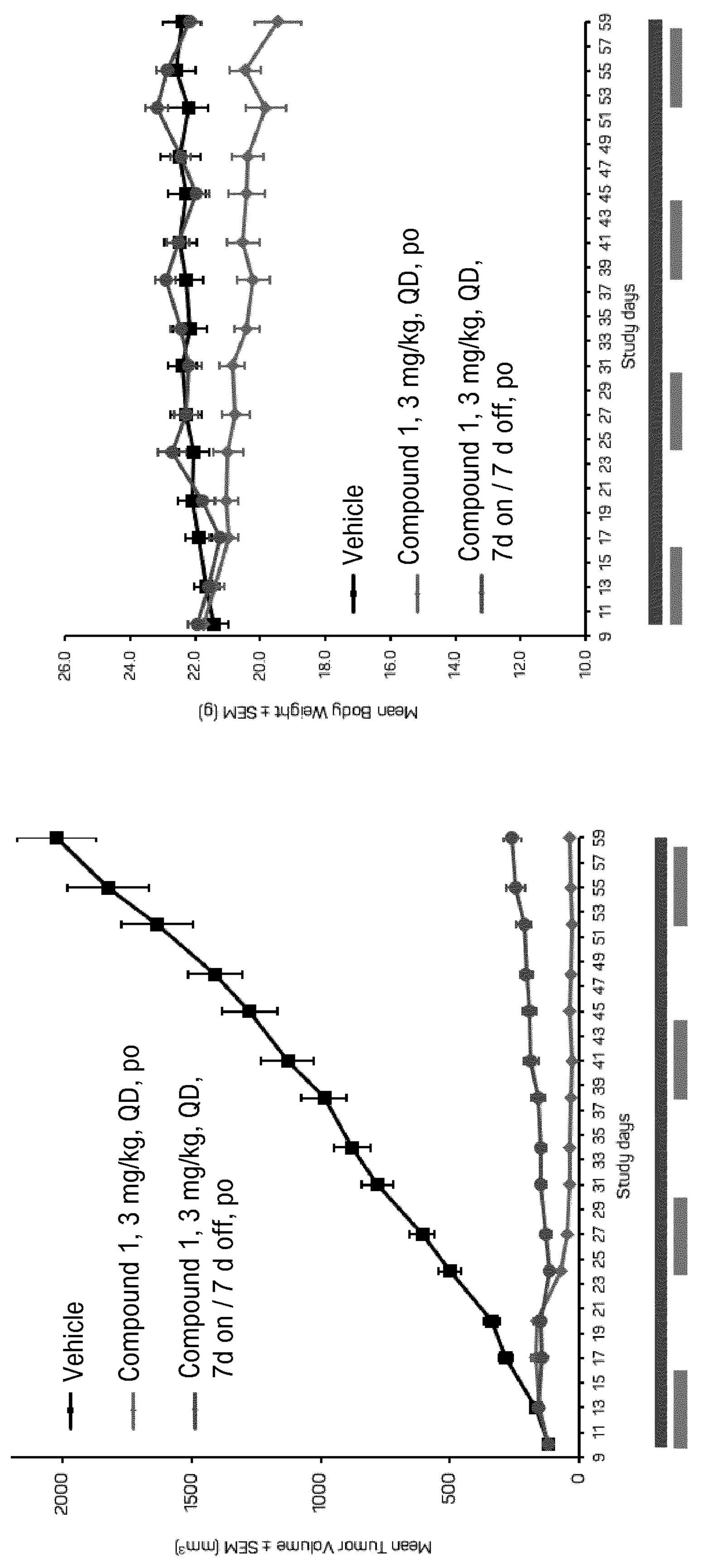
FIG. 8B shows Compound 1 applied in different dosing schemes to a NCI-H69 small cell lung cancer CDX in vivo mouse model. Left panel: Tumor growth curves. Right panel: Body weight development. The respective dosing periods are indicated as bars below the x-axis. QD: once daily treatment; po: per os. 7d on/7d off: treatment "every other week" (i.e., repeated cycles of 7 days on treatment/7 days off treatment). p.o.: per oral.
Figure 8C:
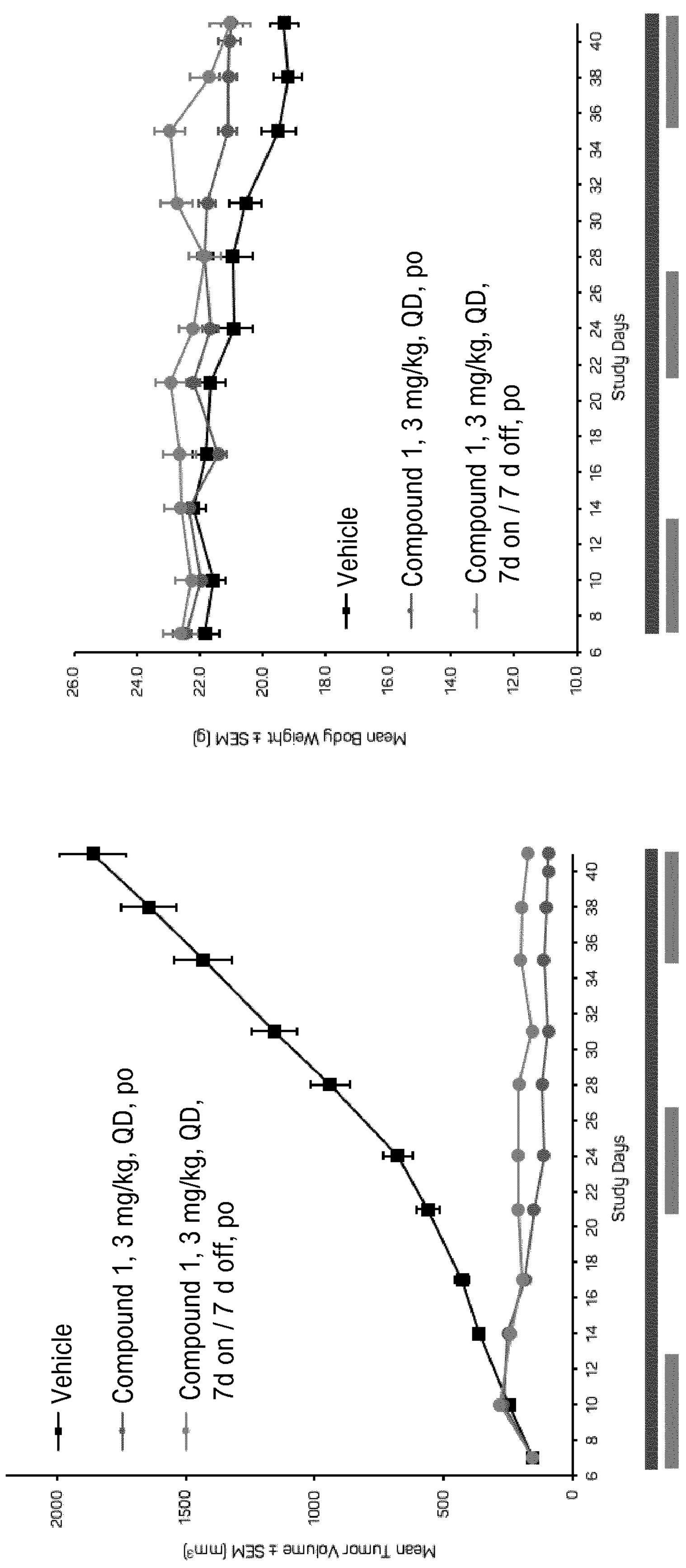
FIG. 8C shows Compound 1 applied in different dosing schemes to a SNU-5 gastric cancer CDX in vivo mouse model. Left panel: Tumor growth curves. Right panel: Body weight development. The respective dosing periods are indicated as bars below the below the x-axis. QD: once daily treatment; po: per os. 7d on/7d off: treatment "every other week" (i.e., repeated cycles of 7 days on treatment/7 days off treatment). p.o.: per oral.

In FIGS. 8A-8C, results from in vivo mouse CDX cancer models representing PC, SCLC, and gastric cancer are presented, and the results are described below.

In the 22Rv1 prostate cancer model (FIG. 8A), Compound 1 (3 mg/kg) was orally dosed either by daily administrations or on a basis of an "every other week" dosing regimen (i.e., repeated cycles of 7 days on treatment/7 days off treatment, also referred to herein as 7d on/7d off). 22Rv1 prostate cancer cells carry wild-type Rb and p53 genes and responded with a cytostatic growth inhibition to Compound 1. Treatment administered every other week in this model delivered almost the same anti-tumor growth activity for Compound 1 when compared to the same dose administered continuously every day, even though Compound 1 treatment was only administered for 3 out of 5 five weeks (FIG. 8) in total in the "every other week" regimen.

Similarly, in the SCLC model of NCI-H69 cells (FIG. 8B), oral Compound 1 treatment (3 mg/kg) administered every other week delivered almost the same anti-tumor growth activity for Compound 1 when compared to the same dose administered continuously every day, even though Compound 1 was only administered for 4 out of 7 five weeks in total, as it was only administered every other week. NCI-H69 cells carry a combined loss-of-function of Rb1 and p53 (Oser et al., Cancer Discov. 2019 February; 9(2):230-247. doi: 10.1158/2159-8290.CD-18-0389). Here, daily continuous dosing caused regressions of tumors (FIG. 8B), but at the same time induced a slight body weight loss which was not observed upon dosing "every other week", indicating that the intermittent dosing regimen was well tolerated.

Compound 1 (3 mg/kg) was administered orally to the gastric cancer CDX model of SNU-5 cells (FIG. 8C), which harbor a loss-of-function of p53 and mutations in the CDKN2A gene loci, the latter controlling the Rb and p53 pathways. The continuous daily administration on consecutive days and the "every other week" administration resulted in comparable anti-tumor efficacies of Compound 1, even though the dosing in the intermittent regimen was only administered for 3 out of 5 five weeks (FIG. 8C) in total.

In either model, NCI-H69 and SNU-5, both harboring mutations leading to the combined loss-of-function of the Rb1 and p53 pathways, a tendency to a stronger anti-tumor growth activity of Compound 1 was observed. In some of the animals even full tumor regressions were found. Furthermore, the "every other week" dosing regimen showed a general improved tolerability in terms of body weight upon Compound 1 treatment.

The anti-tumor activity of Compound 1 using a once weekly oral dosing regimen was also explored in mouse CDX models of cancer cell lines that harbor combined loss-of-functions of Rb1 and p53 pathways using the SNU-16 and SNU-5 gastric cancer, and the NCI-H69 SCLC CDX models. SNU-5 and SNU-16 cells harbor a p53 mutation and are mutant in the CDKN2A gene loci.

Figure 9A:
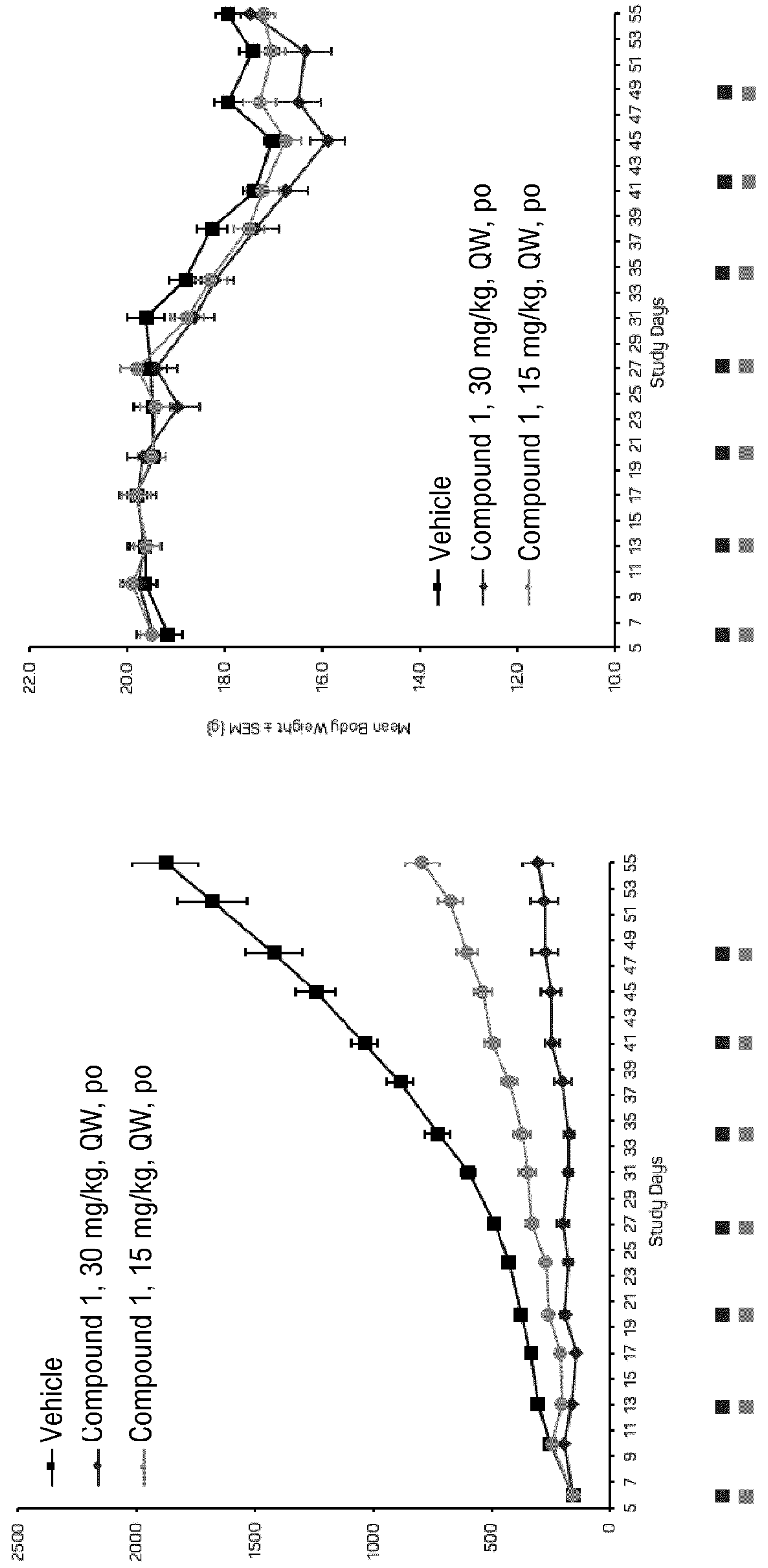
FIG. 9A shows Compound 1 applied in different dosing schemes to a SNU-5 gastric cancer CDX in vivo mouse model. Left panel: Tumor growth curves. Right panel: Body weight development. The respective dosing periods are indicated as bars/dots below the x-axis. QW: once weekly treatment. p.o.: per oral.
Figure 9B:
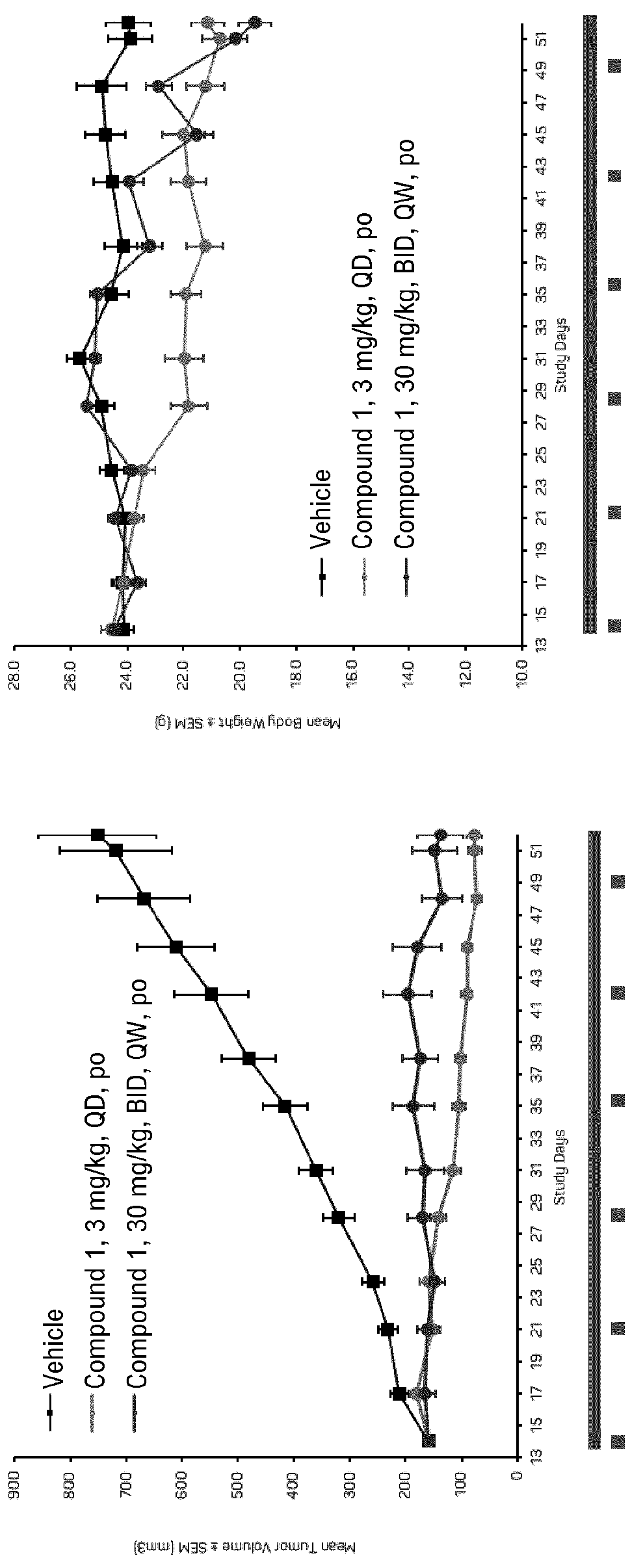
FIG. 9B shows Compound 1 applied in different dosing schemes to a SNU-16 gastric cancer CDX in vivo mouse model. Left panel: Tumor growth curves. Right panel: Body weight development. The respective dosing periods are indicated as bars/dots below the x-axis. QW: once weekly treatment. p.o.: per oral. QD: once daily treatment. BID: twice daily treatment. QW: once weekly treatment.
Figure 9C:
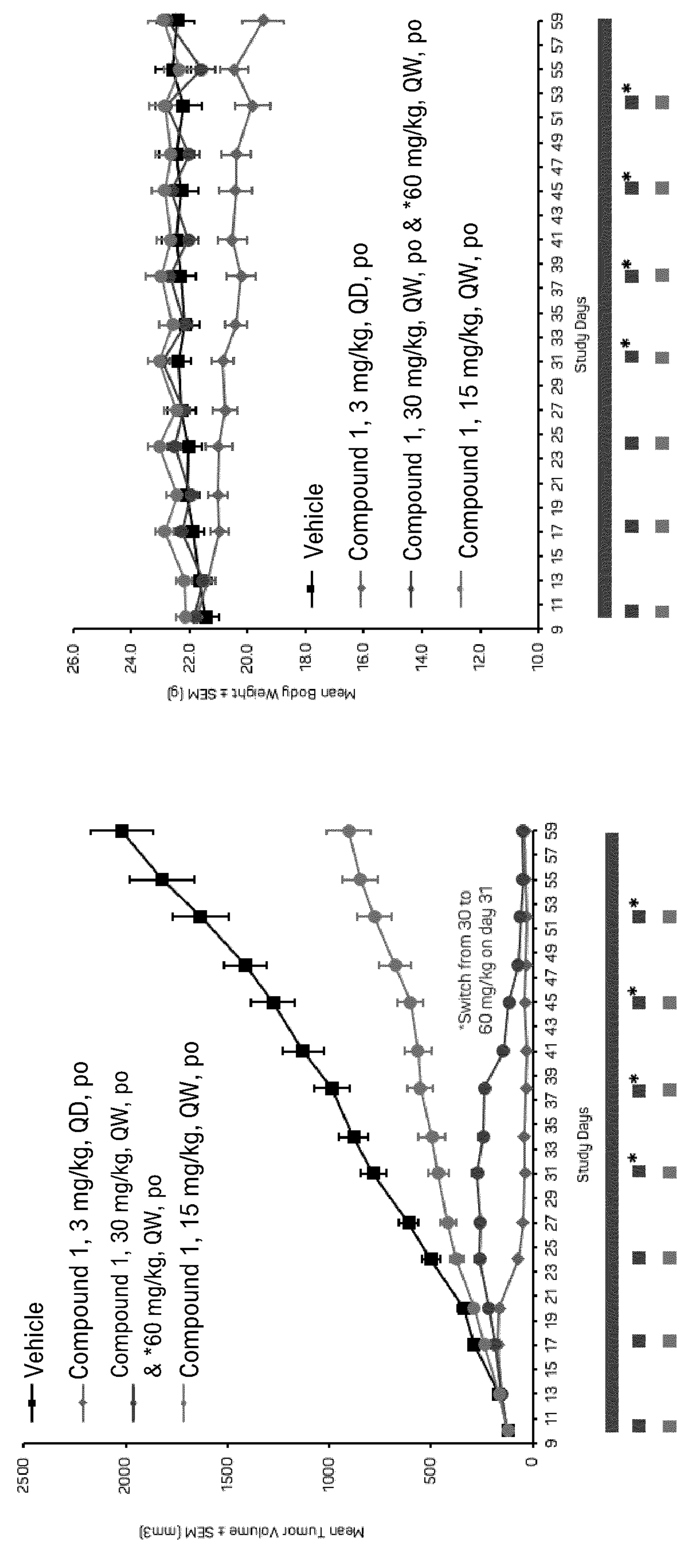
FIG. 9C shows Compound 1 applied in different dosing schemes to a NCI-H69 small cell lung cancer CDX in vivo mouse model. Left panel: Tumor growth curves. Right panel: Body weight development. The respective dosing periods are indicated as bars/dots below the x-axis. QW: once weekly treatment. p.o.: per oral. QD: once daily treatment. BID: twice daily treatment. QW: once weekly treatment. The 30 mg/kg group was given initially QW at 30 mg/kg and from day 31 onwards was given once weekly at 60 mg/kg, as indicated.

As described above, NCI-H69 SCLC cells display a combined loss-of-function for Rb and p53. All three models responded with strong tumor growth inhibition to Compound 1 upon repeated once weekly (QW) oral administration of Compound 1 (FIGS. 9A-9C). In the SNU-5 model (FIG. 9A), a Compound 1 (3, 30 mg/kg) dose-proportional response was observed which resulted in almost complete inhibition of tumor growth at the dose of 30 mg/kg administered once every seven days for 7 weeks. In the other gastric cancer model using SNU-16 cells (FIG. 9B), weekly administration Compound 1 at 30 mg/kg twice per day (BID) gave rise to a comparable anti-tumor efficacy when compared to Compound 1 administered continuously daily at 3 mg/kg (FIG. 9B). In the NCI-H69 SCLC model, administration of 30 mg/kg once every seven days, which was increased to 60 mg/kg for weeks 4 to 7, resulted in the same anti-tumor growth activity as compared to the continuous daily dosing of Compound 1 at 3 mg/kg (FIG. 9C). The intermittent dosing regimen did not cause significant body weight decreases in study mice (FIG. 9C, right panel).

The once every seven days dosing regimen for Compound 1, and the influence of differences in the functional status of Rb1 and p53, was evaluated using in vivo studies in two prostate cancer CDX models, i.e., 22Rv1 and NCI-H660.

Figure 10A:
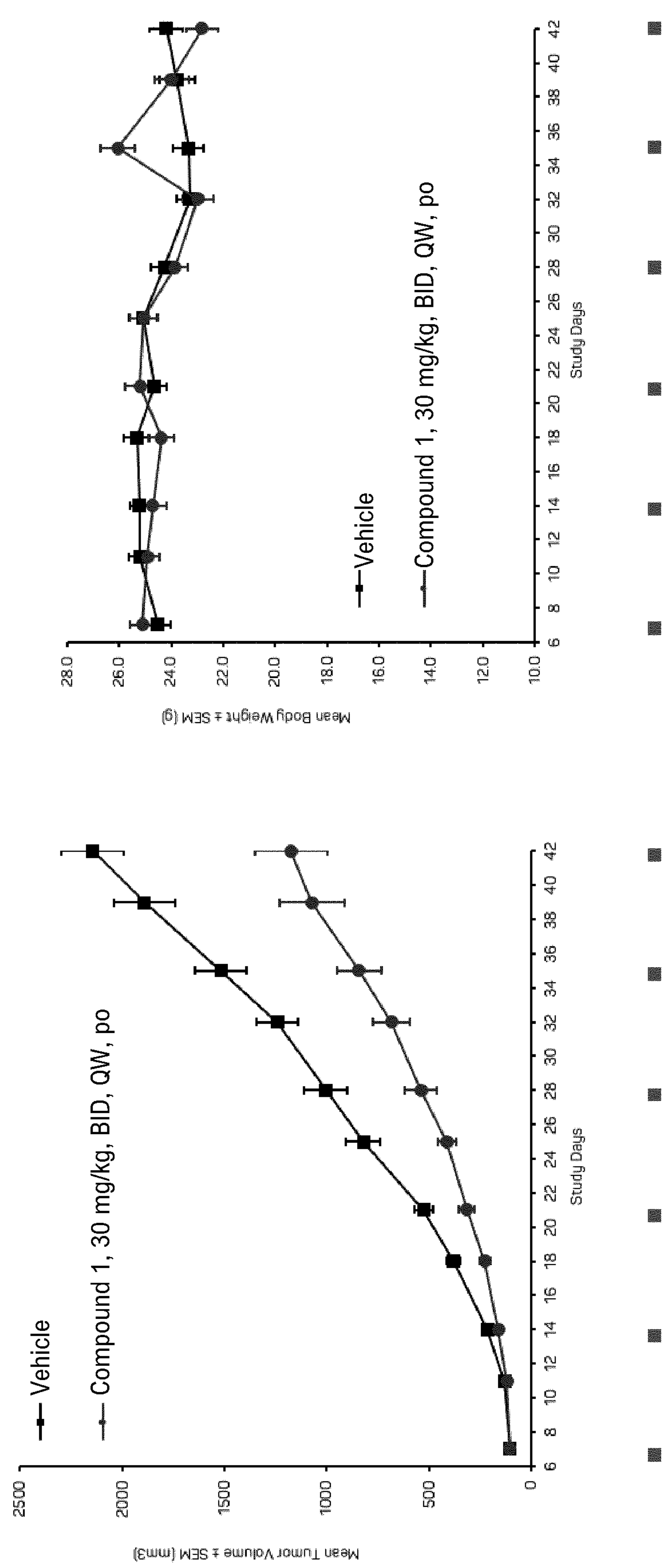
FIG. 10A shows results of repeated once weekly administrations of Compound 1 to a 22Rv1 prostate cancer in vivo mouse CDX model. Left panel: Tumor growth curves. Right panel: Body weight development. The dosing regimen is indicated as dots below the curves. BID: twice daily treatment. QW: once weekly treatment. p.o.: per oral.
Figure 10B:
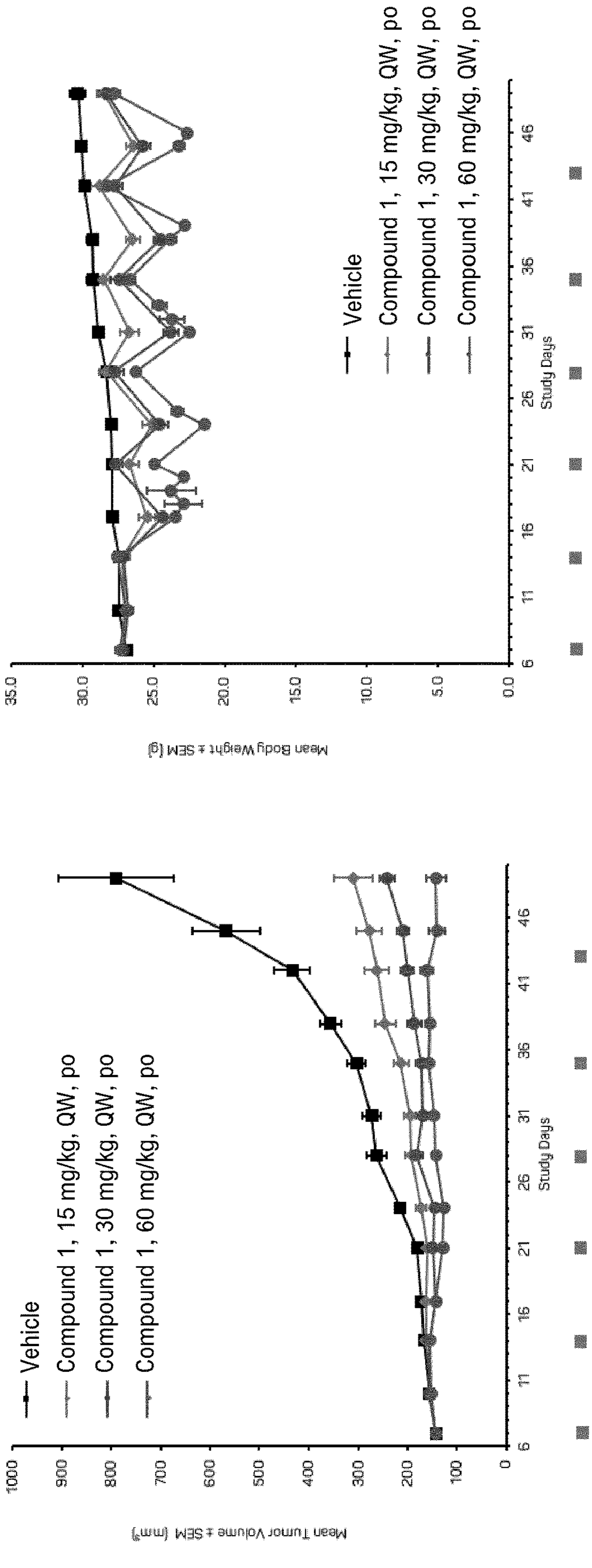
FIG. 10B shows results of repeated once weekly administrations of Compound 1 to a NCI-H660 prostate cancer in vivo mouse CDX model. Left panel: Tumor growth curves. Right panel: Body weight development. The dosing regimen is indicated as dots below the curves. BID: twice daily treatment. QW: once weekly treatment. p.o.: per oral.

Repeated once weekly doses of 30 mg/kg BID (total weekly dose of 60 mg/kg) of Compound 1 in the 22Rv1 prostate cancer model showed a tumor growth inhibition of approx. 50% (FIG. 10A). In contrast, administering the once weekly dosing scheme to the NCI-H660 prostate cancer model at 60 mg/kg Compound 1, representing the same total weekly dose as in the 22Rv1 model, caused a complete block of tumor growth (FIG. 10B). NCI-H660 cells represent a rather far advanced PC type in which not only the tumor suppressor functions of Rb1 and p53 have been lost (see Table 1). Furthermore, the cells already have developed a small cell phenotype characteristic of advanced treatment-resistant PC. In contrast, 22Rv1 tumor cells that are wild-type for Rb1 and p53 pathways were less sensitive to Compound 1 treatment when a once weekly dosing scheme was used.

In summary, with 10 mg/kg of Compound 1 (3 mg/kg on days 51-57) applied once daily in the PDX model PR6511 there were 2/8 partial responders, 4/8 complete responders and 3/8 tumor-free survivors. With 6 mg/kg of Compound 1, there were 2/8 partial responder, 3/8 complete responders and 3/8 tumor-free survivors.

The once weekly dosing schedule for Compound 1 delivered strong anti-cancer activity in several in vivo mouse tumor models treated up to seven weeks, and displayed a good tolerability profile. Additionally, cancer cells with a combined loss-of-function in the Rb and p53 tumor suppressor pathways (respectively in the CDKN2A locus) appear to be particularly sensitive to in vitro and in vivo Compound 1 treatment. Table 2 below summarizes the tumor growth inhibition (TGI) data of in vivo mouse cancer models administering Compound 1 according to the once weekly dosing schedule.

Furthermore, the experimental data for Compound 1 demonstrate "synthetic lethality" particularly in tumor cells harboring a combined Rb/p53 loss-of-function. Compound 1 particularly kills tumor cells with these genetic aberrations and which therefore lack an appropriate G1 cell cycle checkpoint, by disturbing DNA replication and increasing DNA damage. Besides advanced stages of PC, also several other tumor types (e.g., SCLC, osteosarcoma, triple negative breast cancer [TNBC]) frequently have acquired combined mutations and loss-of-function for Rb and p53, thus, proposing these additional tumor types as further therapeutic indications for Compound 1.

TABLE 2

Compound 1 tumor growth inhibition in CDX in vivo tumor mouse models of different cancer types and administering different dosing schemes

| Tumor model | Tumor growth inhibition (p-value)/Duration of treatment | | |
|---|---|---|---|
| | Once weekly dosing | | |
| Dosage (Mouse) | 15 mg/kg/day | 30 mg/kg/day (PAD) | 60 mg/kg/day*, ** |
| NCI-H69 | 58% (<0.001)/ 7 weeks | 76% (<0.001)/ 3 weeks | 103% (<0.001)/ 4 weeks, after 3 weeks at 30 mg/kg |
| SNU-5 | 62% (<0.001)/ 7 weeks | 91% (<0.001)/ 7 weeks | 98% (<0.001)/**5 weeks |
| SNU-16 | — | — | 103% (<0.001)/**6 weeks |
| NCI-H660 | 74% (0.002)/ 6 weeks | 84% (0.001) (6 weeks) | 99% (<0.001)/*6 weeks |
| 22Rv1 | — | — | 47% (0.001)/**5 weeks |
| DU-145 | — | — | 72 (<0.001)/**4 weeks |

In Table 2, tumor growth inhibition (TGI) calculations are based on additional growth of tumors, i.e., tumor sizes on the day of TGI estimation minus tumor sizes at the start of treatment are used for calculations. Values larger than 100% indicate tumor regression. TGI values of more than 70% are highlighted in bold and are representative of having administered a pharmaceutically active dose (PAD) of Compound 1. The total daily dose of 60 mg/kg was administered as *single dose or given as **30 mg/kg BID (twice daily).

Example 3: Single Dose Pharmacokinetic and Toxicokinetic Studies

Exploratory Pilot Single Dose Oral and Intravenous PK Studies in CD1 Mice

These studies analyzed the PK profile of Compound 1 following a single oral gavage or single intravenous dose to CD-1 mice.

Compound 1 (mesylate salt) was administered to four groups of male mice (n=4/group) as a single oral (po) gavage administration at dose levels of 5, 10, 20, and 50 mg/kg/adm or as single intravenous (IV) dose at 5 and 50 mg/kg/adm. The vehicle was 1% methylcellulose with 0.1% Tween-80 in study AMP800 and 5% dextrose in water in study AMP799. Blood samples were collected at pre-dose, 10 minutes, 40 minutes, 2, 4, and 7 hours after administration for analysis of Compound 1 concentrations in blood by liquid chromatography—tandem mass spectroscopy (LC-MS/MS) and subsequent calculation of PK parameters.

Pharmacokinetics parameters calculated from blood Compound 1 concentration time profiles are summarized in Table 3 below.

TABLE 3

Compound 1 PK parameters after oral single dose in CD-1 mice

| Dosage (Mouse) (mg/kg) | $T_{max}$ (h) | $C_{max}$ (ng/L) | $AUC_{0-t}$ (ng/L*h) | $AUC_{0-inf}$ (ng/L*h) | $T_{1/2}$ (h) |
|---|---|---|---|---|---|
| Oral Administration | | | | | |
| 5 | 0.17 | 40 | 179 | 246 | 4.0 |
| 10 | 0.17 | 127 | 310 | 471 | 5.6 |
| 20 | 0.17 | 788 | 1967 | 2490 | 3.2 |
| 50 | 0.67 | 1036 | 2876 | 3382 | 2.6 |
| Intravenous Administration | | | | | |
| 5 | 0.17 | 715 | 1027 | 1112 | 2.3 |
| 50 | 0.17 | 7064 | 12179 | 12973 | 1.6 |

AUC: area under the curve,
$C_{max}$: maximal concentration,
$t_{1/2}$: half-life,
$T_{max}$: time to $C_{max}$.

a Single Dose Intravenous and Oral Pharmacokinetics Study in Beagle Dogs

This study determined the PK profile of Compound 1 following a single intravenous injection or oral gavage administration to Beagle dogs.

Compound 1 (citrate salt) was administered to two groups of dogs (n=1/sex/group) once by intravenous injection on Day 1, dose levels of 1 (Group 1) or 4 (Group 2) mg/kg/adm, and once by oral gavage on Day 3, dose levels of 3 (Group 1) and 12 (Group 2) mg/kg/adm, respectively. The vehicle was 5% dextrose in water for intravenous and aqueous citrate buffer solution for oral gavage administrations. Relative to each dosing on Days 1 and 3, series of blood samples were collected at pre-dose, 0.083, 0.25, 0.5, 1, 2, 4, and 7 hours for intravenous or at 0.25, 0.5, 1, 2, 4, 7, and 24 hours for oral gavage administration for analysis of Compound 1 concentrations in blood and subsequent calculation of PK parameters. Additional endpoints monitored during this study included mortality, clinical observations and body weight.

Administration of Compound 1 through intravenous injection at doses of 1 and 4 mg/kg/adm or by oral gavage at doses of 3 and 12 mg/kg/adm was well tolerated with no Compound 1-related mortality, or changes in clinical signs and body weight. Pharmacokinetics parameters calculated from blood/serum/plasma Compound 1 concentration time profiles are summarized in Table 4 below.

TABLE 4

Compound 1 PK parameters after intravenous or oral single dose in Beagle dogs

| Dosage (Dog) (mg/kg) | Route | $T_{max}$ (h) | $C_{max}$ (ng/L) | $AUC_{0-t}$ (ng/L*h) | $AUC_{0-inf}$ (ng/L*h) | $T_{1/2}$ (h) | Vss (Vz/F) (mg/kg)/ (nmo/ L) | Cl (mg/kg)/ (nmo/L)/ h |
|---|---|---|---|---|---|---|---|---|
| 1 | IV | 0.08 | 140 | 63 | 89 | 0.5 | 0.004 | 0.0057 |
| 4 | | 0.08 | 1062 | 1288 | 1450 | 2.5 | 0.004 | 0.0014 |
| 3 | po | 0.25 | 73 | 182 | 289 | 2.6 | (0.019) | 0.0052 |
| 12 | | 0.25 | 835 | 1907 | 2391 | 3.3 | (0.012) | 0.0025 |

AUC: area under the curve,
$C_{max}$: maximal concentration,
$t_{1/2}$: half-life,
$T_{max}$: time to $C_{max}$,
Vss: volume of distribution at steady state,
Vz/F: apparent volume of distribution during terminal phase,
IV: intravenous injection administration, and
po: oral gavage administration.

a Single Dose Oral Gavage or Intravenous Injection Pharmacokinetics Study of Compound 1 in Female Cynomolgus Monkeys The objective of the study was to determine the PK profile of Compound 1 following a single oral gavage or intravenous injection administration on 5 different occasions to female cynomolgus monkeys.

Compound 1, was administered as consecutive single doses on 5 occasions, separated by a washout period, by either oral gavage (4 and 12 mg/kg, Days 1 and 8) or by slow bolus intravenous (IV) injection (0.2 and 0.6 mg/kg, Days 15 and 22) to a group of female monkeys. In a subset of dosing the influence of grapefruit juice was evaluated (Day 34). Each single dose (Days 1, 8, 15, 22, and 34) was separated by a 7-day washout period. Blood samples were collected on Days 1, 8, 15, 22 and 34 at selected time points, i.e., 15 min, 30 min, as well as 1, 2, 4, 6, 8, and 24 hours relative to treatment for analysis of the concentration of Compound 1 in plasma and subsequent calculation of PK parameters. Additional parameters monitored included mortality, clinical observations and body weight.

The single dose oral administration of Compound 1 to cynomolgus monkeys at doses up to 12 mg/kg did not result in any adverse clinical signs. A decrease in appetite was observed in animals administered Compound 1 intravenously at doses up to 0.6 mg/kg.

After oral administration, exposure to Compound 1 (based on AUCO-Tlast, AUCINF and Cmax values) increased dose-dependently and generally in a more than dose-proportional manner (Table 5). A tendency towards a higher Cmax (2-fold increase) was observed in animals receiving grapefruit juice prior to dosing when compared to animals that did not receive grapefruit juice. Compound 1 was cleared (Cl) at a mean rate of 2590±83.9 and 2460±42.7 mL/hr/kg on Days 15 and 22, respectively. The mean volume of distribution (Vz) was 17400±2200 and 16900±1910 mL/kg on Days 15 and 22, suggesting that Compound 1 was largely distributed among tissues.

TABLE 5

Compound 1 PK parameters after intravenous or oral single dose in cynomolgus monkeys

| Dosage (Monkey) (mg/kg) | Route | $T_{max}$ (h) | $C_{max}$ (ng/mL) | $AUC_{0-t}$ (ng/mL*h) | $AUC_{0-inf}$ (ng/mL*h) | $T_{1/2}$ (h) |
|---|---|---|---|---|---|---|
| 0.2 | IV | 0.08 | 47.6 | 76.2 | 77.4 | 4.64 |
| 0.6 | | 0.08 | 162.0 | 240.0 | 244.0 | 4.74 |
| 4 | po | 0.50 | 5.52 | 16.9 | 17.3 | 4.7 |
| 12 | | 0.83 | 53.60 | 130.0 | 133.0 | 5.46 |

AUC: area under the curve,
$C_{max}$: maximal concentration,
$t_{1/2}$: half-life,
$T_{max}$: time to $C_{max}$,
IV: intravenous injection administration, and
po: oral gavage administration.

Example 4: Repeat-Dose Pharmacokinetic and Toxicokinetic Studies

28-Day Once Weekly Oral Repeated-Dose DRF Study in CD-1 Mice

This study explored the PK of Compound 1 after once weekly oral administration of 300 and 600 mg/kg/week for 4 consecutive weeks to male CD-1 mice.

Compound 1 (mesylate salt) was administered in 4 weekly doses by oral gavage to groups of male CD-1 mice (n=3/group) at dose levels of 300 and 600 mg/kg bodyweight per week. A suspension of 0.5% methylcellulose (w/v) in sterile water served as vehicle. Blood samples for PK analysis were collected after the second (Day 8) and fourth (Day 22) dosing at pre-dose, 0.25, 0.5, 1, 2, 4, 8, and 24 hours (the latter time point only after the 2nd dose) after administration.

Total plasma concentrations of Compound 1 were analyzed using a qualified LC-MS/MS method. PK parameters are presented in the Table 6 below.

TABLE 6

| Compound 1 PK parameters in mice after repeated weekly oral administrations | | | | | |
|---|---|---|---|---|---|
| Dosage (Mouse) (mg/kg/week) | Dose | $C_{max}$ (ng/mL) | $T_{max}$ (h) | $t_{1/2}$ (h) | $AUC_{0-8h}$ (ng/ml*h) |
| 300 | $2^{nd}$ | 8,127 | 1.0 | 4.1 | 13,579 |
| | $4^{th}$ | 8,372 | 1.3 | n.c | 38,246 |
| 600 | $2^{nd}$ | 13,364 | 5.7 | n.c. | 47,807 |
| | $4^{th}$ | 28,831 | 0.5 | 85.8 | 124,992 |

n.c., not calculated

At the 300 mg/kg Compound 1 dose level, the maximum plasma concentration was observed at 8127 ng/ml on Week 2 and remained at a similar level at 8373 ng/ml on Week 4. The AUC(0-8 h) was calculated at 13579 ng*h/mL on Week 2 and 38246 ng*h/mL on Week 4. With an administration of 600 mg/kg Compound 1, the Cmax was observed at 13365 ng/ml on Week 2 and was nearly doubled at 28832 ng/ml on Week 4. The AUC(0-8 h) was calculated at 47807 ng*h/mL on Week 2 and 124992 ng*h/mL on Week 4.

14-Day Daily Oral Repeated-Dose Exploratory Study in CD-1 Mice

This study explored the TK profile of Compound 1 after 14 days once daily oral dosing in male and female CD-1 mice.

Compound 1 (mesylate salt) was administered once daily for 14 consecutive days by oral gavage to groups of CD-1 mice (n=8/sex/group) at dose levels of 0 (control), 1, 5, 10 or 15 mg/kg/day. A suspension of 0.5% Methylcellulose (w/v) and 0.1% Polysorbate 80 (Tween 80) (v/v) was used as vehicle. For TK investigations sparse blood sampling was performed on treatment Days 1 and 14; three blood samples per animal and day were collected either pre-dose, 2 and 8 hours after administration (4 male and female animals per group) or 1, 4, and 24 hours (remaining 4 male and 4 female animals per group) after administration.

TK analysis revealed a generally dose dependent and dose-proportional increase in $C_{max}$ and AUC on Day 1 with a trend for accumulation after repeated dosing on Day 14. No marked differences between genders were observed (Table 7).

TABLE 7

| Compound 1 TK parameters in mice after 14 days of oral administration | | | | | |
|---|---|---|---|---|---|
| Dosage (Mouse) | | $C_{max}$ (ng/ml) | | $AUC_{0-tz}$ (ng/ml*h) | |
| (mg/kg) | Sex | Day 1 | Day 14 | Day 1 | Day 14 |
| 1 | M | 10.9 | 16.3 | 55.35 | 107.9 |
| | F | 6.4 | 16.6 | 33.10 | 111.7 |
| 5 | M | 42.9 | 90.0 | 225.15 | 607.3 |
| | F | 67.6 | 114.6 | 257.95 | 477.95 |
| 10 | M | 64.8 | 105.0 | 360.70 | 781.6 |
| | F | 60.5 | 97.7 | 304.50 | 690.1 |
| 15 | M | 132.7 | 102.0 | 688.70 | 717.2 |
| | F | 140.0 | 150.8 | 710.60 | 1088.65 |

AUC: area under the curve,
$C_{max}$: maximal concentration.

5-Day Daily Intravenous Repeated-Dose TK Study in CD-1 Mice

The aim of the present study was to explore the TK of Compound 1 after 5 days of once daily intravenous dosing in male and female CD-1 mice, with a subsequent recovery phase of 9 days.

Compound 1 (mesylate salt) was administered once daily for 5 consecutive days by intravenous injection to groups of CD-1 mice (n=8/sex/group) at dose levels of 0 (control), 0.5, 2, 6, or 12 mg/kg/day. A suspension of 0.5% methylcellulose (w/v) in sterile water was used as vehicle. Blood samples were collected for hematology, clinical chemistry (Day 6 and 15), and pharmacokinetics evaluation.

TK analysis revealed a generally dose dependent increase in CO and AUC on Day 1 and Day 5. On Day 1, the calculated group mean initial blood concentration (CO) of Compound 1 was 111, 386, 1257, and 1725 ng/mL for the doses of 0.5, 2, 6, and 12 mg/kg/day. In all groups, the terminal half-life ranged between 1.1 and 1.3 h. On Day 5, a difference of CO between genders was noted. Hence, in male mice, CO was calculated at 191, 275, 778 and 1531 ng/ml and in female mice at 112, 391, 641, and 1548 ng/ml for doses of 0.5, 2, 6 and 12 mg/kg/day, respectively. Over the dose interval, the elimination half-life ranged between 1.1 and 1.9 h. Like on Day 1, $AUC_{(0-tz)}$ was comparable between male and female animals on Day 5.

Compound 1 at dose levels of 0.5, 2, 6, and 12 mg/kg/day was well tolerated in mice when dosed intravenously once daily for 5 consecutive days. Toxicokinetic revealed a generally dose dependent increase in CO and AUC on Day 1 and Day 5.

28-Day Once Weekly Oral Repeated-Dose DRF TK Study in Beagle Dogs

The objective of the study was to determine the TK profile of Compound 1 following 4 weekly oral administrations to Beagle dog and to assess reversibility of any changes following a 13-day recovery period.

The test item Compound 1 (mesylate salt) was administered in 4 weekly doses by oral gavage to groups of Beagle dogs (n=2/sex/group) at dose levels of 10, 15, and 20 mg/kg bodyweight per week. A suspension of 0.5% methylcellulose (w/v) in sterile water served as vehicle. Blood samples for PK analysis were collected for each dosing day (Day 1, 8, 15, and 22) at pre-dose, 0.25, 0.5, 1, 2, 4, 6, 8, 12, and 24 hours after administration.

Total plasma concentrations of Compound 1 were analyzed using a qualified LC-MS/MS method. PK parameters are presented in Table 8 below.

TABLE 8

| PK Parameters weekly dosing dog | | | | | | | | | |
|---|---|---|---|---|---|---|---|---|---|
| | | $C_{max}$ (ng/mL) | | | | AUC (ng/mL*h) | | | |
| Dosage (mg/kg) | No. of dogs | Day 1 | Day 8 | Day 15 | Day 22 | Day 1 | Day 8 | Day 15 | Day 22 |
| 10 | 4 (2M/2F) | 536 | 512 | 497 | 360 | 1722 | 1593 | 1659 | 1171 |
| 15 | 2 (1M/1F) | 752 | 506 | nd | nd | 2626 | 2298 | nd | nd |
| 20 | 4 (2M/2F) | 994 | nd | nd | nd | 3012 | nd | nd | nd |

AUC: area under the curve,
$C_{max}$: maximal concentration.
nd: not determined.

Dosing of the 20 mg/kg/adm dose group was discontinued due to a serious adverse event (SAE) on day 5. Dosing at 15 mg/kg/adm was limited to 2 weekly doses, since animals were subjected to necropsy investigation 3 days after the second dose (Day 8) in order to investigate possible macroscopic changes during the treatment period. n.d.: not determined. AUC parameters were calculated using GraphPad Prism version 9.

5-Day Daily Dosing Oral Repeated-Dose Pilot Study in Beagle Dogs

The objective of the study was to determine the TK profile of Compound 1, following its daily administration through oral gavage for 5 consecutive days to Beagle dogs. Compound 1 (mesylate salt) was administered daily to groups of dogs (n=2/sex/group) by oral gavage (PO) for 5 consecutive days at doses of 1.5 and 2 mg/kg/day. The vehicle was 0.5% (w/v) methylcellulose in sterile water. For TK evaluation blood samples were collected from each dog on Days 1 and 5 at the following timepoints relative to dosing: pre-dose, 15 min, 30 min, as well as 1, 2, 4, 6, 8, 12, and 24 hours post-dose.

In the 1.5 mg/kg group 1, maximum observed plasma concentrations ($C_{max}$) were 25.4 (Day 1) and 44.6 ng/mL on Day 5. $T_{max}$ was reached approximately at 0.5 hours. Total AUC ($AUC_{(0-inf)}$ was respectively calculated at 116 and 213 ng/mL*h. The elimination half-life was determined at 4.5 h and 6.2 h on Day 1 and Day 5, respectively. In the 2 mg/kg group, $C_{max}$ values were 33.6 (Day 1) and 32.3 (Day 5) ng/ml, reached at approximately 0.4 and 2.1 hours, respectively. Total AUC was calculated at 173 (Day 1) and 270 (Day 5) ng/mL*h. T1/2 was determined at 4.7 and 8.6 hours on Day 1 and Day 5, respectively.

14-Day Daily Dosing Oral Repeated-Dose DRF Study in Beagle Dogs

The objective of this dose-range-finding study was to select the dose levels for a potential subsequent toxicity study of Compound 1 by oral administration to Beagle dogs.

Compound 1 (citrate salt) administration in this study was intended once daily for up to 14 consecutive days by oral gavage to groups of naïve Beagle dogs (n=1/sex/group) at dose levels of 0.1, 0.3, 1, 3, 6, or 12 mg Compound 1 per kg bodyweight and day in 0.5% methylcellulose by using a staggered approach. The actual dose levels and durations of dosing were flexibly adapted according to PK and signs of tolerability. For TK evaluation blood samples were collected from each dog on Days 1 and 14 at pre-dose, 1, 2, 4, 8, 12, and 24 hours post-dose.

TK analysis showed Compound 1 mean $C_{max}$ plasma levels of 0.6, 2.3, 8.6, 23.8, 114.1, and 182.0 ng/mL on Day 1 in animals treated at 0.1, 0.3, 1, 3, 6, or 12 mg/kg/day, respectively, with $T_{max}$ values reached after 1 to 2 hours after administration. Total $AUC_{(o-inf)}$ was calculated at 5.6, 13.8, 63.8, 171.6, 734.8, and 936.4 ng/mL*h. The elimination half-life determined in the range from 3.4 to 6.2 hours on Day 1. On Day 14, Compound 1 group mean $C_{max}$ plasma levels of 0.4 and 3.8 ng/mL plasma were detected for animals treated with 0.1 and 0.3 mg/kg/day, respectively, at a $T_{max}$ of 1 hour and terminal elimination half-lives of 4.7 to 5.5 hours. Potential accumulations over time (Day 1 versus Day 14) of drug exposure could only be investigated for animals treated with 0.1 or 0.3 mg/kg/day. For the 0.1 mg/kg/day group no accumulation with time was noted, in the 0.3 mg/kg/day group a slight increase over time was detectable.

28-Day Once Weekly Oral Repeated-Dose DRF Study in Cynomolgus Monkeys

The objective of the study was to determine the TK profile of Compound 1 following 4 weekly oral administrations to cynomolgus monkeys and to assess reversibility of any changes following a 13-day recovery period.

Male and female cynomolgus monkeys (n=1/sex/group) were orally administered Compound 1 (mesylate salt) at dose levels of 30, 45, 60, or 90 mg/kg/administration for 4 consecutive doses on study days 1, 8, 15, and 22. The vehicle was 0.5% (w/v) methyl cellulose 400 in sterile water. For TK analysis blood samples were collected from each monkey on Days 1, 8, 15 and 22 at pre-dose, 15 min, 30 min, as well as 1, 2, 4, 6, 8, 12, and 24 hours post-dose. Non-compartmental analysis of Compound 1 blood concentrations data sets was performed using the Phoenix® WinNonlin® software (version 6.4).

Over the dose range, exposure to Compound 1 increased dose-dependently, however, some increases were more than dose-proportional between different doses. There were no noteworthy sex-related differences in any of the measured toxicokinetic parameters. Accumulation ratios suggested that Compound 1 did not accumulate when administered once weekly for 4 weeks to cynomolgus monkeys at doses up to 60 mg/kg. PK parameters are given in Table 9.

TABLE 9

PK parameters after repeated weekly dosing to cynomolgus monkeys

| Dosage (Monkey) | | $t_{1/2}$ (h) | | $T_{max}$ (h) | | $C_{max}$ (ng/mL) | | $AUC_{0-Tlast}$ (ng/mL*h) | |
|---|---|---|---|---|---|---|---|---|---|
| (mg/kg) | Sex | Day 1 | Day 22 | Day 1 | Day 22 | Day 1 | Day 22 | Day 1 | Day 22 |
| 30 | M | 4.9 | 2.6 | 0.63 | 2 | 229 | 171 | 721 | 576 |
| | F | 6.4 | 5.5 | 0.63 | 1.25 | 296 | 223 | 894 | 874 |
| 45 | M | 7.6 | 5.2 | 1.5 | 1.25 | 1040 | 1350 | 2950 | 3910 |
| | F | 6.3 | 5.8 | 1.5 | 1.5 | 1460 | 1650 | 4130 | 4810 |
| 60 | M | 7.5 | 5.7 | 0.5 | 1 | 449 | 2430 | 1170 | 6710 |
| | F | 3.8 | 4.4 | 1.0 | 2 | 1830 | 4480 | 7440 | 17400 |
| 90 | M | 4.2 | n.d. | 0.63 | n.d. | 7300 | n.d. | 22800 | n.d. |
| | F | 4.3 | n.d. | 1.5 | n.d. | 5030 | n.d. | 18700 | n.d. |

n.d.: not determined.
Compound 1 PK parameters by non-compartmental analysis.
The 90 mg/kg dose group was discontinued after Day 7 due to an adverse event.
No data for this group are available for Day 22.

5-Day Daily Oral Repeated-Dose Pilot Study in Cynomolgus Monkeys

The objective of the study was to determine the TK profile of Compound 1 following its daily administration through oral gavage (po) for 5 days to cynomolgus monkeys.

Naïve male and female cynomolgus monkeys (2 animals/sex/group) were orally administered Compound 1 (mesylate salt) at dose levels of 8, 12 or 16 mg/kg/day for 5 consecutive days. The vehicle was 0.5% (w/v) methyl cellulose 400 in sterile water. For TK evaluation blood samples were collected from each animal on Days 1 and 5 at pre-dose, 15 min, 30 min, as well as 1, 2, 4, 6, 8, 12, and 24 hours post-dose.

Peak serum levels ($C_{max}$) of Compound 1 on Day 1 were 45, 42, and 136 ng/mL for the 8, 12, and 16 mg/kg/day dose groups with $T_{max}$ values in the range of approximately 0.5 to 0.9 hours. On Day 5 of the dosing period $C_{max}$ values were 64, 72 and 112 ng/mL for the 8, 12, and 16 mg/kg/day dosing groups, respectively; with $T_{max}$ values reached after about 0.5 to 1.75 hours. The half-life ($T_{1/2}$) of Compound 1 was among all groups and time points was about 5 to 7 hours. Total AUC of Compound 1 on Day 1 was calculated at 85, 106, and 351 ng/mL*h and on Day 5 at 175, 329, and 561 ng/mL*h for the 8, 12, and 16 mg/kg/day dose groups, respectively. Overall $C_{max}$ and AUC appeared to increase in a dose-proportional manner, with a trend to over-proportional exposure at the 16 mg/kg/day dose level.

14-Day Daily Oral Repeated-Dose DRF Study in Cynomolgus Monkeys

The objective of this exploratory study was to assess the TK profile of Compound 1 when repeatedly administered via the oral route to cynomolgus monkeys.

Compound 1 (mesylate salt) administration in this dose-range-finder study was intended once daily for up to 14 consecutive days by oral gavage to groups of naïve cynomolgus monkeys (n=1/sex/group) at dose levels of 0.5, 4, 8, or 12 mg Compound 1 per kg bodyweight and day, using a staggered approach. The vehicle was 0.5% Methylcellulose in water. The actual dose levels and durations of dosing were flexibly adapted according to signs of tolerability and PK: Group 1 animals were dosed at 0.5 mg/kg/day for 10 days and after a 4-day washout phase for additional 12 days at 4 mg/kg/days; Group 2 animals at 12 mg/kg/day for 11 days; Group 3 animals at 8 mg/kg for 10 (males) or 9 (females) days; and Group 4 animals at 8 mg/kg for 5 days, respectively, as summarized in Table 10.

TABLE 10

Dosing Groups and Durations

| Dosage (Monkey) (mg/kg/day) | No. Total Doses (n/animal) | Group No. |
|---|---|---|
| 0.5 | 10 | 1 |
| 4 | 12 | |
| 8 | 5 | 4 |
| 8 | 9/10 | 3 |
| 12 | 11 | 2 |

The animals in the final group 4 were dosed orally once daily or 5 days with 8 mg/kg Compound 1 before a 9-day recovery phase was given.

The $C_{max}$ and AUC values for Compound 1 revealed a dose-related exposure to Compound 1 among the different dosing groups with no obvious gender differences (Table 11). $T_{max}$ after oral administration was observed at around 1 to 1.5 hours after administration. The calculated mean terminal plasma elimination half-lives of Compound 1 in general ranged from 4.4 to 8.4 hours after oral administration. No significant accumulation was observed after repeated dosing, thus, the accumulation factor over the different dose groups ranged from 1.05 to 2.45.

TABLE 11

PK parameters after repeated daily dosing to cynomolgus monkey

| Dose (Group, Monkey) (mg/kg) | Day | $T_{max}$ (h) | $C_{max}$ (ng/ml) | $AUC_{0-tz}$ (ng/ml*h) | $T_{1/2}$ (h) |
|---|---|---|---|---|---|
| 0.5 | 1 | 1.5 | 0.24 | 0.7 | 4.9 |
| (Gr. 1) | 7 | 1.0 | 0.18 | 1.2 | 18.5 |
| 4 | 1 | 1.0 | 2.95 | 10.5 | 4.4 |
| (Gr. 1) | 5 | 1.0 | 2.30 | 9.5 | 8.4 |
| | 11 | 1.0 | 3.06 | 10.9 | 5.1 |
| 8 | 1 | 1.0 | 8.95 | 30.4 | 5.4 |
| (Gr. 4) | 5 | 1.5 | 13.83 | 51.3 | 6.4 |
| 8 | 1 | 1.0 | 21.72 | 64.9 | 4.6 |
| (Gr. 3) | 5 | 1.0 | 18.77 | 92.0 | 6.5 |
| 12 | 1 | 1.0 | 31.25 | 86.0 | 6.6 |
| (Gr. 2) | 7 | 1.0 | 48.83 | 213.9 | 7.4 |

$AUC_{0-tz}$: area under the curve until last quantifiable timepoint,
$C_{max}$: maximal concentration,
n.d.: not determined,
$t_{1/2}$: half-life,
$T_{max}$: time to $C_{max}$..

Example 5: In Vivo Distribution and Metabolism Studies

In Vitro Plasma Protein Binding of Compound 1 Plasma

Protein binding of Compound 1 to the plasma from several species, i.e., human, cynomolgus monkey, dog, rat, and mouse was investigated in vitro by incubation in plasma and determination of unbound fraction of Compound 1 using equilibrium dialysis. Compound 1 was incubated in 100% species-specific plasma and added to one side of the membrane in an equilibrium dialysis system while buffer (pH 7.4) is added to the other side. The system was allowed to reach equilibrium at 37° C. Compound concentration on both sides of the membrane is measured by liquid chromatography—tandem mass spectroscopy (LC-MS/MS).

A summary of the data is presented in Table 12. Results showed that Compound 1 plasma protein binding in rat and mouse was in the range as for human plasma proteins, whereas dog and cynomolgus monkey showed a minimally lower Compound 1 plasma protein binding.

TABLE 12

Compound 1 plasma protein binding

| | Fraction unbound (Fu) | |
|---|---|---|
| Species | Mean | SD |
| Human | 0.547 | 0.0332 |
| Dog | 0.619 | 0.0378 |
| Monkey | 0.602 | 0.0352 |
| Mouse | 0.574 | 0.0323 |
| Rat | 0.528 | 0.0301 |

SD: standard deviation

Example 6: Repeat Dose Toxicology Studies

The mouse and the Beagle dog were chosen as relevant animal species for the non-clinical safety evaluation of Compound 1. This selection was based on, inter alia, the amino acid homology of p300/CBP target proteins across animal species. The Compound 1 CH1 target domain of the p300/CBP target proteins show 100% amino acid identity in animal species from mice, rat, dog, cynomolgus monkey, and humans (FIG. 11), which indicates that Compound 1 is cross-reactive in mouse, rat, dog, and cynomolgus monkey (Table 13).

TABLE 13

Amino acid homology and identity for human p300 and CBP to different animal species

| p300 | % Identity | % Similarity |
|---|---|---|
| *Macaca fascicularis* | 98.8 | 99.4 |
| *Felis catus* | 96.3 | 98.1 |
| *Sus scrofa* | 95.6 | 98.1 |
| *Canis lupus familiaris* | 95.4 | 97.4 |
| *Rattus norvegicus* | 93.8 | 97.2 |
| *Mus musculus* | 93.3 | 96.7 |
| CBP | % Identity | % Similarity |
| *Macaca fascicularis* | 99.1 | 99.5 |
| *Rattus norvegicus* | 95.6 | 98.8 |
| *Mus musculus* | 95.4 | 98.4 |
| *Canis lupus familiaris* | 95.3 | 98.4 |
| *Sus scrofa* | 95.3 | 98.7 |
| *Felis catus* | 94.9 | 98.0 |

CBP and p300 protein sequence similarities between human and laboratory mammalian animal species. Data were compiled using the software Geneious Prime V.2020.1.2 and built-in alignment algorithm.

Figure 11:
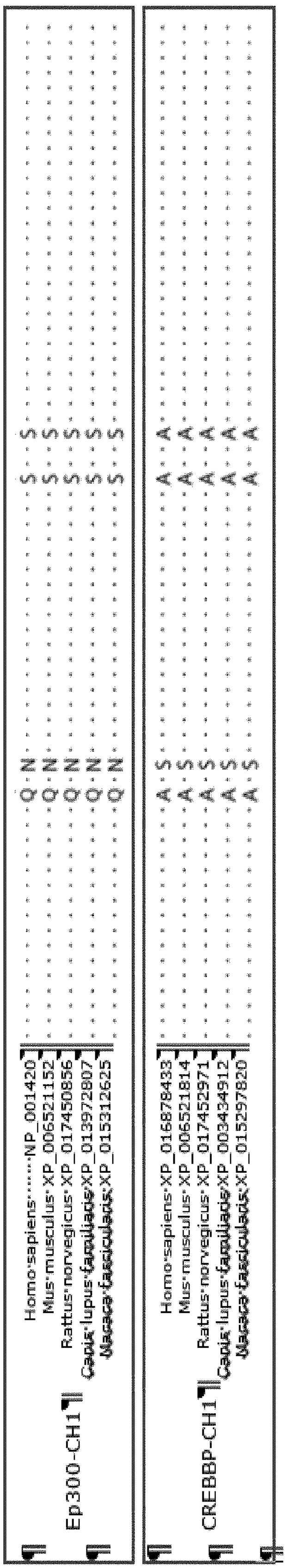
FIG. 11 shows amino acid sequence alignment of the core CH1 (TAZ1) domain of p300 and CBP proteins from several mammalian species.

The alignment is shown in graphical form in FIG. 11. In FIG. 11, identical amino acid positions are indicated by dots, whereas positions having differences between the Ep300-CH1 and the CREB (CBP)-CH1 domains are indicated by single letters for the corresponding amino acids. Full-length reference sequences were retrieved from GenBank and aligned using the software Geneious Prime (version 2020.1.2, Biomatters Ldt, Auckland, New Zealand) with the Blosum62 cost matrix (gap open penalty: 12, extension penalty: 3, two refinement iterations).

The toxicity of Compound 1 was assessed for several dosing regimens for CD-1 mice, Beagle dogs, and cynomolgus monkeys. The design of these studies is summarized in Table 14.

TABLE 14

Design of studies in CD-1 mice, Beagle dogs, and cynomolgus monkeys.

| Animal | Dosage (mg/kg) | Duration | Route of Administration | No. Animals |
|---|---|---|---|---|
| Mouse | 300 mg/kg/week | 4 consecutive | po | 3 |
| | 600 mg/kg/week | weeks | | 3 |
| | 30 mg/kg/day | 5 consecutive | po | 8 |
| | 60 mg/kg/day | days | | 8 |
| | 1 mg/kg/day | 14 consecutive | po | 16 |
| | 5 mg/kg/day | days | | 16 |
| | 10 mg/kg/day | | | 16 |
| | 15 mg/kg/day | | | 16 |
| | 0.5 mg/kg/day | 5 consecutive | IV | 16 |
| | 2 mg/kg/day | days | | 16 |
| | 6 mg/kg/day | | | 16 |
| | 12 mg/kg/day | | | 16 |
| Dog | 10 mg/kg/adm | 4 consecutive doses on study | po | 4 |
| | 15 mg/kg/adm | days 1, 8, 15, | | 2 |
| | 20 mg/kg/adm | and 22 | | 4 |
| | 1.5 mg/kg/day | 5 consecutive | po | 4 |
| | 2.0 mg/kg/day | days | | 4 |
| | 0.1 mg/kg/day | once daily for | po | 2 |
| | 0.3 mg/kg/day | up to 14 | | 2 |
| | 1 mg/kg/day | consecutive | | 2 |
| | 3 mg/kg/day | days | | 2 |
| | 6 mg/kg/day | | | 2 |
| | 12 mg/kg/day | | | 2 |
| Monkey | 30 mg/kg/adm | 4 consecutive | po | 4 |
| | 45 mg/kg/adm | doses on study | | 4 |
| | 60 mg/kg/adm | days 1, 8, 15, | | 2 |
| | 90 mg/kg/adm | and 22 | | 4 |
| | 8 mg/kg/day | 5 consecutive | po | 2 |
| | 12 mg/kg/day | days | | 2 |
| | 16 mg/kg/day | | | 2 |
| | 0.5 mg/kg/day | once daily for | po | 2 |
| | 4 mg/kg/day | up to 14 | | 2 |
| | 8 mg/kg/day | consecutive | | 2 |
| | 12 mg/kg/day | days | | 2 |

Compound 1 administered once weekly orally for 4 weeks at 300 and 600 mg/kg/week was well tolerated in male CD-1 mice.

Compound 1 administered once daily for 5 consecutive days orally at 30 mg/kg/day was well-tolerated in CD-1 mice.

Compound 1 at dose levels of 1, 5, 10, and 15 mg/kg/day was well-tolerated in male and female mice when dosed orally once daily for 14 consecutive days. TK analysis revealed a generally dose dependent and dose-proportional increase in $C_{max}$ and AUC on Day 1 with a trend for accumulation after repeated dosing on Day 14.

Compound 1 at dose levels of 0.5, 2, 6, and 12 mg/kg/day was well-tolerated in mice when dosed intravenously once daily for 5 consecutive days. Toxicokinetic revealed a generally dose dependent increase in CO and AUC on Day 1 and Day 5.

Weekly oral administrations of Compound 1 for 4 consecutive weeks at 10 mg/kg/adm were tolerated in Beagle dogs.

Compound 1 administration at 15 mg/kg/adm was limited to administration of 2 oral doses (Days 1 and 8) to Beagle dogs due to clinical signs. Clinical signs consisted of reduced food and water intake starting after the first dose, resulting in body weight reduction.

A single oral administration of 20 mg/kg/adm was not tolerated in one female Beagle dog. As a consequence, dosing in this dose group was discontinued after the first dose.

Daily oral administration of Compound 1 for 5 consecutive days at 1.5 mg/kg/day was well-tolerated in Beagle dogs.

Daily consecutive oral dosing of Compound 1 at 0.1 and 0.3 mg/kg/day for 14 days and 1 mg/kg/day for 6 days to Beagle dogs was well-tolerated.

Daily consecutive oral dosing of Compound 1 at 3, 6, and 12 mg/kg/day for 14 days to Beagle dogs was not well-tolerated.

Weekly oral administration of Compound 1 for 4 consecutive weeks at 30, 45, and 60 mg/kg/administration (adm) was well-tolerated in cynomolgus monkeys. A single oral administration of 90 mg/kg/adm resulted in side effects in one animal with the consequence, that dosing at 90 mg/kg was discontinued.

Oral administration of Compound 1 to cynomolgus monkeys at dose levels of 8, 12, and 16 mg/kg/day was tolerated for 5 consecutive days with findings of slight body weight loss and changes in hematology, urinalysis, and/or clinical chemistry parameters.

Daily consecutive dosing of Compound 1 at 0.5 and 4 mg/kg/day for 10 or 12 days was tolerated in cynomolgus monkeys.

Daily consecutive dosing of Compound 1 at 8 and 12 mg/kg/day dosages for 10 days was not tolerated in cynomolgus monkeys.

Example 7: In-Human Phase 1 Study of Safety, Tolerability, and Anti-Tumor Activity of Compound 1

The safety and tolerability of Compound 1 will be evaluated in an open label, non-randomized, uncontrolled, multiple dose escalation study (Part I), followed by Part II to assess preliminary anti-tumor activity and confirm the safety of single agent use of Compound 1 consisting of individual expansion cohorts.

Patients with histologically or cytologically confirmed advanced/metastatic CRPC who exhibit documented disease progression, defined according to Prostate Cancer Working Group 3 criteria (Scher et al., J Clin Oncol. 2016 Apr. 20; 34(12):1402-18.), after failure of 2nd generation ADT therapy (enzalutamide, abiraterone, daralutamide, apalutamide), and taxane (Docetaxel, Cabazitaxel) and without other standard therapy options (or who are not eligible or do not tolerate other therapies) are administered Compound 1.). Also advanced progressing SCLC patients after prior chemotherapy treatment are enrolled in both parts of the clinical trial for whom no standard therapies are available.

Part I is a one to three center adaptive multiple ascending dose study of Compound 1 monotherapy. Compound 1 is started on a once weekly schedule PO and will dose escalate based on safety and PK. The administration schedule may be adapted during dose escalation (e.g., 2 days on/5 days off, or twice weekly, every other week) depending on the PK and safety signals that are observed in the clinic and justifying such change.

The first dose cohort starts at a dose level determined by the final preclinical safety and toxicity data set, including results from the GLP-compliant toxicity studies, and 3 patients are enrolled in a staggered fashion. The first 2 patients in every cohort are treated with a minimum interval of 1 week in between, while subsequent patients of a dose cohort may be enrolled concurrently.

DLT-evaluable subjects are those who have completed a DLT assessment period (minimum required 2 administrations and followed by 1 week of observation time, plus the additional allowed days [maximum 3 days per DLT period] in case of treatment delays due to non-safety causes). This population is used for the determination of the dose level increases and of the MTD. Patients experiencing a DLT have to be discontinued from treatment.

Dose escalation decisions and selection of the dose for the next cohort of patients are made following review of all relevant available data and not solely on DLT information.

The MAD part starts with a weekly dosing schedule and maximum allowable dose increments. The escalation scheme will be based on safety and pharmacokinetics.

The dose is escalated in approximately 8 dose levels and approximately 24-30 DLT-evaluable patients are enrolled in Part I. The RP2D and/or MTD are selected based on the overall cumulative clinical safety and activity, as well as the PK and available PD data for Compound 1.

Part II begins once the MTD/RP2D is defined and consists of individual expansion cohorts that enroll advanced CRPC and SCLC patients, respectively. In Part II the safety and tolerability of the RP2D is further tested and PK/PD further explored in patients potentially benefiting from the study treatment. The clinical activity at RP2D is also tested, and tumor tissue profiling is done at baseline and after Cycle 1 (21 days, comprising 3 completed QW dosing periods of Compound 1 or adjusted number of doses/schedule). Therefore, in Part II, patients must have tumors accessible for, and have consented to, tumor biopsy.

In the planned expansion cohorts of Part II in CRPC and SCLC, respectively, approximately 15-20 response-evaluable patients at the determined MTD/RP2D will be enrolled in each indication-specific cohort. If data support that more than one dose level is expanded in Part II, then the assignment of patients to a cohort will be randomized. Further expansion cohorts also comprising further cancer indications may also be included.

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

What is claimed is:

1. A method of treating cancer comprising administering Compound 1:

(Compound 1)

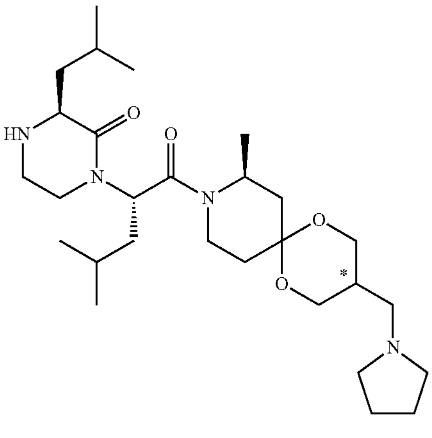

, or a pharmaceutically acceptable salt, hydrate, solvate, or stereoisomer thereof, to a subject at a dosage from about 0.01 mg/kg to about 60 mg/kg, followed by a dosing holiday, wherein the dosing holiday is followed by resuming administration of Compound 1.

2. The method of claim 1, wherein Compound 1 is administered at a dosage selected from the group consisting of: from about 0.01 mg/kg to about 50 mg/kg, from about 0.01 mg/kg to about 40 mg/kg, from about 0.01 mg/kg to about 30 mg/kg, from about 0.01 mg/kg to about 25 mg/kg, from about 0.01 mg/kg to about 20 mg/kg, from about 0.01 mg/kg to about 15 mg/kg, from about 0.01 mg/kg to about 10 mg/kg, from about 0.01 mg/kg to about 5 mg/kg, from about 0.01 mg/kg to about 3 mg/kg, from about 0.01 mg/kg to about 2 mg/kg.

3. The method of claim 1 wherein Compound 1 is administered once every seven days.

4. The method of claim 1, wherein Compound 1 is administered once every seven days followed by a dosing holiday, wherein the dosing holiday is followed by resuming administration of Compound 1.

5. The method of claim 1, wherein Compound 1 is administered once daily followed by a dosing holiday, wherein the dosing holiday is followed by resuming administration of Compound 1.

6. The method of claim 1, wherein Compound 1 is administered once daily.

7. The method of claim 1, wherein the cancer comprises prostate cancer, renal cancer, pancreatic cancer, liver cancer, breast cancer, gastric cancer, colon cancer, cervical cancer, ovarian cancer, head-and-neck cancer, esophageal cancer, hematological cancer, brain cancer, stomach cancer, cancer of the central nervous system, skin cancer, or lung cancer.

8. The method of claim 7, wherein the prostate cancer is castrate resistant prostate cancer (CRPC) or neuroendocrine prostate cancer (NEPC).

9. The method of claim 1, wherein Compound 1 is Compound 1':

(Compound 1')

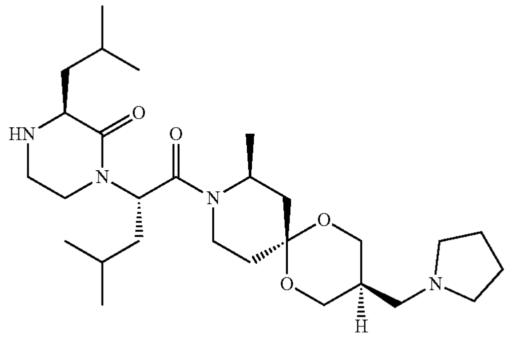

, or a pharmaceutically acceptable salt, hydrate, solvate, or stereoisomer thereof.

10. A method of treating cancer comprising administering the methanesulfonic acid salt of Compound 1':

(Compound 1')

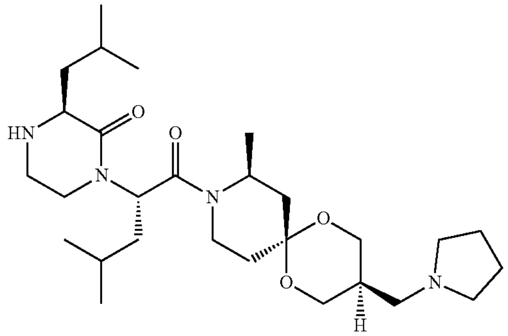

, to a subject at a dosage from about 0.01 mg/kg to about 60 mg/kg, followed by a dosing holiday, wherein the dosing holiday is followed by resuming administration of Compound 1'.

11. The method of claim 1, wherein Compound 1 is administered at a dosage from about 0.03 mg/kg to about 0.55 mg/kg once daily.

12. The method of claim 1, wherein Compound 1 is administered at a dosage from about 0.4 mg/kg to about 15 mg/kg once every seven days.

13. The method of claim 1, wherein the Compound 1 is administered at a dosage from about 0.4 mg/kg to about 15 mg/kg once every seven days followed by a one week dosing holiday.

14. The method of claim 1, wherein the Compound 1 is administered at a dosage from about 0.08 mg/kg to about 1.2 mg/kg once daily for seven days followed by a seven day dosing holiday.

15. The method of claim 1, wherein the Compound 1 is administered orally.

* * * * *